United States Patent
Fotsch et al.

(10) Patent No.: US 6,977,264 B2
(45) Date of Patent: Dec. 20, 2005

(54) SUBSTITUTED PIPERIDINES AND METHODS OF USE

(75) Inventors: Christopher H. Fotsch, Thousand Oaks, CA (US); Michael Croghan, Thousand Oaks, CA (US); Elizabeth M. Doherty, Newbury Park, CA (US); Michael G. Kelly, South San Francisco, CA (US); Mark H. Norman, Thousand Oaks, CA (US); Duncan M. Smith, Thousand Oaks, CA (US); Nuria Tamayo, Newbury Park, CA (US); Ning Xi, Thousand Oaks, CA (US); Shimin Xu, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 136 days.

(21) Appl. No.: 10/205,649

(22) Filed: Jul. 24, 2002

(65) Prior Publication Data

US 2004/0006067 A1 Jan. 8, 2004

Related U.S. Application Data

(60) Provisional application No. 60/307,733, filed on Jul. 25, 2001.

(51) Int. Cl.$^7$ ................. C07D 211/06; A61K 31/445
(52) U.S. Cl. ........................................ 514/330; 546/226
(58) Field of Search ........................ 514/330; 546/226

(56) References Cited

FOREIGN PATENT DOCUMENTS

| | | |
|---|---|---|
| WO | WO 01/10842 A2 | 2/2001 |
| WO | WO 02/059095 A1 | 8/2002 |
| WO | WO 02/059107 A1 | 8/2002 |
| WO | WO 02/059108 A1 | 8/2002 |
| WO | WO 02/059117 A1 | 8/2002 |
| WO | WO 02/062766 A2 | 8/2002 |
| WO | WO 02/067869 A2 | 9/2002 |
| WO | WO 02/068387 A2 | 9/2002 |
| WO | WO 02/068388 A2 | 9/2002 |
| WO | WO 02/069905 A2 | 9/2002 |
| WO | WO 02/079146 A2 | 10/2002 |
| WO | WO 03/061660 A1 | 7/2003 |
| WO | WO 03/063781 A2 | 8/2003 |

*Primary Examiner*—Zinna Northington Davis
(74) *Attorney, Agent, or Firm*—Joseph W. Bulock

(57) ABSTRACT

Selected substituted piperidine compounds are effective for prophylaxis and treatment of diseases, such as obesity and the like. The invention encompasses novel compounds, analogs, prodrugs and pharmaceutically acceptable salts thereof, pharmaceutical compositions and methods for prophylaxis and treatment of diseases and other maladies or conditions involving activation of the melanocortin receptor. The subject invention also relates to processes for making such compounds as well as to intermediates useful in such processes.

19 Claims, No Drawings

SUBSTITUTED PIPERIDINES AND METHODS OF USE

This application claims the benefit of U.S. Provisional Application No. 60/307,733 filed Jul. 25, 2001, which is hereby incorporated by reference.

FIELD OF THE INVENTION

The present invention relates generally to the fields of medicinal chemistry and, more specifically, to novel compounds and their use as anti-obesity agents.

BACKGROUND OF THE INVENTION

Obesity, defined as an excess of body fat relative to lean body mass, contributes to and complicates other diseases. For example, obesity substantially increases the risk of morbidity from hypertension, dyslipidemia, type 2 diabetes, coronary artery disease, stroke, gallbladder disease, osteoarthritis, sleep apnea and respiratory problems, as well as cancers of the endometrium, breast, prostate and colon. As a major cause of preventable death in the United States today, obesity poses a major public health challenge.

Overweight is defined today as a body mass index (BMI) of 25–29.9 $kg/m^2$, and obesity is defined as a BMI≧30 $kg/m^2$. Over 60% of the adult population of the United States and Australia are either overweight (BMI of 25–29.9 $kg/m^2$) or obese (BMI>30 $kg/m^2$). More than 20% of adults fall into this latter category.

The cause of obesity is quite complex and not merely the result of voluntary overeating. Rather, the differential body composition observed between obese and normal subjects results from differences in both metabolism and neurologic/metabolic interactions.

The purpose of weight loss and weight maintenance is to reduce health risks. If weight is regained, health risks increase. A majority of patients who lose weight regain it, so the challenge to the patient and the practitioner is to maintain weight loss. Because of the tendency to regain weight after weight loss, the use of long-term medication to aid in the treatment of obesity may be indicated for carefully selected patients.

The drugs used to promote weight loss are traditionally anorexiants or appetite suppressants. Three classes of anorexiant drugs have been developed, all of which affect neurotransmitters in the brain. They may be designated as follows: (1) those that affect catecholamines, such as dopamine and norepinephrine; (2) those that affect serotonin; and (3) those that affect more than one neurotransmitter. These drugs work by increasing the secretion of dopamine, norepinephrine, or serotonin into the synaptic neural cleft, by inhibiting the reuptake of these neurotransmitters into the neuron, or by a combination of both mechanisms. Sibutramine inhibits the reuptake of norepinephrine and serotonin. Orlistat is not an appetite suppressant and has a different mechanism of action; it blocks about one-third of fat absorption.

Weight loss drugs approved by the FDA for long-term use may be useful as an adjunct to diet and physical activity for patients with a BMI>27 who also have concomitant obesity-related risk factors or diseases. Our thinking about drug therapy has undergone radical changes over the past few years.

Of recent interest as a target has been the melanocortin receptor family. The term melanocortin ("MC") defines a family of peptide hormones that regulate diverse physiological functions through transmembrane G-protein coupled receptors. Melanocortins include melanocyte-stimulating hormones (MSH) such as α-MSH, β-MSH and γ-MSH, as well as adrenocorticotropic hormone (ACTH). The melanocortin (MC) receptors ("MCRs") are a group of cell surface proteins that mediate a variety of physiological effects, including adrenal gland function, production of cortisol and aldosterone, control of melanocyte growth and pigment production, thermoregulation, immunomodulation and analgesia. In the past several years, five distinct melanocortin receptor subtypes have been identified. The five MC receptors, termed MCR1, MCR2, MCR3, MCR4 and MCR5, all couple in a stimulatory fashion to cAMP. MCR1, MCR3, MCR4 and MCR5 constitute subtypes of MSH receptors. The MCRs stimulate adenyl cyclase to generate cAMP.

The MC1 receptor is present on melanocytes and melanoma and is involved in skin pigmentation. The MCR2 receptor is the ACTH receptor and is present predominantly in the adrenal gland. MCR2 plays a role in adrenal steroidogenesis. The mRNA for the MCR3 receptor has been found in the brain, as well as in placental and gut tissues. The MCR4 receptor has been found primarily in the brain. The MCR5 receptor is expressed in the brain, as well as in several peripheral tissues and has been implicated in exocrine gland function.

The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as-other events related to parturition.

Recently, MC receptor MCR4 has been shown to function in the regulation of body weight and food intake. Early studies on mice that expressed agouti ectopically, which is a MCR4 antagonist, produced obese animals. Subsequent work has shown that MCR3 and MCR4 antagonists stimulated food intake and that MCR4 knockout mice are obese. Synthetic MC4 agonist peptides that mimic melanocortins and bind to MCR4 injected into the brain, cause suppression of feeding in normal and mutant obese mice. Targeted disruption of MCR4 causes mice to develop a maturity onset of obesity associated with hyperphagia, hyperinsulinemia and hyperglycemia (Huszar et al., supra). Stimulation of the MC4 receptor by an endogenous ligand, α-MSH, produces a satiety signal and may be the downstream mediator of the leptin signalling pathway. These results indicate that the brain MC receptor MCR-4 functions in regulating food intake and body weight and is a promising target in the treatment of obesity. It is believed that by providing potent MC-4 receptor agonists, appetite may be suppressed and weight loss benefits may be achieved. See J. Wikberg, Eur. J. Pharm., 375, 295–310 (1999).

Melanotan II (MTII) is an α-MSH peptide superagonist for MCR4. (M. Hadley et al., Discovery and Development of Novel Melanogenic Drugs, Integration of Pharmaceutical Discovery and Development: Case Studies, Borchardt et al., ed., Plenum Press, New York 1998). Other cyclic and linear α-MSH peptides also have been studied. See, for example, C. Haskell-Luevano et al., J. Med. Chem., 40, 2133–39 (1997); H. Schiöth et al., Brit. J. Pharmacol, 124, 75–82

(1998); H. Schiöth et al., Eur. J. Pharmacol., 349, 359–66 (1998); M. Hadley et al., Pigment Cell Res., 9, 213–34 (1996); M. Bednarek et al., Peptides, 20, 401–09 (1999); and U.S. Pat. Nos. 6,054,556, 6,051,555 and 5,576,290.

WO98/11128, published 19 Mar. 1998, describes phenylalanine derivatives. WO00/78317, published 28 Dec. 2000, describes piperidine derivatives as integrin receptor antagonists. EP1086947, published 29 Aug. 2000, describes piperidine compounds as agonists and antagonists for the SST receptor. WO00/35871, published 22 Jun. 2000, describes arylpiperidine compounds as intermediates for the preparation of 5HT1A agonists and antagonists. WO00/35875, published 22 Jun. 2000, describes arylpiperidine compounds as intermediates for the preparation of 5HT1A agonists and antagonists. WO00/25786, published 11 May 2000, describes substituted piperidines as potassium channel inhibitors. U.S. Pat. No. 5,518,735, issued May 21, 1996, describes phenylalanine derivatives which prevent coagulation or thrombosis. WO97/19908, published 5 Jun. 1997, describes phenylalanine derivatives as fungicides. WO97/49673, published 31 Dec. 1997, describes phenylalanine derivatives as thrombin inhibitors.

WO95/34311, published 21 Dec. 1995, describes substituted piperazine compounds as growth hormone releasing agents. U.S. Pat. No. 5,681,954, issued Oct. 28, 1997, describes substituted piperazines as inhibitors of calmodulin. WO97/03060, published 30 Jan. 1997, describes piperazine derivatives as cysteine protease inhibitors. U.S. Pat. No. 6,057,290, issued May 2, 2000, describes piperazine derivatives as cysteine protease inhibitors. WO97/19919, published 5 Jun. 1997, describes sulfonamides as having anti-thrombin activity. U.S. Pat. No. 5,244,895, issued Sep. 14, 1993, describes piperazine derivatives as antiulcer agents. EP 513691, published 31 Jul. 1996, describes piperazine derivatives as antiulcer agents. U.S. Pat. No. 5,244,895, issued Sep. 14, 1993, describes sulfonamides having smooth muscle relaxation activity. WO94/05693, published 17 Mar. 1994, describes piperazinyl-phenylalanine derivatives as tachyquinine antagonists. J. Sturzebecher et al. J. Enzyme Inhib., 9, 87–99 (1995), describes piperazinyl-phenylalanine derivatives as thrombin inhibitors. M. Böhm et al. J. Med. Chem., 42, 458–77 (1999), describes piperazinyl-phenylalanine derivatives as thrombin inhibitors. J. Sturzebecher et al., J. Med. Chem., 40, 3091–99 (1997), describes piperazinyl-phenylalanine derivatives as thrombin inhibitors. H. Sakamoto, et al. Pept. Chem., 27, 375–8 (1989) describes piperazinyl-phenylalanine derivatives as chymotrypsin inhibitors. H. Sakamoto, et al., Bull. Chem. Soc. Jpn., 64, 2519–23 (1991) describes piperazinyl-phenylalanine derivatives as chymotrypsin inhibitors. G. Wagner, et al., Pharmazie, 36, 597–603 (1981), describes piperazinyl-phenylalanine derivatives as serine protease inhibitors. E. J. Jacobsen et al. J. Med. Chem., 42, 1525–36 (1999) describes thiazolyl ureas as stromelysin inhibitors. WO97/40031, published 30 Oct. 19978, describes thiazolyl ureas as metalloprotease inhibitors.

WO01/10842, published 15 Feb. 2001, describes melanocortin receptor binding compounds. WO99/64002, published 16 Dec. 1999, describes spiropiperidines as melanocortin receptor agonists. WO00/74679, published 14 Dec. 2000, describes piperidine compounds as melanocortin receptor agonists.

However, compounds of the current invention have not been described as inhibitors of MCRs such as for the treatment of obesity.

DESCRIPTION OF THE INVENTION

A class of compounds useful in treating obesity is defined by Formula I

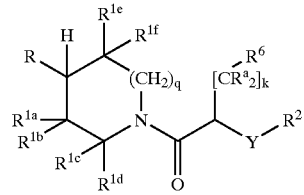

I wherein Y is —NH—, —CH$_2$—, or —O—;
  preferably —NH— or —CH$_2$—; and
    more preferably —NH—;
wherein R is selected from
  a) alkyl,
  b) —(CH$_2$)$_n$-cycloalkyl,
  c) —(CH$_2$)$_n$-aryl, and
  d) —(CH$_2$)$_n$-heterocyclyl;
    wherein the cycloalkyl and aryl groups are optionally substituted with 1 to 3 groups selected from R$^4$; the heterocyclyl group is optionally substituted with 1 to 3 groups selected from R$^4$ and oxo; and the alkyl group is optionally substituted with 1 to 3 groups selected from R$^5$;
  preferably selected from
  a) —(CH$_2$)$_n$—C$_{3-8}$-cycloalkyl,
  b) -aryl,
  c) unsubstituted benzyl, and
  d) —(CH$_2$)$_n$-5–6-membered heterocyclyl;
    wherein R is substituted at the 2-position of the cycloalkyl, heterocyclyl, benzyl and aryl groups with a radical selected from R$^4$; and wherein the cycloalkyl and aryl groups are optionally substituted with 1 to 2 additional radicals selected from R$^4$; and the heterocyclyl group is optionally substituted with 1 to 2 additional radicals selected from R$^4$ and oxo;
    more preferably R is phenyl ortho substituted with a radical selected from R$^4$ and optionally substituted with a radical selected from R$^4$;
    even more preferably

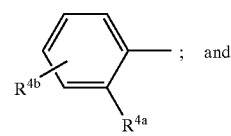

; and of particular importance

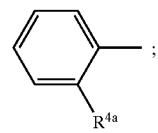

;

wherein R$^{1a}$, R$^{1b}$, R$^{1c}$, R$^{1d}$, R$^{1e}$, and R$^{1f}$ are independently selected from R$^4$; or wherein R$^{1a}$ and R$^{1b}$, or R$^{1d}$ and R$^{1c}$ form oxo; or wherein R$^{1e}$ and R$^{1c}$ form an alkenyl or alkenylenyl bridge; or wherein R$^{1a}$, R$^{1b}$, R$^{1c}$, and R$^{1d}$ together with the piperazine ring forms an optionally substituted 1,2,3,4-tetrahydro-quinoxalinyl ring;

preferably wherein $R^{1a\text{-}f}$ are independently selected from $R^4$; or wherein $R^{1a}$ and $R^{1b}$ or $R^{1d}$ and $R^{1c}$ form oxo; or wherein $R^{1e}$ and $R^{1c}$ form an $C_{1\text{-}4}$-alkylenyl or $C_{2\text{-}4}$-alkenylenyl bridge; or wherein $R^{1a}$, $R^{1b}$, $R^{1c}$, and $R^{1d}$ together with the piperazine ring forms an optionally substituted 1,2,3,4-tetrahydro-quinoxalinyl ring; and more preferably $R^{1a\text{-}f}$ are independently selected from $R^4$; or wherein $R^{1a}$ and $R^{1b}$ or $R^{1d}$ and $R^{1c}$ form oxo; even more preferably $R^{1a\text{-}f}$ are H;

wherein $R^2$ is selected from
- a) alkyl,
- b) —$(CH_2)_n$-cycloalkyl,
- c) —$(CH_2)_n$-aryl,
- d) —$(CH_2)_n$-heterocyclyl, e) 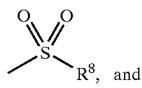

f) 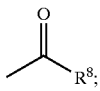

wherein the cycloalkyl and aryl groups are optionally substituted with 1 to 3 groups selected from $R^4$; the heterocyclyl group is optionally substituted with 1 to 3 groups selected from $R^4$ and oxo; and the alkyl group is optionally substituted with 1 to 3 groups selected from $R^5$;

preferably selected from
- a) —$(CH_2)_n$—$C_{3\text{-}9}$-cycloalkyl,
- b) —$(CH_2)_n$-aryl,
- c) —$(CH_2)_n$-4–10-membered heterocyclyl, d) 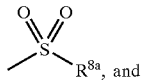

e) 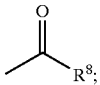

wherein the cycloalkyl and aryl groups are optionally substituted with 1 to 3 groups selected from $R^4$; and the heterocyclyl group is optionally substituted with 1 to 3 groups selected from $R^4$ and oxo;

more preferably selected from
- a) —$(CH_2)_n$—$C_{3\text{-}6}$-cycloalkyl,
- b) —$(CH_2)_n$-phenyl,
- c) —$(CH_2)_n$-5–10-membered heterocyclyl, and d) 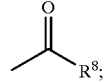

wherein the cycloalkyl and aryl groups are optionally substituted with 1 to 3 radicals selected from $R^4$; and the heterocyclyl group is optionally substituted with 1 to 3 radicals selected from $R^4$ and oxo;

even more preferably selected from
- a) —$(CH_2)_n$—$C_{3\text{-}6}$-cycloalkyl,
- b) —$(CH_2)_n$-phenyl, and
- c)-$(CH_2)_n$-6–10-membered heterocyclyl; wherein the cycloalkyl and aryl groups are optionally substituted with 1 to 2 groups selected from $R^{4b}$; and the heterocyclyl group is optionally substituted with 1 to 2 groups selected from $R^{4b}$ and oxo; and of particular importance selected from

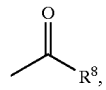

indolyl$(CH_2)_n$—, phenyl $(CH_2)_n$—, benzoxazolyl $(CH_2)_n$—, oxazolo[4,5-b]pyridyl$(CH_2)_n$—, oxazolo[5,4-b]pyridyl$(CH_2)_n$—, benzoxazolyl $(CH_2)_n$—, 1,2,3,4-tetrahydro-isoquinolyl$(CH_2)_n$—, pyridyl $(CH_2)_n$— and 2,3-dihydro-benzo[1,4]dioxanyl $(CH_2)_n$—;

wherein $R^2$ is optionally substituted with 1 to 2 groups selected from $R^{4b}$;

wherein $R^3$ is independently selected from H, halo, amino, haloalkyl, alkyl, phenyl, haloalkoxy, and alkoxy; or $R^3$ is an alkenylene bridge;

preferably H, halo, amino, $C_{1\text{-}6}$-haloalkyl, $C_{1\text{-}6}$-alkyl, phenyl, $C_{1\text{-}6}$-haloalkoxy and $C_{1\text{-}6}$-alkoxy; or $R^3$ is an $C_{2\text{-}4}$-alkenylene bridge;

more preferably H, chloro, bromo, iodo, phenyl, fluoro, amino, $C_{1\text{-}2}$-alkyl, $C_{1\text{-}2}$-haloalkyl, $C_{1\text{-}2}$-haloalkoxy and $C_{1\text{-}2}$-alkoxy;

even more preferably H, chloro, bromo, iodo, fluoro, amino, methyl, methoxy, trifluoromethyl and trifluoromethoxy;

and of particular interest are H, chloro, bromo, amino, methyl, trifluoromethyl and methoxy;

wherein $R^4$ is selected from H, alkyl, —$(CH_2)_n$-cycloalkyl, —$(CH_2)_n$-aryl, —$(CH_2)_n$-heterocyclyl, halo, —$(CH_2)_n$—$OR^9$, —$NR^9SO_2R^7$, —$[C(R^7)_2]_pNR^9SO_2R^7$, —$[C(R^7)_2]_pNR^9C(O)R^7$, —$N(R^9)_2$, —$C(O)NR^9R^9$, —$NR^9C(O)R^7$, —$NR^9CO_2R^7$, cyano, —$COOR^9$, —$(CH_2)_n$—$C$=$OR^7$, —$(CH_2)_n$—$C$=$SR^7$, —$(CH_2)_n$—$C$=$(NR^9)R^7$, —$NR^9C$=$(NR^7)N(R^9)_2$, —$[C(R^7)_2]_pN(R^9)_2$, nitro, —$SO_2N(R^9)_2$—$S(O)_mR^7$, —$C(R^7)_2SO_2CF_3$, hydroxyalkyl, haloalkyl and haloalkoxy;

preferably H, $C_{1\text{-}6}$-alkyl, —$(CH_2)_n$—$C_{3\text{-}6}$-cycloalkyl, —$(CH_2)_n$-aryl, —$(CH_2)_n$-4–10-membered heterocyclyl, halo, —$(CH_2)_n$—$OR^9$, —$NR^9SO_2R^7$, —$N(R^9)_2$, —$C(O)NR^9R^9$, —$NR^9C(O)R^7$, —$NR^9CO_2R^7$, nitro, cyano, —$(CH_2)_n$—$C(O)R^7$—$C(O)OR^9$, —$(CH_2)_n$—$C(S)R^7$, —$(CH_2)_n$—$C$=$(NR^9)R^7$, —$NR^9C$=$(NR^7)N(R^7)_2$, $[C(R^7)_2]NR^9SO_2R^7$, —$[C(R^7)_2]_pNR^9C(O)R^7$, —$[C(R^7)_2]_pN(R^9)_2$, —$SO_2N(R^9)_2$, —$S(O)_mR^7$, —$C(R^7)_2SO_2CF_3$, $C_{1\text{-}6}$-hydroxyalkyl, $C_{1\text{-}6}$-haloalkyl and $C_{1\text{-}6}$-haloalkoxy; and more preferably H, $C_{1\text{-}2}$-alkyl, —$(CH_2)_n$—$C_{5\text{-}6}$-cycloalkyl, —$(CH_2)_n$-phenyl, —$(CH_2)_n$-4–10-membered heterocyclyl, fluoro, chloro, —$(CH_2)_n$—$OR^{9a}$, —$NR^{9a}SO_2R^7$, —$NR^{9a}R^{9b}$, —$C(O)NR^{9a}R^{9b}$, —$NR^{9a}C(O)R^7$, cyano, nitro, —$(CH_2)_n$—$C(O)R^7$, —$C(O)OR^{9a}$, —$(CH_2)_n$—$C(S)R^7$, —$(CH_2)_n$—$C$=$(NR^{9a})R^7$, —$NR^{9a}C$=$(NR^{9a})N(R^7)_2$, —$[C(R^7)_2]_pNR^{9a}R^{9b}$, —$[CH_2]_pNR^{9a}SO_2R^7$, —$[CH_2]_pNR^{9a}C(O)R^7$, —$SO_2NR^{9a}R^{9b}$, —$S(O)_mR^7$, —$C(R^7)_2SO_2CF_3$, $C_{1\text{-}2}$-hydroxyalkyl $C_{1\text{-}2}$-haloalkyl and $C_{1\text{-}2}$-haloalkoxy;

wherein $R^{4a}$ is selected from —$(CH_2)_n$—$OR^{9a}$, —$NR^{9a}SO_2R^{7a}$, 4–6-membered heterocyclyl, —$[CH_2]_p$ $NR^{9a}SO_2R^{7a}$, —$NR^{9a}R^{9b}$, —$C(O)NR^{9a}R^{9b}$, —$NR^{9b}C(O)$ $R^{7a}$, —$[CH_2]_p NR^{9b}C(O)R^{7a}$, —$(CH_2)_n$—$C(O)R^{7a}$, nitro, —$C(O)OR^{9a}$, —$(CH_2)_n$—$C(S)R^{7a}$, —$[C(R^{7a})_2]NR^{9a}R^{9b}$ —$SO_2NR^{9a}R^{9b}$, —$S(O)_m R^{7a}$ and —$C(R^{7a})_2SO_2CF_3$;

preferably 4–5-membered heterocyclyl, —$NR^{9a}SO_2R^{7a}$, —$NR^{9a}R^{9b}$, —$C(O)NR^{9a}R^{9b}$, —$C_{1-3}$—$NR^{9a}SO_2R^{7a}$, —$C_{1-3}$—$NR^{9a}C(O)R^{7b}$, —$NR^{9b}C(O)R^{7a}$ and —$C_{1-3}$—$NR^{9a}R^{9b}$; and more preferably selected from —$C_{1-2}$-alkyl-$NR^{9a}SO_2R^{7a}$ —$NR^{9a}SO_2R^{7a}$, 4–5-membered heterocyclyl —$NR^{9a}R^9b$, —$C(O)NR^{9a}R^{9b}$, —$C_{1-2}$-alkyl-$NR^{9a}C(O)R^{7b}$, —$NR^{9b}C(O)R^{7a}$ and —$C_{1-2}$-alkyl-$NR^{9a}R^{9b}$;

wherein $R^{4b}$ is selected from H, $C_{1-2}$-alkyl, —$(CH_2)$—$C_{5-6}$-cycloalkyl, —$(CH_2)_n$-phenyl, —$(CH_2)_n$-4–10-membered heterocyclyl, fluoro, chloro, —$OR^9$a, —$(CH_2)_n$—$OR^{9a}$, —$NR^{9a}SO_2R^{7a}$, —$NR^{9a}R^{9b}$, —$C(O)NR^{9a}R^{9b}$, $NR^{9a}C(O)R^{7b}$, —$(CH_2)_n$—$C(O)R^{7a}$, nitro, —$C(O)OR^{9a}$, —$(CH_2)_n$—$C(S)R^{7a}$ —$[C(R^{7a})_2]_p NR^{9a}R^{9b}$, —$SO_2NR^{9a}R^{9b}$, —$S(O)_m R^{7a}$, —$C(R^{7a})_2 SO_2 CF_3$, cyano, $C_{1-2}$-haloalkyl and $C_{1-2}$-haloalkoxy; and preferably H, methyl, cyclopentyl, cyclohexylmethyl, phenyl, benzyl, —$(CH_2)_n$-4–10-membered heterocyclyl, fluoro, chloro, —$OR^{9a}$, $(CH_2)_n$—$OR^{9a}$, —$NR^{9a}SO_2R^{7a}$, —$NR^{9a}R^{9b}$, —$C(O)NR^{9a}R^{9b}$, —$NR^{9a}C(O)R^{7b}$, —$(CH_2)_n$—$C(O)R^{7a}$, —$C(O)OR^{9a}$, —$[C(R^{7a})_2]_p NR^{9a}R^{9b}$, —$SO_2NR^{9a}R^{9b}$, —$SO_2R^{7a}$, trifluoromethyl and trifluoromethoxy;

wherein $R^5$ is selected from halo, —$OR^9$, $NHSO_2R^7$, —$N(R^9)_2$, cyano, —$COR^7$, —$[C(R^7)_2]_n N(R^9)_2$, nitro, —$SO_2N(R^9)_2$, —$S(O)_m R^7$, haloalkyl, and haloalkoxy;

preferably halo, —$OR^9$, —$NHSO_2R^7$, —$N(R^9)_2$, cyano, —$COR^7$, —$[C(R^7)_2]_n N(R^9)_2$, nitro, —$SO_2 N(R^9)_2$, —$S(O)_m R^7$, $C_{1-6}$-haloalkyl and $C_{1-6}$-haloalkoxy;

more preferably halo, —$OR^{9a}$, —$NR^{9a}R^{9b}$, —$[C(R^7)_2]NR^{9a}R^{9b}$, and —$SO_2NR^{9a}R^9$b; and even more preferably chloro, fluoro, hydroxyl, —$NR^{7a}R^{7b}$ and —$SO_2N(R^{7a})_2$;

wherein $R^6$ is selected from aryl and heteroaryl, wherein $R^6$ is optionally substituted with one or more $R^3$;

preferably phenyl, naphthyl and 6-membered heteroaryl, wherein $R^6$ is optionally substituted with one or more $R^3$;

more preferably naphthyl or phenyl optionally substituted with one or two $R^3$; and of particular interest phenyl optionally substituted with one or two $R^3$;

wherein $R^7$ is selected from H, alkyl, —$(CH_2)_n$-cycloalkyl, —$(CH_2)_n$-heterocyclyl, —$(CH_2)_n$-aryl, aminoalkyl, alkylamino, alkenyl, alkylcarbonylaminoalkyl, alkylthioalkyl, alkylaminoalkyl, alkoxyalkyl and alkoxy;

preferably H, $C_{1-6}$-alkyl, —$(CH_2)_n$—$C_{3-6}$-cycloalkyl, —$(CH_2)_n$-4–10-membered heterocyclyl, —$(CH_2)_n$-phenyl, amino-$C_{1-6}$-alkyl, $C_{1-6}$-alkylamino, $C_{2-6}$-alkenyl, $C_{1-6}$-alkylthio-$C_{1-6}$-alkyl, $C_{1-6}$-alkylcarbonylamino-$C_{1-6}$-alkyl, $C_{1-6}$-alkylamino-$C_{1-6}$-alkyl, $C_{1-6}$-alkoxy-$C_{1-6}$-alkyl and $C_{1-6}$-alkoxy; and more preferably H, $C_{1-4}$-alkyl, —$(CH_2)_n$—$C_{3-6}$-cycloalkyl, —$(CH_2)_n$-4–10-membered heterocyclyl, —$(CH_2)_n$-phenyl, amino-$C_{1-4}$-alkyl, $C_{1-4}$-alkylamino, $C_{2-4}$-alkenyl, $C_{1-4}$-alkylthio-$C_{1-4}$-alkyl, $C_{1-4}$-alkylcarbonylamino-$C_{1-4}$-alkyl, $C_{1-4}$-alkylamino-$C_{1-4}$-alkyl, $C_{1-4}$-alkoxy-$C_{1-4}$-alkyl and $C_{1-4}$-alkoxy;

wherein $R^{7a}$ is selected from H, $C_{1-3}$-alkyl, —$(CH_2)_n$—$C_{3-6}$-cycloalkyl, —$(CH_2)_n$-4–10-membered heterocyclyl and —$(CH_2)_n$-phenyl; and preferably H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;

wherein $R^{7b}$ is selected from amino-$C_{1-3}$-alkyl, $C_{1-3}$-alkoxy, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl-$C_{1-3}$-alkoxy-$C_{1-3}$-alkyl, H, $C_{1-3}$-alkyl, —$(CH_2)_n$—$C_{3-6}$-cycloalkyl, —$(CH_2)_n$-4–10-membered heterocyclyl and —$(CH_2)_n$-phenyl; and preferably amino-$C_{1-3}$-alkyl, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl, $C_{1-3}$-alkoxy, $C_{1-3}$-alkoxy-$C_{1-3}$-alkyl, H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;

wherein $R^8$ is selected from
  a) heterocyclyl,
  b) aminoalkyl,
  c) aminoalkylamino,
  d) alkylaminoalkylamino,
  e) alkylaminoalkyl,
  f) arylaminoalkyl,
  g) arylalkylaminoalkyl,
  h) heterocyclylalkylaminoalkyl,
  i) aryl,
  j) alkyl,
  k) aralkyl,
  l) heterocyclylalkyl,
  m) cycloalkylalkyl,
  n) —$OR^9$
  o) aminoalkoxy,
  p) N-(heterocyclylalkyl)amino,
  q) aralkyl where the alkyl portion is substituted with amino, hydroxy or alkylamino, and
  r) heterocyclylalkylenyl where the alkylenyl portion is substituted with amino, hydroxy or alkylamino; wherein the cycloalkyl and aryl groups are optionally substituted with 1 to 3 groups selected from $R^4$; the heterocyclyl groups are optionally substituted with 1 to 3 groups selected from $R^4$ and oxo; and the alkyl groups are optionally substituted with 1 to 3 groups selected from $R^5$;

preferably selected from
  a) 4–10-membered heterocyclyl,
  b) amino-$C_{1-6}$-alkyl,
  c) amino-$C_{1-6}$-alkylamino,
  d) $C_{1-6}$-alkylamino-$C_{1-6}$-alkylamino,
  e) $C_{1-6}$-alkylamino-$C_{1-6}$-alkyl,
  f) arylamino-$C_{1-6}$-alkyl,
  g) aryl-$C_{1-6}$-alkylamino-$C_{1-6}$-alkyl,
  h) 4–10-membered heterocyclyl-$C_{1-6}$-alkylamino-$C_{1-6}$-alkyl,
  i) aryl,
  j) $C_{1-6}$-alkyl,
  k) aryl-$C_{1-6}$-alkyl,
  l) heterocyclyl-$C_{1-6}$-alkyl,
  m) $C_{3-6}$-cycloalkyl-$(CH_2)_n$—,
  n) —$OR^9$
  o) amino-$C_{1-6}$-alkoxy,
  p) N-(4–10-membered heterocyclyl-$C_{1-6}$-alkyl)amino,
  q) aryl-$C_{1-6}$-alkyl where the alkyl portion is substituted with amino, hydroxy or $C_{1-6}$-alkylamino, and r) 4–10-membered heterocyclyl-$C_{1-6}$-alkylenyl where the alkylenyl portion is substituted with amino, hydroxy or $C_{1-6}$-alkylamino;
more preferably selected from
a) amino-$C_{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenyl-$C_{1-4}$-alkylamino-$C_{1-4}$-alkyl,
f) phenylamino-$C_{1-4}$-alkyl,
g) 4–10-membered heterocyclyl-$C_{1-4}$-alkylamino-$C_{1-4}$-alkyl,
h) N-(4–10-membered heterocyclyl-$C_{1-4}$-alkyl)amino,
i) $C_{1-4}$-alkyl,
j) $C_{3-6}$-cycloalkyl-$(CH_2)_n$—,
k) aryl-$(CH_2)_n$—,
l) 4–10-membered heterocyclyl-$(CH_2)_n$—,
m) $R^{9a}O$—,
n) amino-$C_{1-4}$-alkoxy,
o) phenyl-$C_{1-4}$-alkyl where the alkyl portion is substituted with amino, hydroxy or $C_{1-4}$-alkylamino, and
p) 4–10-membered heterocyclyl-$C_{1-4}$-alkylenyl where the alkylenyl portion is substituted with amino, hydroxy or $C_{1-4}$-alkylamino;
even more preferably selected from
a) amino amino-$C_{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenylamino-$C_{1-4}$-alkyl,
f) phenyl-$C_{1-2}$-alkylamino-$C_{1-4}$-alkyl,
g) 4–10-membered heterocyclyl-$C_{1-4}$-alkylamino-$C_{1-4}$-alkyl
h) N-(4–10-membered heterocyclyl-$C_{1-4}$-alkyl)amino,
i) $C_{1-4}$-alkyl,
j) $C_{3-6}$-cycloalkyl-$(CH_2)_n$—,
k) aryl-$(CH_2)_n$—,
l) 4–10-membered heterocyclyl-$(CH_2)_n$—,
m) amino-$C_{1-4}$-alkoxy,
n) phenyl-$C_{1-4}$-alkyl where the alkyl portion is substituted with amino, hydroxy or $C_{1-4}$-alkylamino, and
o) 4–10-membered heterocyclyl-$C_{1-4}$-alkylenyl where the alkylenyl portion is substituted with amino, hydroxy or —$C_{1-4}$-alkylamino;

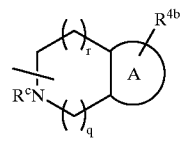

particularly $R^8$ is or azetidinyl; and more particularly

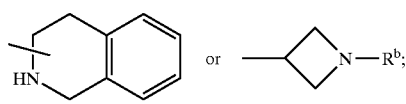

wherein the cycloalkyl and aryl groups are optionally substituted with 1 to 3 groups selected from $R^4$; the heterocyclyl groups are optionally substituted with 1 to 3 groups selected from $R^4$ and oxo; and the alkyl groups are optionally substituted with 1 to 3 groups selected from $R^5$;
wherein the cycloalkyl and aryl groups are optionally substituted with 1 to 3 groups selected from $R^4$; the heterocyclyl groups are optionally substituted with 1 to 3 groups selected from $R^4$ and oxo; and the alkyl groups are optionally substituted with 1 to 3 groups selected from $R^5$;
wherein the cycloalkyl and aryl groups are optionally substituted with 1 to 3 groups selected from $R^4$; and the heterocyclyl groups are optionally substituted with 1 to 3 groups selected from $R^4$ and oxo;
wherein the cycloalkyl and aryl groups are optionally substituted with 1 to 2 groups selected from $R^{4b}$; and the heterocyclyl groups are optionally substituted with 1 to 2 groups selected from $R^{4b}$ and oxo;
wherein $R^{8a}$ is selected from
a) 5–10-membered heterocyclyl,
b) aryl, and
c) benzyl;
wherein the aryl and heterocyclyl groups are optionally substituted with 1 to 3 radicals selected from $C_{1-6}$-alkyl, halo, hydroxyl, alkoxy, amino, alkylamino, cyano, —NHC(O)$R^7$, —CO$R^7$, $C_{1-6}$-haloalkyl and $C_{1-6}$-haloalkoxy;
wherein $R^9$ is selected from H, alkyl, alkenyl, cycloalkyl—$(CH_2)_n$—, heterocyclyl-$(CH_2)_n$—, aryl-$(CH_2)_n$—, aminoalkyl, alkylcarbonylaminoalkyl, cycloalkylaminoalkyl, cycloalkylalkylaminoalkyl, heteroarylaminoalkyl, heteroarylalkylaminoalkyl, arylaminoalkyl, arylalkylaminoalkyl, heteroaryloxyalkyl, heteroarylalkyloxyalkyl, arylalkyloxyalkyl, aryloxyalkyl, alkylthioalkyl, alkylaminoalkyl, hydroxyalkyl and alkoxyalkyl;
preferably H, $C_{1-6}$-alkyl, alkenyl, $C_{3-6}$-cycloalkyl-$(CH_2)_n$—, 4–10-membered heterocyclyl-$(CH_2)_n$—, aryl-$(CH_2)_n$—, amino-$C_{1-6}$-alkyl, $C_{1-6}$-alkylcarbonylamino-$C_{1-6}$-alkyl, $C_{3-6}$-cycloalkylamino-$C_{1-6}$-alkyl, $C_{3-6}$-cycloalkyl-$C_{1-6}$-alkylamino-$C_{1-6}$-alkyl, 5–6-membered heteroarylamino-$C_{1-6}$-alkyl, 5–6-membered heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, 5–6-membered heteroaryloxy-$C_{1-6}$-alkyl, 5–6-membered heteroaryl-$C_{1-6}$-alkyloxy-$C_{1-6}$-alkyl, aryl-$C_{1-6}$-alkyloxy-$C_{1-6}$-alkyl, aryloxy-$C_{1-6}$-alkyl, $C_{1-6}$-alkylthio-$C_{1-6}$-alkyl, $C_{1-6}$-alkylamino-$C_{1-6}$-alkyl, $C_{1-6}$-hydroxyalkyl and $C_{1-6}$-alkoxy-$C_{1-6}$-alkyl;
wherein $R^{9a}$ is selected from H, $C_{1-6}$-alkyl, $C_{3-6}$-cycloalkyl-$(CH_2)_n$—, 4–10-membered heterocyclyl-$(CH_2)_n$— and phenyl-$(CH_2)_n$—; and
preferably H, $C_{1-6}$-alkyl, $C_{5-6}$-cycloalkyl-$(CH_2)_n$—, 4–10-membered heterocyclyl-$(CH_2)_n$—, and phenyl-$(CH_2)_n$—;
wherein $R^{9b}$ is selected from H, $C_{1-6}$-alkyl, $C_{2-6}$-alkenyl, $C_{3-6}$-cycloalkyl-$(CH_2)_n$—, 4–10-membered heterocyclyl-$(CH_2)_n$—, phenyl-$(CH_2)_n$—, amino-$C_{1-6}$-alkyl, $C_{1-6}$-alkylcarbonylamino-$C_{1-6}$-alkyl, $C_{3-6}$-cycloalkylamino-$C_{1-6}$-alkyl, $C_{3-6}$-cycloalkyl-$C_{1-6}$-alkylamino-$C_{1-6}$-alkyl, 5–6-membered heteroarylamino-$C_{1-6}$-alkyl, 5–6-membered heteroaryl-$C_{1-6}$-alkylamino-$C_{1-6}$-alkyl, phenylamino-$C_{1-6}$-alkyl, phenyl-$C_{1-6}$-alkylamino-$C_{1-6}$-alkyl, 5–6-membered heteroaryloxy-$C_{1-6}$-alkyl, 5–6-membered heteroaryl-$C_{1-6}$-alkyloxy-$C_{1-6}$-alkyl, phenyl-$C_{1-6}$-alkyloxy-$C_{1-6}$-alkyl, phenyloxy-$C_{1-6}$-alkyl, $C_{1-6}$-alkylthio-$C_{1-6}$-alkyl, $C_{1-6}$-alkylamino-$C_{1-6}$-alkyl, $C_{1-6}$-hydroxyalkyl and $C_{1-6}$-alkoxy-$C_{1-6}$-alkyl; and preferably H, $C_{1-6}$-alkyl, $C_{5-6}$-cycloalkyl-$(CH_2)_n$—, 4–10-membered heterocyclyl-$(CH_2)_n$—, phenyl-$(CH_2)_n$—, amino-$C_{1-3}$-alkyl, $C_{1-3}$-alkylcarbonylamino-$C_{1-3}$-alkyl, $C_{5-6}$-cycloalkylamino-$C_{1-3}$-alkyl, $C_{5-6}$-cycloalkyl-$C_{1-3}$-alkylamino-$C_{1-3}$-alkyl, 5–6-membered heteroarylamino-$C_{1-3}$-alkyl, 5–6-membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6-membered heteroaryloxy-$C_{1-3}$-alkyl, 5–6-membered heteroaryl-$C_{1-3}$-alkyloxy-$C_{1-3}$-alkyl, phenyl-$C_{1-3}$-alkyloxy-$C_{1-3}$-alkyl, phenyloxy-$C_{1-3}$-alkyl, $C_{1-3}$-alkylthio-$C_{1-3}$-alkyl, $C_{1-3}$-alkylamino-$C_{1-3}$-alkyl, $C_{1-3}$-hydroxyalkyl and $C_{1-3}$-alkoxy-$C_{1-3}$-alkyl;

wherein $R^a$ are independently selected from H, and alkyl or the two $R^a$'s together form cycloalkyl;
preferably H, and $C_{1-6}$-alkyl;
more preferably H or methyl; and
even more preferably $R^a$ are H;
where $R^b$ is selected from H, $C_{1-6}$-alkyl, $C_{5-6}$-cycloalkyl-$(CH_2)_n$—, 4–10-membered heterocyclyl-$(CH_2)_n$- and phenyl-$(CH_2)_n$—;
wherein $R^c$ is H or methyl;
wherein A is selected from phenyl or 5–6-membered heteroaryl;
wherein k is 0 or 1; preferably 1;
wherein m is 0, 1 or 2; preferably 2;
wherein n is 0, 1, 2, 3 or 4; preferably 0, 1, 2 or 3;
wherein p is 1 or 2;
wherein r is 0 or 1; and
wherein q is 0 or 1.

The invention also relates to compounds of Formula II

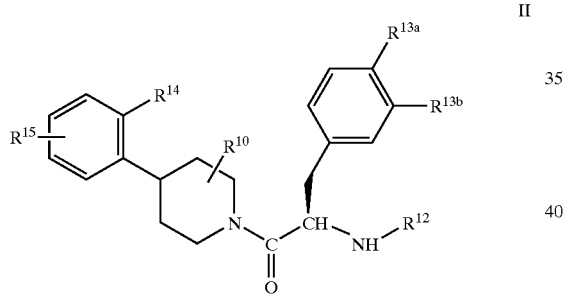

wherein $R^{10}$ is selected from H, chloro or fluoro; or wherein $R^{10}$ is a $C_{1-4}$-alkylene bridge;
preferably H;
wherein $R^{12}$ is selected from optionally substituted phenyl-$C_{1-2}$-alkylenyl, optionally substituted 5–10 membered heteroaryl and

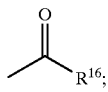

provided the optionally substituted heterocyclyl is not nitro substituted;
preferably

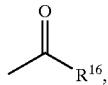

optionally substituted phenyl-$C_{1-3}$-alkyl, and optionally substituted 5–10-membered heterocyclyl;

more preferably oxazolylpyridyl, 4-(N,N-dimethylamino)phenylmethyl, 2,2-dimethyl-oxazolidinyl, benzodioxanylmethyl, pyridylmethyl, indolylmethyl and

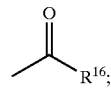

wherein $R^{13a}$ and $R^{13b}$ are independently selected from H, fluoro, iodo, bromo, chloro, $C_{1-2}$-alkyl, $C_{1-2}$-haloalkyl, phenyl, and $C_{1-2}$-alkoxy; or wherein $R^{13a}$ and $R^{13b}$ together form an $C_{1-4}$-alkenylenyl bridge;
preferably $R^{13a}$ is selected from H, bromo, chloro, phenyl, trifluoromethyl and methoxy;
more preferably H and chloro;
preferably $R^{13b}$ is H;
wherein $R^{14}$ is selected from $R^{19}R^{20}N$—, $R^{19}R^{20}N$—$C_{1-4}$-alkyl, ($R^{21}R^{22}N$—)(O=)C—, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;
preferably trifluoromethyl, 2-hydroxyethyl, 1-hydroxyethyl, $R^{19}R^{20}N$—, $R^{19}R^{20}N$—$C_{1-2}$-alkyl and ($R^{21}R^{22}N$—)(O=)C—;
more preferably N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl, 1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-ylmethyl, 2-propylimidazol-1-yl-methyl, 2-oxo-pyrid-1-yl-methyl, 3-pyridyl-oxymethyl, 2-methylimidazol-1-yl-methyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N, N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl, N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'-dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(3-ethylbutyl)aminoethyl)-N-methylsulfonylamino, N-(N',N'-di(cyclopropylmethyl)aminoethyl)-N-methylsulfonylamino, N-(N',N'-di(cyclohexylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6-trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-cyclohexylcarbonyl-N-cyclopropylmethylamino, N-thienylmethylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(4-methyl-5-imidazolylmethyl)-N-cyclopropylmethylamino, N-(4-imidazolylmethyl)-N-cyclopropylmethylamino, N-(5-imidazolylmethyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

wherein $R^{15}$ is selected from H, $C_{1-2}$-haloalkyl, $C_{1-4}$-alkyl, halo, $-OR^{17}$, and $-N(R^{17})_2$;

preferably H and $C_{1-2}$-haloalkyl;

more preferably H or trifluoromethyl;

wherein $R^{16}$ is selected from a) 4–6 membered heterocyclyl, b) 10 membered partially saturated heterocyclyl, c) 5–10 membered heteroaryl, d) $C_{1-4}$-aminoalkyl, e) $C_{1-4}$-aminoalkylamino, f) $C_{1-4}$-alkylamino-$C_{1-4}$-alkylamino, g) $C_{1-4}$-alkylamino-$C_{1-4}$-alkyl, h) arylamino-$C_{1-4}$-alkyl, i) aryl-$C_{1-4}$-alkylamino-$C_{1-4}$-alkyl, j) heterocyclyl-$C_{1-4}$-alkylamino-$C_{1-4}$-alkyl, k) aryl, provided if 2-substituted aryl, is 2-substituted with amino or chloro, l) $C_{1-4}$-alkyl, m) aralkyl, n) heterocyclyl-$C_{1-4}$-alkyl, provided $R^{16}$ is not 3-methylindol-1-ylethyl, o) $C_{5-6}$-cycloalkyl, p) $C_{1-4}$-aminoalkoxy, q) heterocyclyl-$C_{1-4}$-alkoxy, r) N-(heterocyclyl-$C_{1-4}$-alkyl)amino, s) aryl-$C_{1-4}$-alkyl where the alkyl portion is substituted with amino, hydroxy or $-C_{1-4}$-alkylamino, and t) heterocyclyl-$C_{1-4}$-alkylenyl where the alkylenyl portion is substituted with amino, hydroxy or $-C_{1-4}$-alkylamino;

preferably selected from
a) 4–6 membered heterocyclyl,
b) 10 membered partially saturated heterocycyl,
c) 5–10 membered heteroaryl,
d) $C_{1-3}$-aminoalkyl,
e) $C_{1-3}$-aminoalkylamino,
f) $C_{1-3}$-alkylamino-$C_{1-3}$-alkylamino,
g) $C_{1-3}$-alkylamino-$C_{1-3}$-alkyl,
h) phenylamino-$C_{1-3}$-alkyl,
i) phenyl-$C_{1-4}$-alkylamino-$C_{1-3}$-alkyl,
j) heterocyclyl-$C_{1-3}$-alkyamino-$C_{1-3}$-alkyl,
k) phenyl, naphthyl or tetrahydronaphthyl,
l) $C_{1-3}$-alkyl,
m) phenyl-$C_{1-2}$-alkyl,
n) 5–10-membered saturated or partially unsaturated heterocyclylmethyl,
o) optionally substituted 5–6 membered heteroaryl-$C_{1-4}$-alkyl,
p) $C_{5-6}$-cycloalkyl,
q) $C_{1-3}$-aminoalkoxy,
r) [5- or 6-membered heterocyclyl]—$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;
more preferably N-(piperidylmethyl)amino, aminopropylamino, aminomethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl optionally N-substituted with a substituent selected from methyl, ethyl, propyl, isopropyl, butyl, isobutyl, pentyl, cyclohexylmethyl and benzyl;

6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl)methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino)ethyl, imidazol-4-yl-(1-amino)ethyl, phenyl-1-(methylamino)ethyl and phenyl-1-(amino)ethyl;
wherein $R^{17}$ is selected from H, $C_{1-4}$-alkyl, $C_{3-7}$-cycloalkyl-$(CH_2)_n$—, and aryl-$(CH_2)_n$—;
preferably H, $C_{1-3}$-alkyl, —$(CH_2)_n$—$C_{3-6}$-cycloalkyl, and —$(CH_2)_n$-phenyl;
more preferably H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;
wherein $R^{19}$ is selected from H, $R^{23}SO_2$—, $C_{1-6}$alkyl, $C_{3-7}$-cycloalkyl-$(CH_2)_n$—, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkylamino-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;
preferably H, $R^{23}SO_2$—, $C_{3-7}$-alkyl, amino-$C_{1-3}$-alkyl, $C_{1-6}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and —$(CH_2)_n$—$C_{3-5}$-cycloalkyl optionally substituted with $C_{1-2}$-alkoxycarbonyl;
more preferably H, $R^{23}SO_2$—, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-(tert-butylmethyl)aminoethyl, di-(3-ethylbutyl)aminoethyl, di-(cyclohexylmethyl)aminoethyl, furylmethylaminoethyl, thienylmethylaminoethyl, benzylaminoethyl, di(furylmethyl)aminoethyl, di(cyclopropylmethyl)aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, butylcarbonyl, tert-butylcarbonyl, pentylcarbonyl, cyclopentylcarbonyl, cyclopropylcarbonyl, cyclobutylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted thienylmethylcarbonyl, optionally substituted benzylcarbonyl, optionally substituted phenylethylcarbonyl, optionally substituted phenylcarbonyl and optionally substituted pyridylcarbonyl;
wherein $R^{20}$ is selected from H, $C_{1-8}$-alkyl, $C_{3-7}$-cycloalkyl-$(CH_2)_n$—, $C_{1-3}$-alkylsulfonyl, amino-$C_{1-3}$-alkyl, heterocyclyl-$(CH_2)_n$—, and aryl-$(CH_2)_n$—;
preferably H, $C_{1-7}$-alkyl, —$(CH_2)_n$—$C_{5-6}$-cycloalkyl, —$(CH_2)_n$-5–6-membered heterocyclyl, $C_{1-3}$-alkylsulfonyl, amino-$C_{1-3}$-alkyl and —$(CH_2)_n$-phenyl;

more preferably H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted imidazolylmethyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a 4–8 membered heterocyclic ring;
preferably a 4–7 membered heterocyclic ring;
more preferably a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl,
piperidinyl optionally substituted with one or more substituents selected from methyl, ethyl, propyl, and isopropyl,
piperazinyl optionally substituted with one or more substituents selected from methyl, ethyl, propyl, and isopropyl,
imidazolyl optionally substituted with one or more substituents selected from methyl, ethyl, propyl, and isopropyl, and
pyrrolidinyl optionally substituted with one or more substituents selected from methyl, ethyl, propyl, and isopropyl;

wherein $R^{21}$ is selected from H, $C_{1-6}$alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n$—, $C_{3-7}$-cycloalkyl-$(CH_2)_n$—, and aryl-$(CH_2)_n$——;
preferably H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;
more preferably H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is selected from H, $C_{1-6}$-alkyl, —$(CH_2)_n$—$C_{3-7}$-cycloalkyl, —$(CH_2)_N$-heterocyclyl and —$(CH_2)_n$-aryl;
preferably H, $C_{1-3}$-alkyl, —$(CH_2)_n$—$C_{4-6}$-cycloalkyl, —$(CH_2)_n$— [5- or 6-membered heterocyclyl]and —$(CH_2)_n$-phenyl;
more preferably H or methyl;
alternatively $R^{21}$ and $R^{22}$ together with the amide nitrogen atom form a 4–7 membered saturated heterocyclic ring;
preferably a 5–6 membered heterocyclic ring;
more preferably a ring selected from pyrrolidinyl, morpholino, piperidinyl, piperazinyl, 4-acetylpiperazinyl and 4-methylpiperazinyl;

wherein $R^{23}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;
preferably H, $C_{1-3}$-alkyl, —$(CH_2)_n$—$C_{4-6}$-cycloalkyl, —$(CH_2)_n$—[5- or 6-membered heterocyclyl]and —$(CH_2)_n$-phenyl;

more preferably H, methyl, ethyl, propyl, optionally substituted thienyl., optionally substituted phenyl, optionally substituted benzyl, optionally substituted phenylethyl and optionally substituted phenylpropyl;

wherein n is 0, 1, 2 or 3;

wherein m is 0, 1 or 2; and wherein aryl, heterocyclyl and cycloalkyl are optionally substituted with one or more substituents selected from $C_{1-2}$-haloalkyl, $C_{1-3}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_m R^{17}$, and $C_{1-3}$-haloalkoxy;

preferably with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_m R^{17}$, and $C_{1-2}$-haloalkoxy;

more preferably with one or more substituents selected from trifluoromethyl, methyl, nitro, cyano, chloro, methoxy, phenyloxy, acetyl, amino, dimethylamino and aminomethyl.

The invention also relates to compounds of Formula III

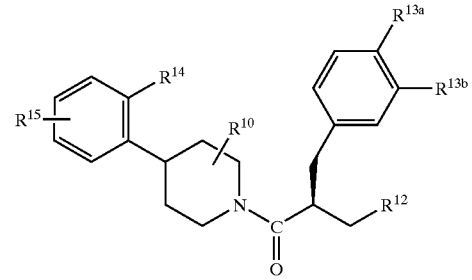

wherein $R^{10}$ is selected from H, chloro or fluoro; or wherein $R^{10}$ is a $C_{1-4}$-alkylene bridge;

preferably H;

wherein $R^{12}$ is selected from optionally substituted phenyl-$C_{1-2}$-alkylenyl, optionally substituted 5–10 membered heteroaryl and

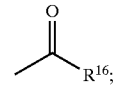

provided the optionally substituted heterocyclyl is not nitro substituted;

preferably

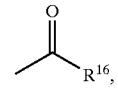

optionally substituted phenyl-$C_{1-9}$-alkyl, and optionally substituted 5–10-membered heterocyclyl;

more preferably oxazolylpyridyl, 4-(N,N-dimethylamino) phenylmethyl, 2,2-dimethyl-oxazolidinyl, benzodioxanylmethyl, pyridylmethyl, indolylmethyl and

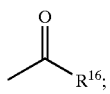

wherein $R^{13}a$ and $R^{13b}$ are independently selected from H, fluoro, iodo, bromo, chloro, $C_{1-2}$-alkyl, $C_{1-2}$-haloalkyl, phenyl, and $C_{1-2}$-alkoxy; or wherein $R^{13a}$ and $R^{13b}$ together form an $C_{1-4}$-alkenylenyl bridge;

preferably $R^{13a}$ is selected from H, bromo, chloro, phenyl, trifluoromethyl and methoxy;
more preferably H and chloro;
preferably $R^{13b}$ is H;

wherein $R^{14}$ is selected from $R^{19}R^{20}N-$, $R^{19}R^{20}N-C_{1-4}$-alkyl, $(R^{21}R^{22}N-)(O=)C-$, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;

preferably trifluoromethyl, 2-hydroxyethyl, 1-hydroxyethyl, $R^{19}R^{20}N-$, $R^{19}R^{20}N-C_{1-2}$-alkyl and $(R^{21}R^{22}N-)(O=)C-$;

more preferably N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl, 1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-yl-methyl, 3-pyridyl-oxymethyl, 2-methylimidazol-1-yl-methyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl, N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'-dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(3-ethylbutyl)aminoethyl)-N-methylsulfonylamino, N-(N',N'-di(cyclopropylmethyl)aminoethyl)-N-methylsulfonylamino, N-(N',N'-di(cyclohexylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6-trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-cyclohexylcarbonyl-N-cyclopropylmethylamino, N-thienylmethylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(4-methyl-5-imidazolylmethyl)-N-cyclopropylmethylamino, N-(4-imidazolylmethyl)-N-cyclopropylmethylamino, N-(5-imidazolylmethyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N- cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

wherein $R^{15}$ is selected from H, $C_{1-2}$-haloalkyl, $C_{1-4}$-alkyl, halo, $-OR^{17}$, and $-N(R^{17})_2$;

preferably H and $C_{1-2}$-haloalkyl;
more preferably H or trifluoromethyl;

wherein $R^{16}$ is selected from
a) 4–6 membered heterocyclyl,
b) 10 membered partially saturated heterocyclyl,
c) 5–10 membered heteroaryl,
d) $C_{1-4}$-aminoalkyl,
e) $C_{1-4}$-aminoalkylamino,
f) $C_{1-4}$-alkylamino-$C_{1-4}$-alkylamino,
g) $C_{1-4}$-alkylamino-$C_{1-4}$-alkyl,
h) arylamino-$C_{1-4}$-alkyl,
i) aryl-$C_{1-4}$-alkylamino-$C_{1-4}$-alkyl,
j) heterocyclyl-$C_{1-4}$-alkylamino-$C_{1-4}$-alkyl,
k) aryl, provided if 2-substituted aryl, is 2-substituted with amino or chloro,
l) $C_{1-4}$-alkyl,
m) aralkyl,
n) heterocyclyl-$C_{1-4}$-alkyl, provided $R^{16}$ is not 3-methylindol-1-ylethyl,
o) $C_{5-6}$-cycloalkyl,
p) $C_{1-4}$-aminoalkoxy,
q) heterocyclyl-$C_{1-4}$-alkoxy,
r) N-(heterocyclyl-$C_{1-4}$-alkyl)amino,
s) aryl-$C_{1-4}$-alkyl where the alkyl portion is substituted with amino, hydroxy or $-C_{1-4}$-alkylamino, and
t) heterocyclyl-$C_{1-4}$-alkylenyl where the alkylenyl portion is substituted with amino, hydroxy or $-C_{1-4}$-alkylamino;
preferably selected from
a) 4–6 membered heterocyclyl,
b) 10 membered partially saturated heterocyclyl,
c) 5–10 membered heteroaryl,
d) $C_{1-3}$-aminoalkyl,
e) $C_{1-3}$-aminoalkylamino,
f) $C_{1-3}$-alkylamino-$C_{1-3}$-alkylamino,
g) $C_{1-3}$-alkylamino-$C_{1-3}$-alkyl,
h) phenylamino-$C_{1-3}$-alkyl,
i) phenyl-$C_{1-4}$-alkylamino-$C_{1-3}$-alkyl,
j) heterocyclyl-$C_{1-3}$-alkylamino-$C_{1-3}$-alkyl,
k) phenyl, naphthyl or tetrahydronaphthyl,
l) $C_{1-3}$-alkyl,
m) phenyl-$C_{1-2}$-alkyl,
n) 5–10-membered saturated or partially unsaturated heterocyclylmethyl,
o) 5–6 membered heteroaryl-$C_{1-4}$-alkyl,
p) $C_{5-6}$-cycloalkyl,
q) $C_{1-3}$-aminoalkoxy,
r) [5- or 6-membered heterocyclyl]-$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;
more preferably N-(piperidylmethyl)amino, aminopropylamino, aminomethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl
optionally N-substituted with a substituent selected from methyl, ethyl, propyl, isopropyl, butyl, isobutyl, pentyl, cyclohexylmethyl and benzyl,
6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl)methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino)ethyl, imidazol-4-yl-(1-amino)ethyl, phenyl-1-(methylamino)ethyl and phenyl-1-(amino)ethyl;

wherein $R^{17}$ is selected from H, $C_{1-4}$alkyl, $C_{3-7}$-cycloalkyl-$(CH_2)_n-$, and aryl-$(CH_2)_n-$;

preferably H, $C_{1-3}$-alkyl, $-(CH_2)_n-C_{3-6}$-cycloalkyl, and $-(CH_2)_n$-phenyl;

more preferably H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;

wherein $R^{19}$ is selected from H, $R^{23}SO_2$—, $C_{1-6}$-alkyl, $C_{3-7}$-cycloalkyl-$(CH_2)_n$—, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;

preferably H, $R^{21}SO_2$—, $C_{1-6}$-alkyl, amino-$C_{1-3}$-alkyl, $C_{1-6}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and —$(CH_2)_n$—$C_{3-5}$-cycloalkyl optionally substituted with $C_{1-2}$-alkoxycarbonyl;

more preferably H, $R^{23}SO_2$—, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-(tert-butylmethyl)aminoethyl, di-(3-ethylbutyl)aminoethyl, di-(cyclohexylmethyl)aminoethyl, furylmethylaminoethyl, thienylmethylaminoethyl, benzylaminoethyl, di(furylmethyl)aminoethyl, di(cyclopropylmethyl)aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, butylcarbonyl, tert-butylcarbonyl, pentylcarbonyl, cyclopentylcarbonyl, cyclopropylcarbonyl, cyclobutylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted thienylmethylcarbonyl, optionally substituted benzylcarbonyl, optionally substituted phenylethylcarbonyl, optionally substituted phenylcarbonyl and optionally substituted pyridylcarbonyl;

wherein $R^{20}$ is selected from H, $C_{1-8}$-alkyl, $C_{3-7}$-cycloalkyl-$CH_2)_n$—, $C_{1-3}$-alkylsulfonyl, amino-$C_{1-3}$-alkyl, heterocyclyl-$CH_2)_n$, and aryl-$(CH_2)_n$—;

preferably H, $C_{1-7}$-alkyl, —$(CH_2)_n$—$C_{5-6}$-cycloalkyl, —$(CH_2)_n$-5-6-membered heterocyclyl, $C_{1-3}$-alkylsulfonyl, amino-$C_{1-3}$-alkyl and —$(CH_2)_n$-phenyl;

more preferably H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted imidazolylmethyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a 4–8 membered heterocyclic ring;

preferably a 4–7 membered heterocyclic ring;

more preferably a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally substituted with one or more substituents selected from methyl, ethyl, propyl, and isopropyl, piperazinyl optionally substituted with one or more substituents selected from methyl, ethyl, propyl, and isopropyl, imidazolyl optionally substituted with one or more substituents selected from methyl, ethyl, propyl, and isopropyl, and pyrrolidinyl optionally substituted with one or more substituents selected from methyl, ethyl, propyl, and isopropyl;

wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n$—, $C_{3-7}$-cycloalkyl-$(CH_2)_n$—, and aryl-$(CH_2)_n$—;

preferably H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;

more preferably H, methyl, ethyl, propyl, isopropyl, allyl, methylthioethyl, methylthiomethyl, methylcarbonylaminoethyl, methlylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$— [5- or 6-membered heterocyclyl]and —$(CH_2)_n$-phenyl;

more preferably H or methyl;

alternatively $R^{21}$ and $R^{22}$ together with the amide nitrogen atom form a 4–7 membered saturated heterocyclic ring;

preferably a 5–6 membered heterocyclic ring;

more preferably a ring selected from pyrrolidinyl, morpholino, piperidinyl, piperazinyl, 4-acetylpiperazinyl and 4-methylpiperazinyl;

wherein $R^{23}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$— [5- or 6-membered heterocyclyl) and —$(CH_2)_n$-phenyl;

more preferably H, methyl, ethyl, propyl, optionally substituted thienyl, optionally substituted phenyl, optionally substituted benzyl, optionally substituted phenylethyl and optionally substituted phenylpropyl;

wherein n is 0, 1, 2 or 3;
wherein m is 0, 1 or 2; and
wherein aryl, heterocyclyl are optionally substituted with one or more substituents selected from $C_{1-2}$-haloalkyl, $C_{1-3}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-3}$-haloalkoxy;

preferably with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$—$NR^{17}SO_2R^{17}$, $(R^{17})_2$, cyano, —$COR^{17}$—$C(R^{17})_2N(R^{17})_2$, nitro, —$SO_2N(R^{17})_2$, —$S(O)_nR^{17}$, and $C_{1-2}$-haloalkoxy;

more preferably with one or more substituents selected from trifluoromethyl, methyl, nitro, cyano, chloro, methoxy, phenyloxy, acetyl, amino, dimethylamino and aminomethyl.

Indications

Compounds of the present invention would be useful for, but not limited to, the prevention or treatment of obesity and obesity-related diseases. The compounds of the invention have MCR agonist activity, including MCR4 agonist activity.

Compounds of formula I are MCR agonists and as such are useful in the treatment, control or prevention of diseases, disorders or conditions responsive to the activation of one or more of the MCRs including, but are not limited to, MCR1, MCR2, MCR3, MCR4, and/or MCR5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunomodulation, rheumatoid arthritis, skin tanning, acne and other skin disorders, neuroprotective and cognitive and memory enhancement including the treatment of Alzheimer's disease.

Other conditions that can be treated with the MC receptor agonists of the invention include, but are not limited to, disuse deconditioning; organ damage such as occurs in response to organ transplantation or ischemic injury such as that which can occur after reperfusion or stroke; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas' Disease.

Another aspect of the present invention provides a method for the treatment or prevention of obesity or diabetes in a mammal which comprises administering to said mammal an effective amount of a compound of Formulas I–III. Compounds of the present invention also are useful as G-protein agonists.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

As used herein, the terms "regulate" or "regulatory" mean to control by enhancing, limiting, restricting, restraining, modulating or moderating. Such regulation includes the pleiotropic, redundant, synergistic or antagonistic effects that occur due to the activity of biological agents such as cytokines, which can affect a variety of biological functions directly or indirectly through cascade or biofeedback mechanisms.

The term "prevention" includes either preventing the onset of disorders altogether or delaying the onset of a pre-clinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

As used herein, "MCR4 agonist" and "MCR3 agonist" refers to a compound with affinity for MCR4 or MCR3, respectively, that results in measurable biological activity in cells, tissues, or organisms which contain MCR4 or MCR3.

As used herein, "MCR3" and "MCR4" mean the known MCR3 and MCR4 receptors, their splice variants, and undescribed receptors. MCR3 is described by Gantz et al., supra (human MCR3), Desarnaud et al., supra (mouse MCR3) and L. Reyfuss et al., Proc. Natl. Acad. Sci. USA, 90, 8856–8860 (1993) (rat MCR3). MCR4 receptors are described by Gantz et al., supra (human MCR4), J. D. Alvaro et al., Mol. Pharmacol., 50, 583–91 (1996) (rat MCR4) and Takeuchi, S. and Takahashi, S., Gen-Comp-Endocrinol., 112(2), 220–31 (1998) (chicken MCR4).

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. The term "impotence" is oftentimes employed to describe this condition.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl(—$CH_2$—) and ethylenyl(—$CH_2CH_2$—).

The term "alkenyl" embraces linear or branched radicals of two to about twelve carbon atoms having at least one carbon-carbon double bond More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having two to about twelve carbon atoms having at least one carbon carbon triple bond. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with one or more halo radicals as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms.

Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocyclyl" also includes bridged heterocyclic groups, having 5–8 members. Examples of such radicals include 8-aza-bicyclo[3.2.1]octyl, 7-aza-bicyclo[2.2.1]heptyl, 5-aza-bicyclo[2.1.1]hexyl, and the like. Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The term "alkylsulfonyl" embraces sulfonyl radicals substituted with an alkyl radical. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, and ethylsulfonyl.

The terms "sulfamyl," "aminosulfonyl" and "sulfonamidyl," denotes a sulfonyl radical substituted with an amine radical, (—$SO_2NH_2$).

The term "alkylaminosulfonyl" includes "N-alkylaminosulfonyl" where sulfonyl radicals are substituted with one or two alkylamino radical(s). More preferred alkylaminosulfonyl radicals are "lower alkylaminosulfonyl" radicals having alkyl portions of one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The term "alkoxycarbonyl" denotes an ester group, where a carbonyl radical is substituted with an alkoxy radical. More preferred are "lower alkoxycarbonyl" having lower alkoxy radicals as described above attached to a carbonyl radical.

The terms "N-alkylaminocarbonyl" and "N,N-dialkylaminocarbonyl" denote aminocarbonyl radicals substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkylenyl radicals are "5- or 6-membered heterocyclylalkylenyl" radicals having alkyl portions of one to six carbon atoms and a 5- or 6-membered heterocyclyl radical. Similarly, "heteroarylalkylenyl" and "heteroarylalkyl" embrace heteroaryl-substituted alkyl radicals. Even more preferred are lower heteroarylalkylenyl radicals having alkyl portions of one to three carbon atoms. Examples include such radicals as pyridylmethyl and thienylmethyl.

The terms "aralkyl" and "arylalkyl" embrace aryl-substituted alkyl radicals. Preferable aralkyl radicals are "lower aralkyl" having aryl radicals attached to alkyl radicals having one to six carbon atoms. Even more preferred are "phenylalkylenyl" having alkyl portions of one to three carbon atoms. Examples of such radicals include benzyl, diphenylmethyl and phenylethyl. The aryl in said aralkyl may be additionally substituted, such as with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "alkylthioalkyl" embraces radicals containing a alkylthio radical, of one to ten carbon atoms, attached to a linear or branched alkyl radical of one to about ten carbon atoms. Even more preferred are lower alkthioalkyl radicals, where each alkyl portion contains one to six carbon atoms. An example of "alkthioalkyl" is meththiomethyl ($CH_3SCH_2$—).

The term "alkoxyalkyl" embrace radicals containing an alkoxy radical, of one to about ten carbon atoms, attached to a linear or branched alkyl radical of one to about ten carbon atoms. More preferred alkoxyalkyl radicals are "lower alkoxyalkyl", radicals having alkyl portions each with one to six carbon atoms. Examples of such radicals include methoxyethyl, ethoxymethyl, methoxymethyl, and the like. Even more preferred are lower alkoxyalkyl radicals where each alkyl portion has one to three carbon atoms.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "aminoalkylamino" embraces aminoalkyl radicals having one to about ten carbon atoms any one of which are substituted on an amino radical. More preferred aminoalkylamino radicals are "lower aminoalkylamino" radicals having one to six carbon atoms. Examples of such radicals include aminomethylamino, aminoethylamino, aminopropylamino and aminobutylamino. Even more preferred are lower aminoalkylamino radicals having one to three carbon atoms.

The term "aminoalkoxy" embraces alkoxy radicals having one to about ten carbon atoms any one of which may be substituted with one or more amino radicals. More preferred aminoalkoxy radicals are "lower aminoalkoxy" radicals having one to six carbon atoms and one or more amino radicals. Examples of such radicals include aminomethoxy, and aminopropoxy. Even more preferred are lower aminoalkoxy radicals having one to three carbon atoms.

The term "alkylcarbonylaminoalkyl" embraces aminoalkyl radicals which are substituted with an alkylcarbonyl radical. More preferred alkylcarbonylaminoalkyl radicals are "lower alkylcarbonylaminoalkyl" radicals having alkyl portions each containing one to six carbon atoms. Examples of such radicals include methylcarbonylmethylamino, and the like. Even more preferred are lower alkylcarbonylaminoalkyl radicals having alkyl portions each containing one to three carbon atoms.

The term "alkylcarbonyl" denotes carbonyl groups which have been substituted with an alkyl radical. More preferred are $C_1$–$C_6$-alkylcarbonyl radicals, such as methylcarbonyl, ethlcarbonyl and propylcarbonyl.

The term "alkoxyalkylcarbonyl" denotes alkylcarbonyl groups which have been substituted with one or more alkoxy radicals. More preferred are $C_1$–$C_6$-alkoxy-$C_1$–$C_6$-alkylcarbonyl radicals, such as methoxymethylcarbonyl, and the like.

The tern "arylcarbonyl" denotes carbonyl groups which have been substituted with aryl radicals, such as phenylcarbonyl. The arylcarbonyl radicals may be further substituted on the aryl ring portion of the radical.

The term "heteroarylcarbonyl" denotes carbonyl groups which have been substituted with a heteroaryl radical, such as thienylcarbonyl. The "heteroarylcarbonyl" radicals may be further substituted on the heteroaryl ring portion of the radical.

The terms "aralkylcarbonyl" and "arylalkylcarbonyl" denote carbonyl groups which have been substituted with aralkyl radicals. More preferred are phenyl-$C_1$–$C_3$-alkylcarbonyl radicals, such as benzylcarbonyl. The aralkylcarbonyl radicals may be further substituted on the aryl ring portion.

The term "heterocyclylalkylcarbonyl" denotes carbonyl groups which have been substituted with heterocyclylalkyl radicals. More preferred are heterocyclyl-$C_1$–$C_3$-alkylcarbonyl radicals, such as thienylmethylcarbonyl, and the like. The "heterocyclylalklylcarbonyl" radicals may be further substituted on the heterocyclyl ring portion of the radical.

The term "heteroarylalklcarbonyl" denotes carbonyl groups which have been substituted heteroarylalkyl radicals. More preferred are heteroaryl-$C_1$–$C_3$-alkylcarbonyl radicals, such as pyridylmethylcarbonyl, and the like. The "heteroarylalklylcarbonyl" radicals may be further substituted on the heteroaryl ring portion of the radical.

The term "cycloalkylcarbonyl" denotes carbonyl groups which have been substituted with cycloalkyl radicals, such as cyclopropylcarbonyl. More preferred contain $C_3$–$C_6$ cycloalkyl radicals. The "cycloalkylcarbonyl" radicals may be further substituted on the cycloalkyl ring portion of the radical.

The term "cycloalkylalkylcarbonyl" denotes carbonyl groups which have been substituted with cycloalkylalkyl radicals. More preferred are $C_3$–$C_6$ cycloalkyl-$C_1$–$C_3$-alkylcarbonyl radicals, such as cyclpentylmethylcarbonyl. The cycloalkylalkylcarbonyl radicals may be further substituted on the aryl ring portion.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl, such as N-methylaminomethyl, N,N-dimethylaminoethyl, N,N-diethylaminomethyl and the like.

The term "alkylaminoalkylamino" embraces alkylamino radicals substituted with alkylamino radicals. More preferred alkylaminoalkylamino radicals are "lower alkylaminoalkylamino" radicals having alkyl radicals of one to six carbon atoms. Even more preferred are radicals having alkyl radicals of one to three carbon atoms. Suitable alkylaminoalkylamino radicals may be mono or dialkyl, such as N-methylaminomethylamino, N,N-dimethylaminoethylamino, N,N-diethylaminomethylamino or the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms, attached to a amino group. Even more preferred are lower alkylamino radicals having alkyl radicals of one to three carbon atoms. Suitable alkylamino radicals may be mono or dialkylamino such as N-methylaminomethyl, N,N-dimethylaminoethyl, N,N-diethylaminomethyl or the like.

The term "cycloalkylaminoalkyl" denotes aminoalkyl groups which have been substituted with one or two cycloalkyl radicals. More preferred are $C_3$–$C_6$-cycloalkylamino-$C_1$–$C_3$-alkyl radicals, such as N-cyclohexylmethylaminomethyl. The cycloalkylalkylaminoalklyl radicals may be further substituted on the cycloalkyl ring portion of the radical.

The term "cycloalkylalkylaminoalkyl" denotes aminoalkyl groups which have been substituted with one or two cycloalkylalkyl radicals. More preferred are $C_3$–$C_6$-cycloalkyl-$C_1$–$C_3$-alkylamino-$C_1$–$C_3$-alkyl radicals, such as N-cyclohexylmethylaminomethyl. The cycloalkylalkylaminoalkyl radicals may be further substituted on the cycloalkyl ring portion.

The terms "aralkylamino" and "arylalkylamino" denote amino groups which have been substituted with one or two aralkyl radicals. More preferred are phenyl-$C_1$–$C_3$-alkylamino radicals, such as N-benzylamino. The aralkylamino radicals may be further substituted on the aryl ring portion.

The term "heterocyclylalkylamino" denotes amino groups which have been substituted with one or two heterocyclylalkyl radicals. More preferred include heterocyclyl-$C_1$–$C_3$-alkylamino, such as N-thienylmethylamino, and the like. The "heterocyclylalklylamino" radicals may be further substituted on the heterocyclyl ring portion of the radical.

The term "heteroarylalkylamino" denotes amino groups which have been substituted with one or two heteroarylalkyl radicals. More preferred are heteroaryl-$C_1$–$C_3$-alkylamino, such as N-thienylmethylamino, and the like. The "heteroarylalklylamino" radicals may be further substituted on the heteroaryl ring portion of the radical.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "arylaminoalkyl" denotes aminoalkyl groups which have been substituted with one or two aryl radicals. More preferred are arylamino-$C_1$–$C_3$-alkyl radicals, such as N-phenylaminomethyl. The arylaminoalkyl radicals may be further substituted on the aryl ring portion of the radical.

The term "heteroarylaminoalkyl" denotes aminoalkyl groups which have been substituted with one or two heteroaryl radicals. More preferred are heteroarylamino-$C_1$–$C_3$-alkyl radicals, such as N-thienylaminomethyl. The "heteroarylaminoalkyl" radicals may be further substituted on the heteroaryl ring portion of the radical.

The terms "aralkylaminoalkyl" and "arylalkylaminoalkyl" denote aminoalkyl groups which have been substituted with one or two aralkyl radicals. More preferred are phenyl-$C_1$–$C_3$-alkylamino-$C_1$–$C_3$-alkyl radicals, such as N-benzylaminomethyl. The aralkylaminoalkyl radicals may be further substituted on the aryl ring portion.

The term "arylthio" embraces aryl radicals of six to ten carbon atoms, attached to a divalent sulfur atom. An example of "arylthio" is phenylthio. The aryl portion may be further substituted.

The term "aralkylthio" embraces aralkyl radicals as described above, attached to a divalent sulfur atom. More preferred are phenyl-$C_1$–$C_3$-alkylthio radicals. An example of "aralkylthio" is benzylthio. The aryl portion may be further substituted.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above. The aryl portion may be further substituted.

The term "heteroaryloxy" embraces optionally substituted heteroaryl radicals, as defined above, attached to an oxygen atom.

The term "heteroarylalkoxy" embraces heteroarylalkyl radicals attached through an oxygen atom. More preferred heteroarylalkoxy radicals are "lower heteroarylalkoxy" radicals having optionally substituted heteroarylalkyl radicals attached to lower alkoxy radical as described above.

The term "aryloxyalkyl" embraces radicals containing an aryloxy radical attached to a linear or branched alkyl radical of one to about ten carbon atoms. More preferred aryloxyalkyl radicals are "lower phenyloxyalkyl" radicals having alkyl portions of one to six carbon atoms. Examples of such radicals include phenoxyethyl, phenoxymethyl, and the like. Even more preferred are lower aryloxyalkyl radicals having alkyl portions of one to three carbon atoms.

The term "heteroaryloxyalkyl" embraces radicals containing an heteroaryloxy radical attached to a linear or branched alkyl radical of one to about ten carbon atoms. More preferred heteroaryloxyalkyl radicals are "lower heteroaryloxyalkyl" radicals having alkyl portions of one to six carbon atoms. Examples of such radicals include pyridyloxyethyl, and the like. Even more preferred are lower heteroaryloxyalkyl radicals having alkyl portions of one to three carbon atoms.

The term "heteroarylalkyloxyalkyl" embraces radicals containing an heteroarylalkyloxy radical attached to a linear or branched alkyl radical of one to about ten carbon atoms. More preferred heteroarylalkyloxyalkyl radicals are "lower heteroarylalkyloxyalkyl" radicals having alkyl portions of one to six carbon atoms. Examples of such radicals include pyridylmethyloxymethyl, and the like. Even more preferred are lower heteroarylalkyloxyalkyl radicals having alkyl portions of one to three carbon atoms.

The term "aralkyloxyalkyl" embraces radicals containing an aralkyloxy radical attached to a linear or branched alkyl radical of one to about ten carbon atoms. More preferred aralkyloxyalkyl radicals are "lower phenylalkyloxyalkyl" radicals having alkyl portions of one to six carbon atoms each. Examples of such radicals include benzyloxyethyl, phenylethyloxymethyl, and the like. Even more preferred are lower aralkyloxyalkyl radicals having alkyl portions of one to three carbon atoms each.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "comprising" is meant to be open ended, including the indicated component but not excluding other elements.

The present invention preferably includes compounds that are agonists of the melanocortin-4 receptor.

The present invention also comprises the use of a compound of the invention, or pharmaceutically acceptable salt thereof, in the manufacture of a medicament for the treatment either acutely or chronically of an obesity mediated disease state, including those described previously. The compounds of the present invention are useful in the manufacture of an anti-obesity medicament. The compounds of the present invention are also useful in the manufacture of a medicament to attenuate or prevent disorders through antagonism of melanocortin receptor.

The present invention comprises a pharmaceutical composition comprising a therapeutically-effective amount of a compound of Formulas I–III in association with a least one pharmaceutically-acceptable carrier, adjuvant or diluent.

The present invention also comprises a method of treating obesity related disorders, in a subject, the method comprising treating the subject having or susceptible to such disorder with a therapeutically-effective amount of a compound of Formulas I–III.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

If formulated as a fixed dose, such combination products employ the compounds of this invention within the accepted dosage ranges. Compounds of Formula I may also be administered sequentially with known agents when a combination formulation is inappropriate. The invention is not limited in the sequence of administration; compounds of formula I–III may be administered either prior to or after administration of the known agents.

Specifically, the administration of compounds of the present invention may be in conjunction with additional antiobesity agents or appetite regulating agents, therapies known to those skilled in the art.

Such agents may be selected from the group consisting of CART (cocaine amphetamine regulated transcript) agonists, NPY (neuropeptide Y) antagonists, MC4 (melanocortin-4) agonists, orexin antagonists, TNF (tumor necrosis factor) agonists, CRF (corticotropin releasing factor) agonists, CRF BP (corticotropin releasing factor binding protein) antagonists, urocortin agonists, P3 agonists, IVISH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators or TR P agonists.

Specifically such agents include leptin, topiramate, bupropion, dexamphetamine or amphetamine, fenfluramine, dexfenfluramine or sibutramine, orlistat, mazindol or phentermine.

Furthermore, the present compounds may be administered in combination with one or more anti hypertensive agents. Examples of anti-hypertensive agents are P-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazern and verapamil, and a-blockers such as doxazosin, urapidil, prazosin and terazosin, insulin sensitizers including PPARy agonists [such as the glitazones (e.g. troglitazone, ploglitazone, englitazone, MCC-555, BRL49653 and the like)]and biguanides such as metformin and phenformin, insulin or insulin mimetics, sulfonylureas such as tolbutamide and glipizide, glucosidase inhibitors (such as acarbose), cholesterol lowering agents such as [HMG-CoA reductase inhibitors (lovastatin, slmvastatin and pravastatin, fluvastatin, atorvastatin, and other statins), sequestrants (cholestyramine, colestipol and a dialkylaminoalkyl derivatives of a cross-linked dextran), nicotinyl alcohol nicotinic acid or a salt thereof, proliferator-activater receptor (x agonists such as fenofibric acid derivatives (gemfibrozil, clofibrate, fenofibrate and benzafibrate), inhibitors of cholesterol absorption for example beta-sitosterol and (acyl CoA:cholesterol acyltransferase) inhibitors for example melinamide, probucol, vitamin E, and thyromimetics[PPAR8 agonists, antiobesity compounds such as fenfluramine, dexfenfluramine, phentermine, sibutramine, orlistat, or P3 adrenergic receptor agonists, feeding behavior modifying agents such as neuropeptide Y antagonists (e.g. neuropeptide Y5), PPARu, agonists by Glaxo, PPARY antagonists, serotonin reuptake inhibitors such as fluoxetine and sertraline, growth hormone secretagogues such as MK-0677; and agents useful in the treatment of male and/or female sexual dysfunction which include phosphodiesterase V (PDE-V) inhibitors, such as sildenafil and IC-351; (x2-adrenergic receptor antagonists, such as phentolamine mesylate; and dopamine-receptor agonists, such as apomorphine. Further reference can be made to Remington: The Science and Practice of Pharmacy, 19th Edition, Gennaro, Ed., Mack Publishing Co., Easton, Pa., 1995.

The present invention comprises a process for the preparation of a compound of Formula I–III.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I–III.

Also included in the family of compounds of Formula I–III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 82-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I–III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Additional examples of such salts can be found in Berge et al., J. Pharm. Sci., 66, 1 (1977).

General Synthetic Procedures

The compounds of the invention can be synthesized according to the following procedures of Schemes 1–16, wherein the substituents are as defined for Formulas I–III, above, except where further noted.

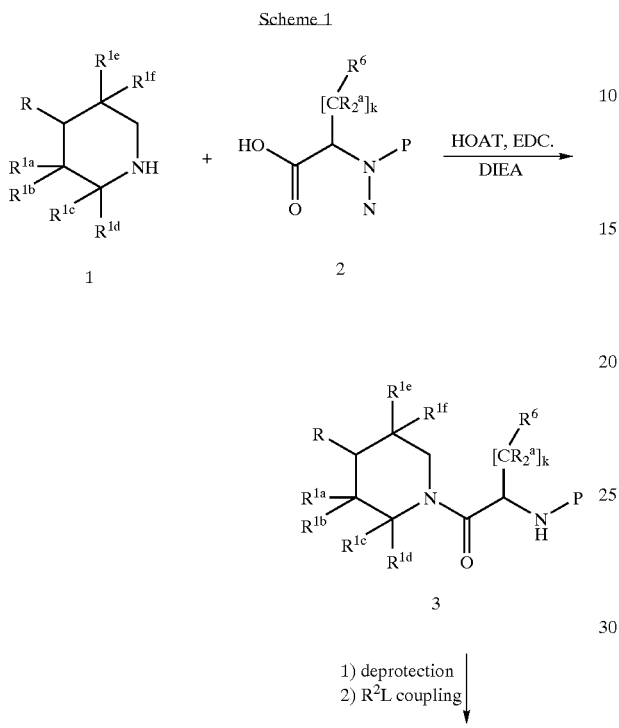

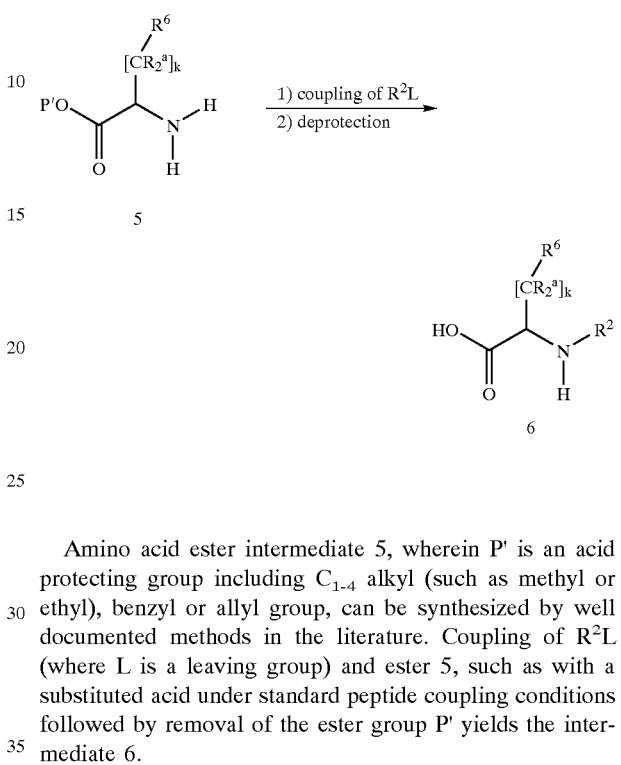

Amino acid ester intermediate 5, wherein P' is an acid protecting group including $C_{1-4}$ alkyl (such as methyl or ethyl), benzyl or allyl group, can be synthesized by well documented methods in the literature. Coupling of $R^2L$ (where L is a leaving group) and ester 5, such as with a substituted acid under standard peptide coupling conditions followed by removal of the ester group P' yields the intermediate 6.

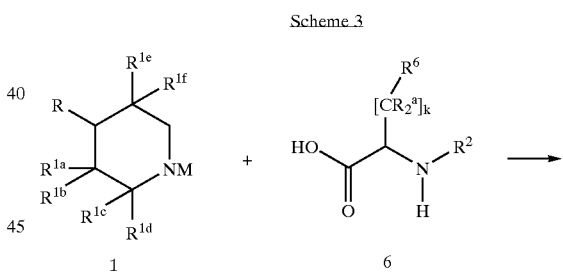

Compounds of Formula I may be prepared in a convergent manner as described in Scheme 1. Protected amino acids 2 (where P is a protecting group) are coupled with the substituted piperazine 1 using standard peptide coupling conditions, such as with HOAT EDC, and DIEA in a solvent, such as $MeCl_2$, and reacted at RT, to afford the protected piperazine amino acid 3. The protected amino acid derivatives 2 are commercially available or may be prepared by literature methods (R. M. Williams, Synthesis of Optically Active α-Amino Acids, Pergamon Press: Oxford, 1989). Similarly, substituted piperazines 1 are either commercially available, can be prepared via literature methods, or may be prepared following literature methods described for analogous compounds. Some of these methods are illustrated in the subsequent schemes. Removal of the protecting group P (CBZ, BOC, etc.) is accomplished using conventional methods, such as with a solution of 50% TFA and $CH_2Cl_2$ to remove a Boc group, to yield the free amine. The free amine is treated with base, such as DIEA in a solvent, such as $MeCl_2$. The reaction mixture is coupled with $R^2L$, such as a substituted acid using standard peptide coupling conditions, such as with HOAT, EDC, and DIEA in a solvent, at a temperature such as of about RT, to yield the desired compound 4.

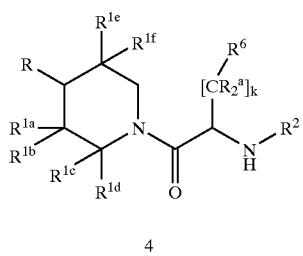

Compounds of Formula I may also be prepared in a convergent manner as described in Scheme 3. Compounds 4 are obtained by coupling intermediates 6 to piperidines 1 under standard peptide coupling reaction conditions.

Scheme 4

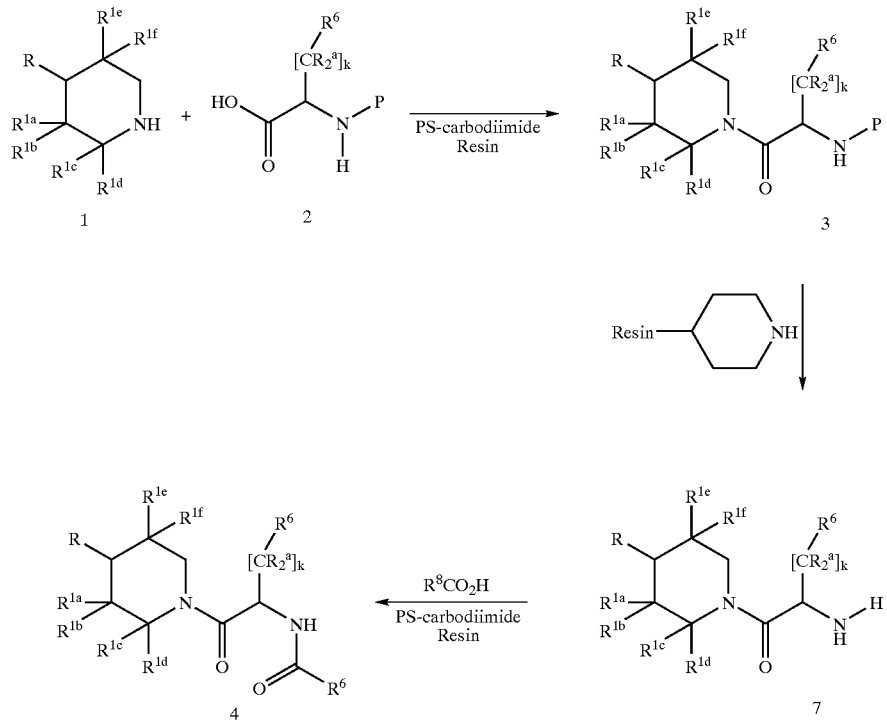

Chemical libraries can be made using variations of the above described chemistry to make compounds of Formula I, where $R^2$ is —C(=O)$R^8$, as described in Scheme 4. Piperazine 1 is added to PS-carbodiimide resin, and an FMOC protected amino acid. Excess piperazine 1 is scavenged, such as with PS-isocyanate resin. The reaction mixture is filtered into scintillation vials containing DMAP and piperidine-4-carboxylic acid polyamine resin HL. PS-carbodiimide resin and $R^8CO_2H$ are added. The reactions are filtered and excess amine is scavenged, such as with PS-isocyanate resin. The compounds are deprotected if needed to yield compounds 4. Other conditions and resins known to one skilled in the art can be used.

Scheme 5

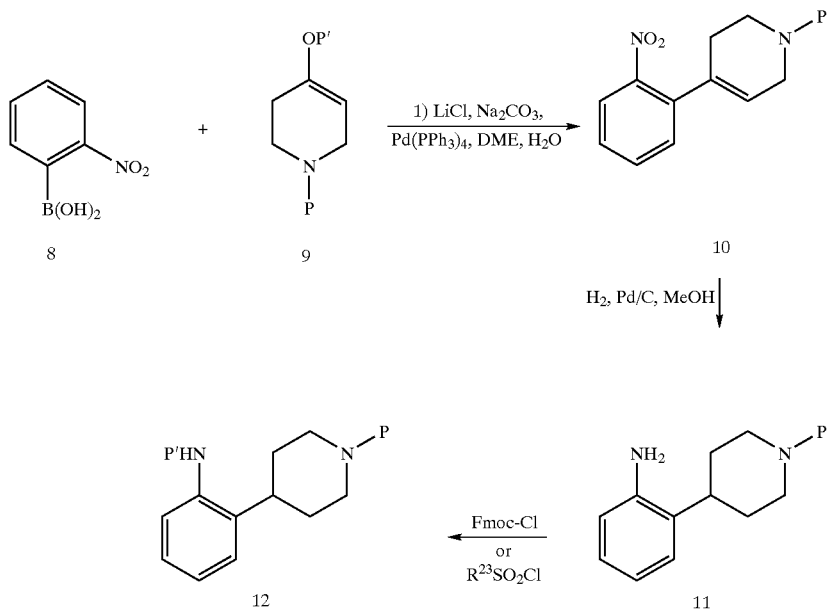

Substituted piperidines can be prepared such as by the method described in Scheme 5. Nitrophenyl boronic acids 8 are coupled with a protected tetrahydropyridines 9 such as with LiCl, and a catalyst, such as tetrakis (triphenylphosphine)palladium(0) in the presence of base, such as Na$_2$CO$_3$, at a temperature above RT, preferably above about 75° C., even more preferably at about 90° C., to yield the nitrophenylpiperidine 10. The nitrophenylpiperidine 10 is converted to the amine 11, such as hydrogenation with H$_2$ and Pd/C. The amine 11 is protected (where treated with FMOC) or substituted to form the sulfonamide 12 (where treated with the sulfonyl chloride), at a temperature above RT, preferably at about 50° C.

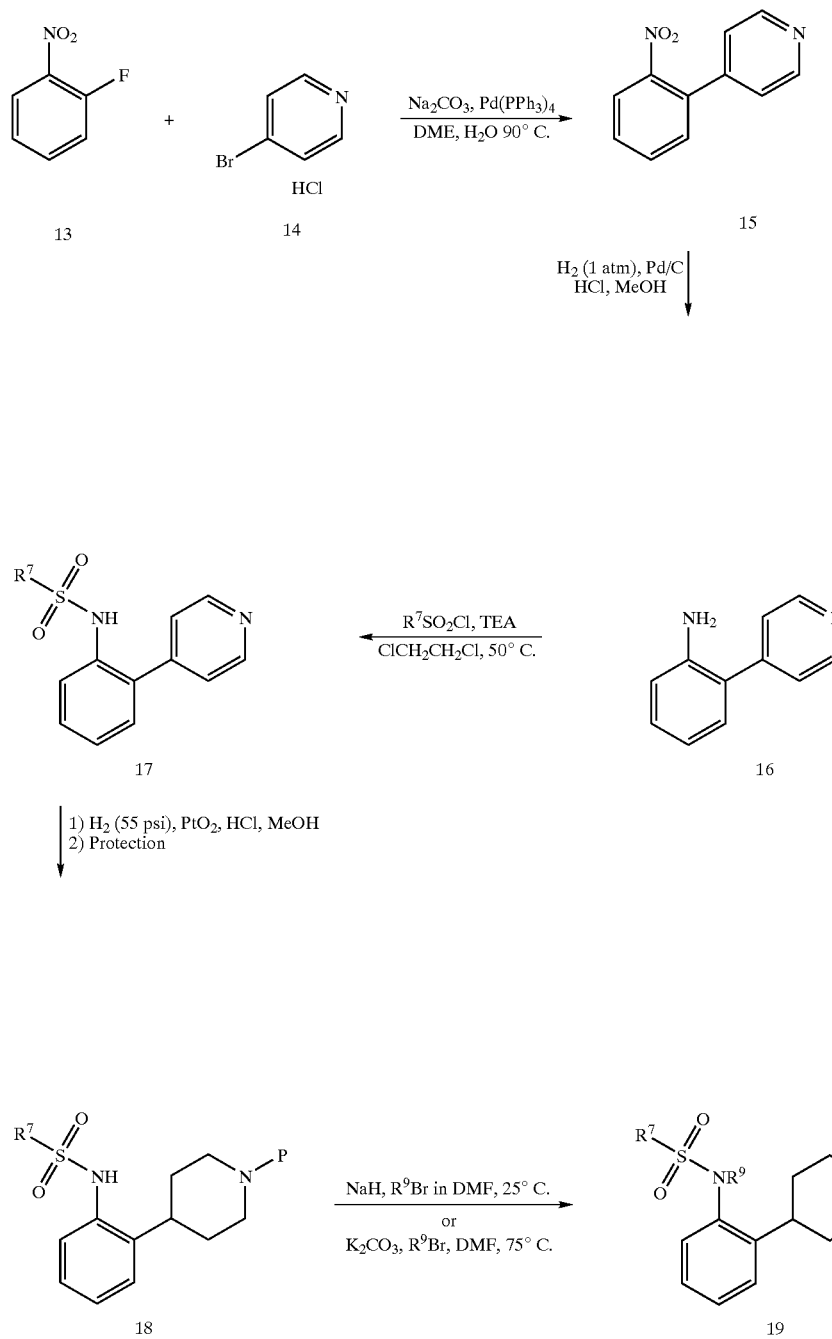

Scheme 6

Substituted piperidines also can be prepared such as by the method described in Scheme 6. 2-Fluoronitrobenzene 13, is coupled with 4-bromopiperidine 14 such as with base, and a catalyst, such as Pd(PPh)$_3$ to yield the nitrophenylpyridine 15. The nitro compound 15 is reduced to form the amine 16, such as with hydrogenation with H$_2$ in the presence of catalyst, such as Pd/C. The amine 16 is treated with base, such as TEA (Aldrich) and a substituted sulfonyl chloride at a temperature above RT, preferably at about 50° C., to form the sulfonamide 17. The pyridyl sulfonamide 17 is converted to the piperidine such as by hydrogenation in the presence of catalyst, such as platinum(IV) oxide.

The protected piperidine 18 is formed, such as with di-tert-butyl carbonate in the presence of base, at a temperature above RT, preferably at about 50° C. The substituted sulfonamide 19 is formed by alkylation of 18, such as with NaH, at a temperature of about RT, or alternatively in the presence of base, such as K$_2$CO$_3$, a temperature above RT, preferably above about 50° C., even more preferably at about 75° C.

Scheme 7

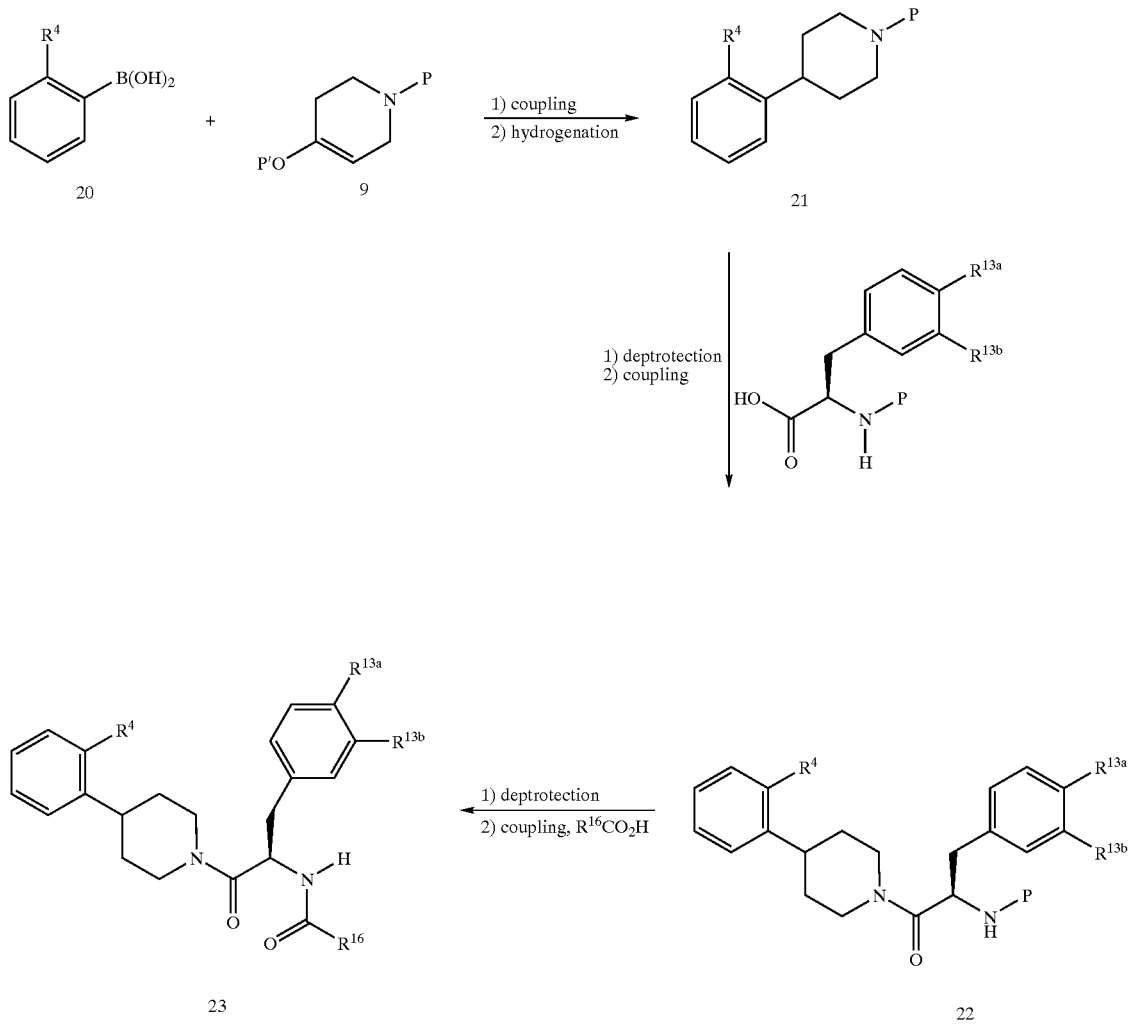

Substituted piperidine derivatives also may be prepared by a process similar to that shown in Scheme 7. Phenylboronic acids 20 are coupled with tetrahydro-pyridines 9 in the presence of base, such as $Na_2CO_3$, and a catalyst, such as $Pd(PPh_3)_4$, followed by hydrogenation, such as with hydrogen in the presence of a catalyst, such as Pd on carbon, to yield the protected phenylpiperidines 21. The phenylpiperidines 21 is deprotected, and coupled with the appropriate amino acid using traditional coupling chemistry to yield compound 22. After further deprotection and coupling with $R^2CO_2H$, the piperidine derivatives 23 is formed with standard peptide chemistry.

Compounds of Formula I, where $R^2$ is $—CH_2R^{2a}$, may be prepared in as described in Scheme 8. To a free amine 7 in a solvent, such as $ClCH_2CH_{12}C_1$, and base, such as DIEA, an aldehyde and reducing agent such as $NaBH(OAc)_3$ are added, to form the substituted amine 4, where $R^{2a}$, is aryl, heterocyclyl or cycloalkyl. The reaction is preferably kept at about RT.

Compounds of Formula I, where $R^2$ is $—C(=O)OR^9$, may also be prepared as described in Scheme 9. Alcohol 24 is converted to the anhydride, such as with phosgene and base, such as DIEA, at a temperature between $-23°$ C. and reflux, preferably at about $0°$ C. and reflux, in a suitable solvent, such as $CH_2Cl_2$. To the mixture is added the piperazine derivative 7 and base to afford the carbamate 4. A similar procedure can be used for the reactions of amines to form the corresponding ureas.

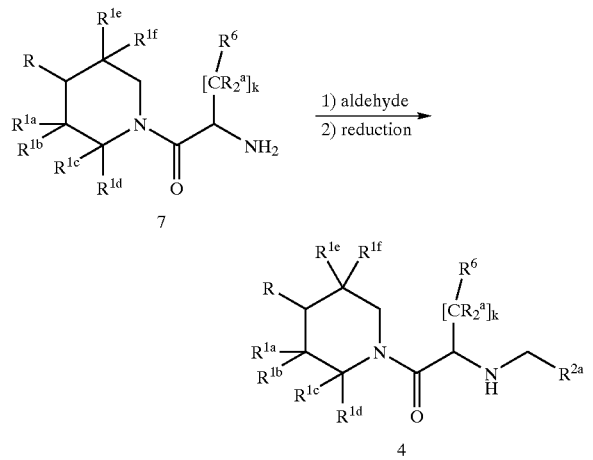

Compounds of Formula I may also be prepared in a convergent manner as described in Scheme 10. Following the procedure for the synthesis of Scheme 9, the aniline 26 was prepared from the corresponding amine 25, aldehyde and reducing agent, such as $NaBH(OAc)_3$. The aniline 26 may be further substituted using, for example methylsulfonyl chloride, base such as pyridine, and DMAP (cat.), in a suitable solvent, such as $ClCH_2CH_2Cl$ to yield the sulfonamide 27.

Scheme 11

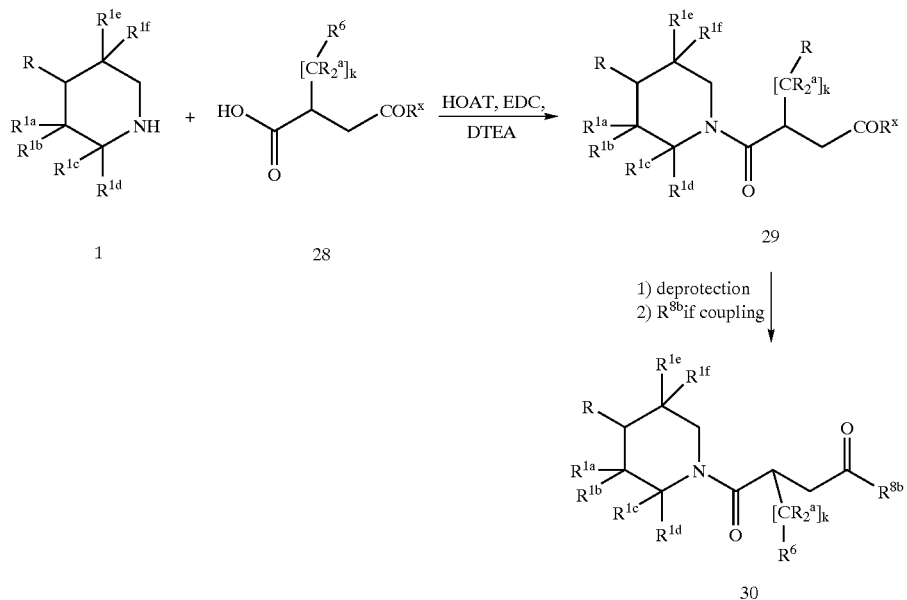

Compounds of Formula I, where $R^2$ is —$COR^a$ and Y is $CH_2$ may be prepared as described in Scheme 11. Piperidine 1 can be coupled with diacid 28 (where $R^x$ is an acid protecting group, such as alkoxy, aryloxy, benzyloxy, and the like) to form the piperidinyl amide 29. The amide 29 is deprotected to form the free acid which can be coupled with appropriate reagents (where $R^{8b}$ is capable of reacting with an acid, such as an optionally substituted amine) to form compounds 30. Such coupling can be with normal amino acid coupling reagents.

Scheme 12

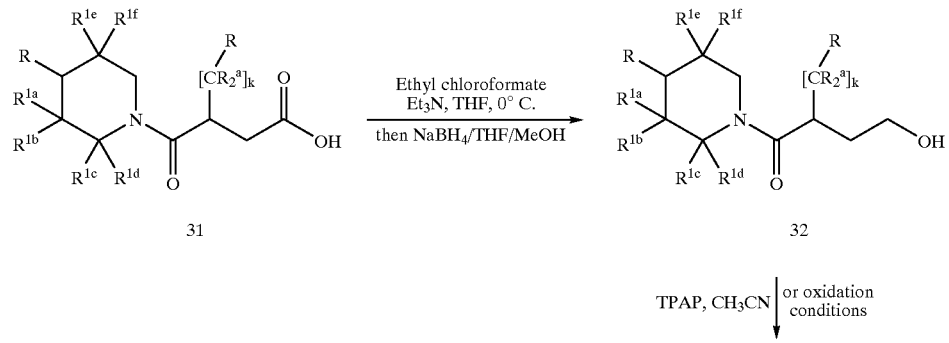

-continued

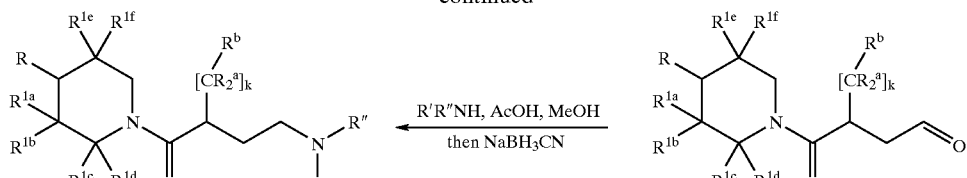

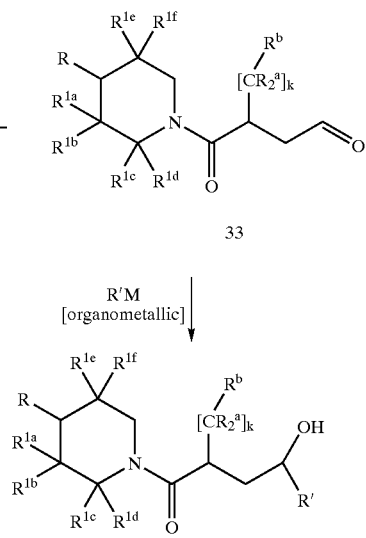

Alternatively, several types of compounds of Formula I, where $R^2$ is —COR8 and Y is $CH_2$ may be prepared as described in Scheme 12. The free acid 31 can be reduced to the alcohol 32, for example using a two step procedure that converts the acid 31 first to the mixed carbonate, such as with ethyl chloroformate, then is reduced to the alcohol 32, such as with $NaBH_4$. The alcohol 32 can be converted to the aldehyde 33 (using reagents such as with Dess Martin reagent, TPAP or Swern oxidation) which can be further reacted with substituted amines, such as in the presence of acetic acid, then reduced, such as with $NaBH_3CN$ to form amines 34. Alternatively the aldehyde 33 can react with organometallic agents to form the alcohols 35.

Scheme 13

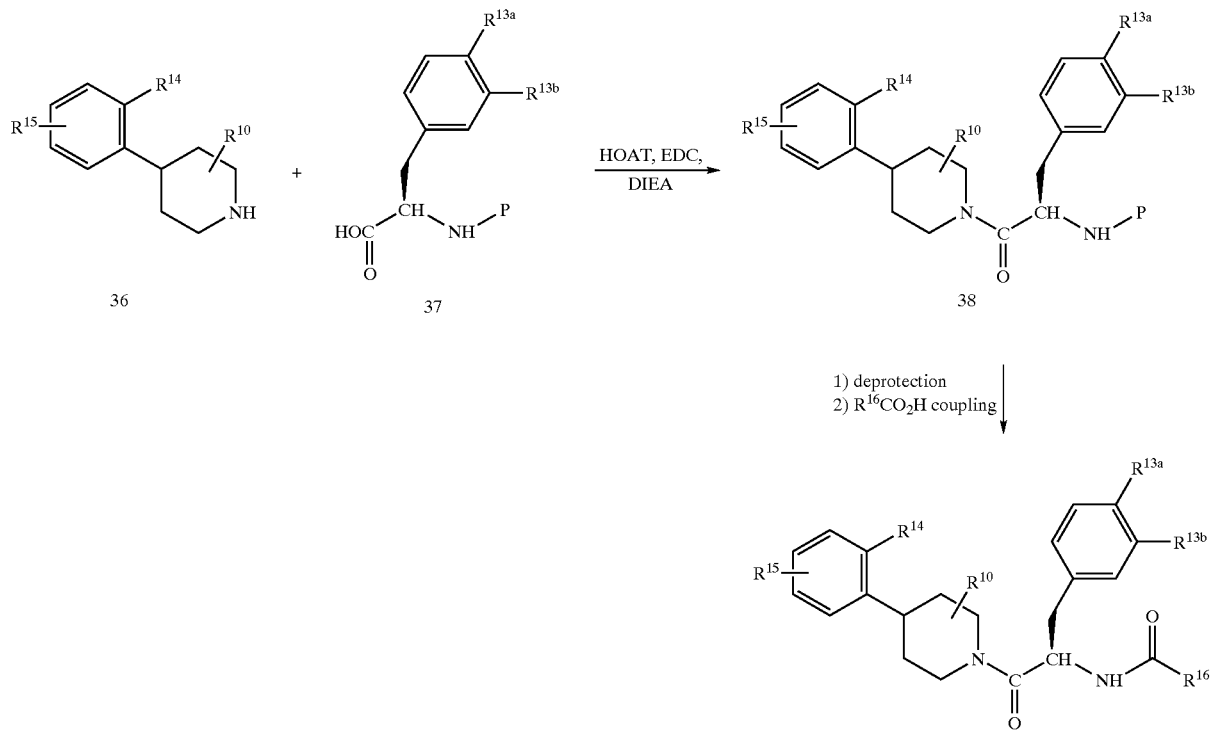

Compounds of Formula II may be prepared as described in Scheme 13. Protected D-phenylalanine derivatives 37 (where P is a protecting group) are coupled with the substituted phenyl piperazine 36 using standard peptide coupling conditions, such as with HOAT, EDC, and DIEA in a solvent, such as MeCl$_2$, and reacted at RT, to afford the protected piperazine phenylalanine compounds 38. Removal of the protecting group P (CBZ, BOC, FMOC etc.) is accomplished using conventional methods, such as with a solution of 50% TFA and CH$_2$Cl$_2$ (to remove a Boc group), to yield the free amine. The free amine is treated with base, such as DIEA in a solvent, such as MeCl$_2$. The reaction mixture is coupled with a substituted acid, using standard peptide coupling conditions, such as with HOAT, EDC, and DIEA in a solvent, such as at a temperature of about RT, to yield the desired compound 39.

Scheme 14

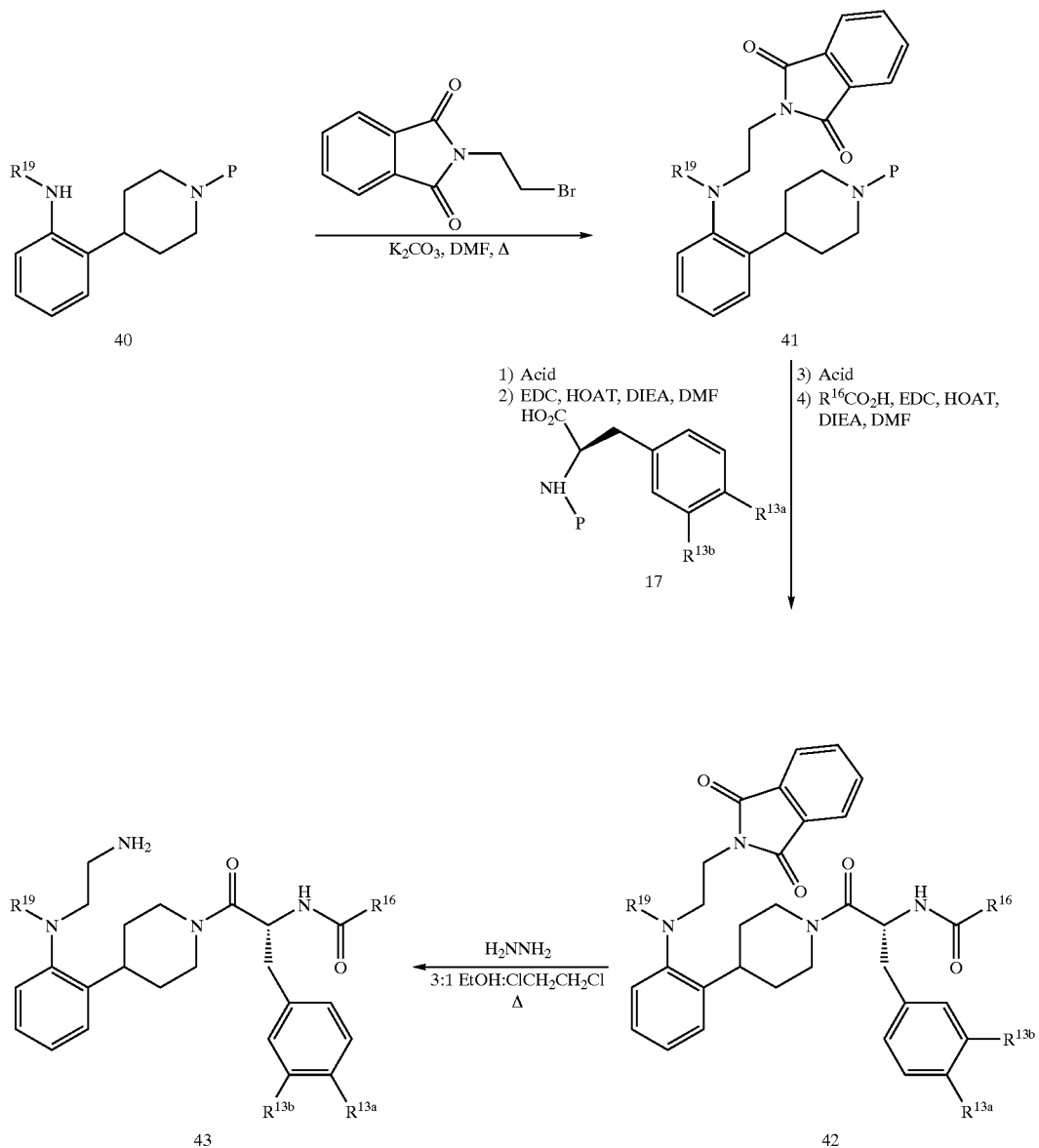

Compounds of Formula II, where $R^{20}$ is aminoalkyl, may be prepared as described in Scheme 14. Aniline 40 is coupled with a protected alkylamine, such as N-(2-bromomethyl)phthalimide in the presence of base, to yield the substituted amine 41. After treatment with acid, such as HCl, at a temperature of about RT, coupling with normal peptide conditions yields the protected piperidyl-phenylalanine derivatives. Following acidification, coupling with an acid yields the protected compound 42. Deprotection, such as with hydrazine, at a temperature above RT, preferably at a temperature above 50° C., more preferably at about 60° C., yields the free amine 43.

Scheme 15

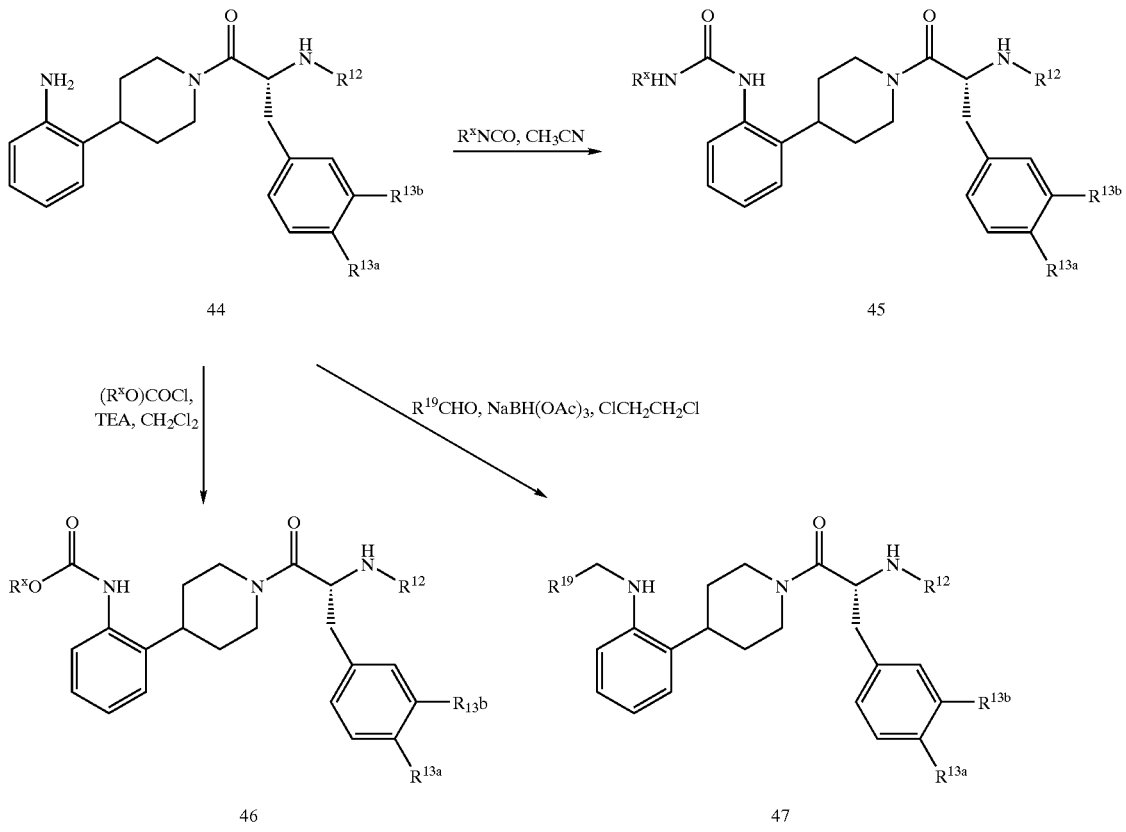

Compounds of Formula II may be prepared as described in Scheme 15 starting with aniline 44. The aniline 44 is reacted with an isocyanate to form ureas 45. Alternatively, carbamic acid derivatives 46 can be prepared from treatment of the aniline 44 with acid halide esters, such as haloformates. Treatment of the aniline 44 with aldehydes in the presence of a reducing agent, such as $NaB(OAc)_3$ provides the substituted amines 47.

Scheme 16

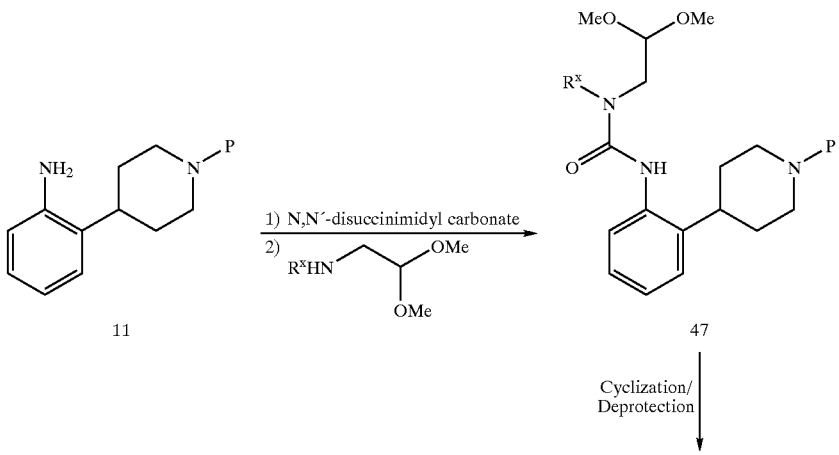

Cyclization/
Deprotection

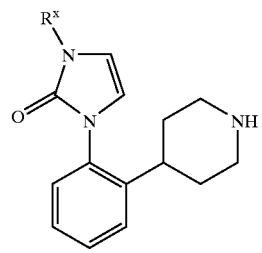

48

Imidazolone substituted piperidines can be prepared by the method described in Scheme 16. The urea 47 is prepared from the aniline 11. N,N'-Disuccinimidyl carbonate is reacted with the aniline 11 (similar to the method described in WO01/44230), followed by treatment with a substituted 2,2-dimethoxyethylamine (similar to the method described in Wong et al., Hetereocycles, 26, 3153–8 (1987)) to form the acetal 47. Similar to the method described in J. Org. Chem., 62, 2320–21 (1997), treatment with aqueous acid, such as TFA, affords the imidazolone 48. If the piperidine is protected with an acid labile protecting group, the acid also remove the protecting group.

The protected D-phenylalanine derivatives are commercially available or may be prepared by literature methods (R. M. Williams, Synthesis of Optically Active α-Amino Acids, Pergamon Press: Oxford, 1989). Similarly, substituted piperazines are either commercially available, can be prepared via literature methods, or may be prepared following literature methods described for analogous compounds. TIC derivatives can be prepared such as by methods described in WO00/74679. Piperazine derivatives can be prepared such as by methods described in WO95/34311.

The starting compounds defined in Schemes 1–14 may also be present with functional groups in protected form if necessary and/or in the form of salts, provided a salt-forming group is present and the reaction in salt form is possible. If so desired, one compound of formula I can be converted into another compound of formula I or a N-oxide thereof; a compound of formula I can be converted into a salt; a salt of a compound of formula I can be converted into the free compound or another salt; and/or a mixture of isomeric compounds of formula I can be separated into the individual isomers.

N-Oxides can be obtained in a known matter by reacting a compound of formula I with hydrogen peroxide or a peracid, e.g. 3-chloroperoxy-benzoic acid, in an inert solvent, e.g. dichloromethane, at a temperature between about −10–35° C., such as about 0° C.—RT.

If one or more other functional groups, for example carboxy, hydroxy, amino, or mercapto, are or need to be protected in a compound of formulas I–III, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide): this may be done by heating to a melt, or for example by heating as a solid under a high vacuum at elevated temperature, for example from about 130 to about 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H' form, depending on the type of reaction and/or reactants at reduced, normal, or elevated temperature, for example in the range from about −100° C. to about 190° C., preferably from about −80° C. to about 150° C., for example at about −80° C. to about 60° C., at room temperature, at about −20° C. to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g. diethyl acetate, ethers, typically aliphatic ethers, e.g. diethylether, or cyclic ethers, e.g. THF, liquid aromatic hydrocarbons, typically benzene or toluene, alcohols, typically MeOH, EtOH or 1- or 2-propanol, nitriles, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention are known, are commercially available, or can be synthesized in analogy to or according to methods that are known in the art.

The skills required in carrying out the reaction and purification of the resulting reaction products are known to those in the art. Purification procedures include crystallization and normal-phase or reverse-phase chromatography.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. All reactions involving air- or moisture-sensitive compounds were performed under a nitrogen atmosphere. All parts are by weight and temperatures are in Degrees centigrade unless otherwise indicated All compounds showed NMR spectra consistent with their assigned structures. Unless otherwise stated, reactions were run at room temperature.

The following abbreviations are used:
AcOH—acetic acid
$AlH_3$—aluminum hydride
Bn—benzyl
Boc—tert-(butoxycarbonyl)-
Boc-D-Phe-OH—N-tert-(butoxycarbonyl)-D-phenylalanine
Boc-L-Tic-OH—N-tert-(butoxycarbonyl)-L-1,2,3,4-tetrahydroisoquinoline-3-carboxylic acid
Boc-p-Cl-D-Phe-OH—N-tert-(butoxycarbonyl)-para-chloro-D-phenylalanine
Boc-D-3,4-diClPhe-OH—N-tert-(butoxycarbonyl)-3,4-dichloro-D-phenylalanine
BOP-Cl-bis(2-oxo-3-oxazolidinyl)phosphinic chloride
CBZ-N—Carbobenzyloxy
$CH_2Cl_2$—dichloromethane, methylene chloride
$ClCH_2CH_2Cl$—ethylene dichloride
$CH_3CN$—acetonitrile
chxl—cyclohexyl
Cond—concentrated
cyp—cyclopropyl
DIEA—N,N-diisopropylethylamine
DMAP—4-dimethylaminopyridine
DME—ethylene glycol dimethylether
DMF—dimethylformamide
EDC—1-ethyl-3-[3-(dimethylamino)propyl]carbodiimide hydrochloride
$Et_2O$—diethyl ether
EtOAc—ethyl acetate
EtOH—ethyl alcohol
Fmoc —N-(9-fluorenylmethoxycarbonyl)-
g—gram
h—hour
$H_2$—hydrogen
$H_2O$—water
$H_3PO_4$—Phosphoric acid
$HCO_2NH_4$—ammonium formate
HCl—hydrochloric acid
HOAT—1-hydroxy-7-azabenzotriazole
HOBT—1-hydroxybenzotriazole hydrate
$K_2CO_3$—potassium carbonate
LDA—lithium diisopropylamide LiOH—lithium hydroxide
LiCl—lithium chloride
LiAlH$_4$—lithium aluminum hydride
mg—milligram
ml—milliliter
min—minutes
MeOH—methyl alcohol
NaCl—sodium chloride
NaOH—sodium hydroxide
NaH—sodium hydride
Na$_2$CO$_3$—sodium carbonate
NaHCO$_3$—sodium bicarbonate
NaBH$_3$CN—sodium cyanoborohydride
NaBH(OAc)$_3$—sodium triacetoxyborohydride
NaHMDS—sodium bis(trimethylsilyl)amide
NaH$_2$PO$_4$—sodium phosphate monobasic
Na$_2$SO$_4$—sodium sulfate
N$_2$—nitrogen
NH$_3$—ammonia
NH$_4$Cl—ammonium chloride
NH$_4$OAc—ammonium acetate
(NH$_4$)$_2$SO$_4$—ammonium sulfate
Pd/C—palladium on carbon
phe—phenylalanine
pro—proline
RT—room temperature
Satd—saturated
SiO$_2$—silica
SnCl$_2$.2H$_2$O—stannous chloride, dihydrate
soln—solution
TEA—triethylamine
TFA—trifluoroacetic acid
THF—tetrahydrofuran
TIC—tetrahydroisoquinoline carboxylic acid
TicOH—tetrahydro isoquinoline carboxylic acid
TPAP—tetrapropyl ammonium perruthenate
TLC—thin layer chromatography Preparative HPLC (TFA Buffer): Unless otherwise stated, compounds that were purified by preparative HPLC using a TFA buffer were run on a YMC-ODS AM (150×20 mm, 5 micron particle size) column, with a flowrate of 20 mL/min. The eluant used was 10 to 100% CH$_3$CN in H$_2$O over 7 min then 3.5 min at 100% CH$_3$CN. Both solvents were buffered with 0.1% TFA.

Preparative HPLC (AcOH Buffer): The following method was used when AcOH was used as a buffer. YMC-ODS AM (150×20 mm, 5 micron particle size) column, with a flowrate of 20 mL/min. The eluant used was 10 to 100% CH$_3$CN in H$_2$O over 6 min then 3.5 min at 100% CH$_3$CN. Both solvents were buffered with 0.1% AcOH.

Preparation A

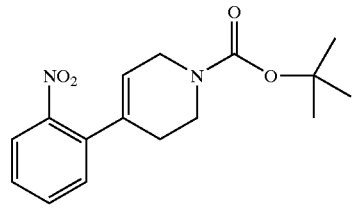

tert-Butyl 4-(2-nitrophenyl)-1,2,5,6-tetrahydropyridinecarboxylate

To a 100 mL round-bottomed flask equipped with stirring was added 2-nitrophenyl boronic acid (Combi-Blocks Chemical Company) (210 mg, 1.3 mmol), LiCl (Aldrich) (168 mg, 4 mmol), tetrakis(triphenyl-phosphine)palladium (O) (Strem Chemical Company) (69 mg, 0.06 mmol) and tert-butyl 4-[(trifluoromethyl)-sulfonyloxy]-1,2,5,6-tetrahydro-pyridinecarboxylate [prepared by the method of Wustrow, D. J. and Wise, L. D., Synthesis 1991, 993–995, from tert-butyl-4-oxopiperidine-1-carboxylate (Aldrich), LDA (Aldrich) and N-phenyltrifluoromethanesulfonimide (Aldrich)] (397 mg, 1.2 mmol) in DME (5 mL). The reaction mixture was purged with N$_2$ and a 2 M soln of Na$_2$CO$_3$ (1.8 mL, 3.6 mmol) was introduced. After heating the mixture to 90° C. for 3 h, the reaction was cooled to 25° C. and diluted with EtOAc (15 mL). The organic layer was separated, washed with 10% Na$_2$CO$_3$, H$_2$O and satd NaCl and dried over Na$_2$SO$_4$, filtered and concentrated in vacuo to afford a dark yellow oil. The crude material was purified by column chromatography (3:1 hexane:EtOAc) to give the title compound as a white solid (240 mg). MS (ESI, pos. ion) m/z: 305 (M+1). Calc'd for C$_{16}$H$_{20}$N$_2$O$_4$: 304.34.

Preparation B

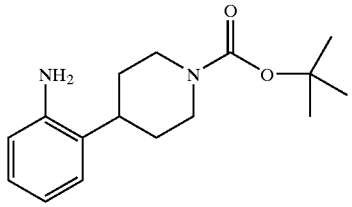

tert-Butyl 4-(2-aminophenyl)piperidinecarboxylate

To a pressure bottle was added tert-butyl 4-(2-nitrophenyl)-1,2,5,6-tetrahydropyridinecarboxylate (Preparation A) (145 mg, 0.48 mmol), 10% Pd/C (Aldrich) (51 mg) and 10 mL of a 1:1 mixture of MeOH:EtOH. The reaction mixture was hydrogenated at 50 psi overnight, then the crude mixture was filtered through Celite® (Aldrich) and concentrated in vacuo to afford the title compound as a colorless oil (128 mg, 97%). MS (ESI, pos. ion) m/z: 277 (M+1). Calc'd for C$_{16}$H$_{24}$N$_2$O$_2$: 276.37.

Preparation C

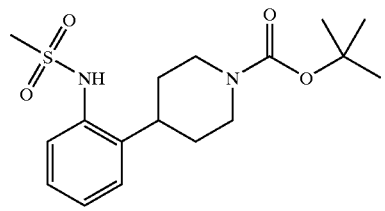

tert-Butyl 4-{2-[(methylsulfonyl)amino]phenyl}piperidine-carboxylate

To a 100 mL round-bottomed flask was added tert-butyl 4-(2-aminophenyl)piperidinecarboxylate (Preparation B) (1.93 g, 7.2 mmol) and 1,2-dichloroethane (50 mL). The solution was magnetically stirred under a N$_2$ atmosphere, treated with pyridine (2.9 mL, 36 mmol) and methanesulfonyl chloride (Aldrich) (1.1 mL, 1.7 g, 14 mmol). The vessel was immersed in a 50° C. oil bath for 6 h then cooled to 25° C. The solvent was removed in vacuo, and the residue was partitioned between EtOAc (200 mL) and 1 N HCl (100 mL). The organic layer was washed with satd NaHCO$_3$ (75 mL), satd NaCl (50 mL), dried over Na$_2$SO$_4$, filtered and concentrated to give a foam. The foam was purified by silica gel chromatography (3:/EtOAc:hexane) to provide the title compound as a white foam (2.1 g). MS (ESI, pos. ion) m/z: 355 (M+1); (ESI, neg. ion) m/z: 353 (M−1). Calc'd for C$_{17}$H$_{26}$N$_2$O$_4$S: 354.47.

EXAMPLE 1

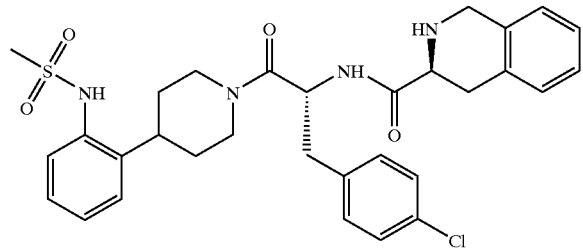

N-[(1R)-1-[(4-Chlorophenyl)methyl]-2-(4-{2-[(methylsulfonyl)amino]phenyl}-piperidyl)-2-oxoethyl]-((3S)(3-1,2,3,4-tetrahydroisoquinolyl)) carboxamide

Step (a) 4-(2-Nitrophenyl)-pyridine

To a 1 L round-bottomed flask equipped with a reflux condenser was added 2-nitrobenzeneboronic acid (Lancaster) (10 g, 60 mmol), 4-bromopyridine hydrochloride (Fluka) (12 g, 60 mmol), Na$_2$CO$_3$ (25 g, 240 mmol), DME (300 in L) and H$_2$O (100 mL). The mixture was stirred magnetically, degassed in vacuo and purged with N$_2$. The process was repeated five times then tetrakis (triphenylphosphine)-palladium (0) (Strem Chemicals) (3.5 g, 3.0 mmol) was added and the reaction mixture was stirred at reflux under a slight positive pressure of N$_2$ for 15 h. The reaction mixture was concentrated in vacuo and the residue partitioned between EtOAc (100 mL) and satd NaCl (50 mL) diluted with H$_2$O (50 mL). The aqueous phase was further extracted with EtOAc (2×100 mL). The combined organic fractions were extracted with 1 N HCl (3×100 mL). The combined acidic extract was washed with EtOAc (100 mL), cooled in an ice bath and adjusted to pH 10 with 5 N NaOH. The aqueous solution was saturated with NaCl and extracted with EtOAc (3×100 mL). The combined EtOAc extracts were washed with satd NaCl (100 mL), dried over Na$_2$SO$_4$, filtered and concentrated to afford a brown oil. Purification by silica gel chromatography (5:30–65, 1 M NH$_3$/MeOH-EtOAc-hexane) provided the title compound as a viscous, dark orange oil (6.0 g). MS (ESI, pos. ion) m/z: 201 (M+1). Calc'd for C$_{11}$H$_8$N$_2$O$_2$: 200.19.

Step (b) 2-(4-Pyridyl)phenylamine

To a 500 mL round-bottomed flask was added a solution of 4-(2-nitrophenyl)-pyridine (Step a) (7.1 g, 36 mmol) in MeOH (300 mL). The solution was treated dropwise with concd HCl (6.7 mL, 84 mmol) and purged with N$_2$. Pd/C (10%, Aldrich) (2.5 g) was added, H$_2$ was introduced and the suspension was magnetically stirred under atmospheric H$_2$ pressure for 15 h at 25° C. The suspension was purged with N$_2$, filtered through Celite® (Aldrich) (25 g) and the filter cake was washed with MeOH (400 mL). The filtrate was concentrated in vacuo to a yellow powder which was partitioned between EtOAc (200 mL) and 1 N NaOH (100 mL). The organic layer was washed with water (100 mL), satd NaCl (50 mL), dried over Na$_2$SO$_4$, filtered and concentrated in vacuo to afford the title compound as a viscous yellow oil which solidified upon standing (6.0 g). MP 81–83° C. MS (ESI, pos. ion) m/z: 171 (M+1); (ESI, neg. ion) m/z: 169 (M−1). Calc'd for C$_{11}$H$_{10}$N$_2$: 170.21.

Step (c) (Methylsulfonyl)(2-(4-pyridyl)phenyl) amine

A solution of 2-(4-pyridyl)phenylamine (Step b) (500 mg, 2.9 mmol) in 1,2-dichloroethane (35 mL) was stirred magnetically under N$_2$ in a 100 mL round-bottomed flask at 25° C. The solution was treated with TEA (Aldrich) (400 μL, 2.9 mmol) followed by methanesulfonyl chloride (Aldrich) (230 μL, 335 mg, 2.9 mmol). The vessel was heated in a 50° C. oil bath for 3 h. The reaction mixture was concentrated in vacuo and the resulting residue was partitioned between EtOAc (100 mL) and satd NaHCO$_3$ (50 mL). The organic layer was washed with satd NaCl (50 mL), dried over Na$_2$SO$_4$, filtered and concentrated in vacuo to afford a yellow oil. To the oil was added 5:25:75 1 M NH$_3$/MeOH:EtOAc:hexane (10 mL). A yellow precipitate formed which was collected by filtration and dried in vacuo at 40° C. to afford the title compound as a yellow solid (480 mg). MS (ESI, pos. ion) m/z: 249 (M+1); (ESI, neg. ion) m/z: 247 (M−1). Calc'd for C$_{12}$H$_{12}$N$_2$O$_2$S: 248.30.

Step (d) tert-Butyl 4-{2-[(methylsulfonyl)amino] phenyl}piperidine-carboxylate To a 250 mL Parr flask was added (methylsulfonyl)(2-(4-pyridyl)phenyl)amine (Step c) (480 mg, 1.9 mmol), MeOH (25 mL) and concd HCl (0.217 mL, 1.9 mmol). The flask was purged with N$_2$, then platinum (IV) oxide (Aldrich) (200 mg) was added. The suspension was hydrogenated on a Parr shaker at 55 psi H$_2$ for 1 h, at which point the color of the methanolic solution changed from yellow to colorless. The reaction mixture was filtered through a bed of Celite® (Aldrich), and the filter cake was washed with MeOH (250 mL). The filtrate was concentrated in vacuo to 10 mL and EtOAc (40 mL) was added, resulting in precipitation of the compound. The precipitate was collected by filtration and dried in vacuo to afford a white solid (331 mg), which was used without further purification. The solid was suspended in CH$_2$Cl$_2$ (10 mL) in a 50 mL round-bottomed flask and magnetically stirred at 25° C. To the suspension was added TEA (Aldrich) (0.32 mL, 2.28 mmol), followed by di tert-butyl carbonate (Aldrich) (272 mg, 1.25 mmol). The mixture was heated in a 50° C. oil bath for 4 h. The mixture was removed from the oil bath and partitioned between CH$_2$Cl$_2$ (200 mL) and satd NaHCO$_3$ (20 mL). The organic layer was washed with satd NaCl (20 mL), dried over Na$_2$SO$_4$, filtered and concentrated to give an oil. The oil was purified by silica gel chromatography (1:4 EtOAc:hexane) to provide the title compound as a colorless oil (250 mg). MS (ESI, pos. ion) m/z: 355 (M+1); (ESI, neg. ion) m/z: 353 (M−1). Calc'd for C$_{17}$H$_{26}$N$_2$O$_4$5:354.47.

Step (e) 4-{2-[(Methylsulfonyl)amino]phenyl}-piperidine

To a 25 ml, round-bottomed flask equipped with stirring was added tert-butyl 4-(2-[{methylsulfonyl)amino] phenyl}piperidino-carboxylate (Step d) (610 mg, 1.72 mmol) followed by a saturated soln of HCl in EtOAc (10 mL). The reaction mixture was stirred at RT for 1 h and the title compound (HCl salt) was isolated by filtration as a white solid (460 mg). MS (ESI, pos. ion) m/z: 255 (M+1). Calc'd for C$_{12}$H$_{19}$ClN$_2$O$_2$S: 290.81.

Step (f) N-[(1R)-1-[(4-Chlorophenyl)methyl]-2-(4-
{2-[(methylsulfonyl)amino]phenyl}piperidyl)-2-
oxoethyl](tert-butoxy)carboxamide To a round-bottomed flask equipped with stirring was added 4-{2-[(methylsulfonyl)amino]phenyl}piperidine (Step e) (400 mg, 1.38 mmol) and DMF (5 mL). The mixture was stirred for 5 min, then treated with N-Boc-p-Cl-D-PheOH (PepTech Corporation) (454 mg, 1.52 mmol), HOAT (Aldrich) (188 mg, 1.38 mmol), EDC (Aldrich) (529 mg, 2.76 mmol) and DIEA (Aldrich) (240 μL, 1.38 mmol) and stirred at RT for 2.5 h. The reaction mixture was diluted with EtOAc (15 mL) and 10% $Na_2CO_3$ (20 mL) was added. The organic layer was separated, washed with 10% $Na_2CO_3$, $H_2O$ and satd NaCl, dried over $Na_2SO_4$, filtered and concentrated in vacuo to afford the title compound as a white foam (655 mg). MS (ESI, pos. ion) m/z: 536 (M+1). Calc'd for $C_{26}H_{14}O_5S$: 536.08.

Step (g) (2R)-2-Amino-3-(4-chlorophenyl)-1-(4-{2-
[(methylsulfonyl)amino]phenyl}piperidyl)propan-1-
one The title compound was prepared according to the procedure described in Step (e) using N-[(1R)-1-[(4-chlorophenyl)methyl]-2-(4-{2-[(methylsulfonyl)-amino]phenyl}piperidyl)-2-oxoethyl](tert-butoxy)-carboxamide (Step f) (250 mg, 0.50 mmol) and a saturated soln of HCl in EtOAc (10 mL). The title compound (HCl salt) was isolated by filtration as a white solid (195 mg, 83%). MS (ESI, pos. ion) m/z: 473 (M+1). Calc'd for $C_{21}H_{27}Cl_2N_3O_3S$: 472.43.

Step (h) tert-Butyl 3-{N-[(1R)-1-[(4-chlorophenyl)
methyl]-2-(4-{2-[(methylsulfonyl)-amino]
phenylpiperidyl)2-oxoethyl]carbamoyl}(3S)-1,2,3,4-
tetrahydroisoquinoline-2-carboxylate The title compound was prepared according to the procedure described in Step (f) using (2R)-2-amino-3-(4-chlorophenyl)-1-(4-{2-[(methylsulfonyl)amino]phenyl}piperidyl)propan-1-one (Step g) (325 mg, 0.74 mmol), Boc-L-TicOH (Bachem Company) (225 mg, 0.81 mmol), HOAT (Aldrich) (101 mg, 0.74 mmol), EDC (Aldrich) (284 mg, 1.48 mmol) and DIEA (Aldrich) (129 μL, 0.74 mmol) in DMF (5 mL). The title compound was obtained after purification by silica gel chromatography (1:2 hexane:EtOAc) as a white solid (310 mg). MS (ESI, pos. ion) m/z: 695 (M+1). Calc'd for $C_{36}H_{43}ClN_4O_6S$: 695.27.

Step (i) N-[(1R)-1-[(4-Chlorophenyl)methyl]-2-(4-
{2-[(methylsulfonyl)amino]phenyl}-piperidyl)-2-
oxoethyl]((3S)(3-1,2,3,4-tetrahydroisoquinolyl))
carboxamide The title compound was prepared according to the procedure described in (Step e) using tert-butyl 3-{N-[(1R)-1-[(4-chlorophenyl)methyl]-2-(4-{2-[(methylsulfonyl)-amino]phenylpiperidyl)2-oxoethyl]carbamoyl}(3S)-1,2,3,4-tetrahydroisoquinoline-2-carboxylate (Step h) (310 mg, 0.45 mmol) and a saturated soln of HCl in EtOAc (10 mL). The title compound was isolated by filtration and purified by reverse phase preparative HPLC [LUNA $C_{18}$; 5 μm, 250×20 mm; 20% to 100% $CH_3CN/H_2O$ (95:5, 20 mM $NH_4OAc$, pH 4.5) in $H_2O$ (20 mM $NH_4OAc$, pH 4.5) over 6 min, then 100% $CH_3CN/H_2O$ (95:5, 20 mM $NH_4OAc$, pH 4.5) for 5 min; 20 mL/min] to provide the acetate salt as a white solid (145 mg, 47%). MS (ESI, pos ion) m/z: 595 (M+1). Calc'd for $C_{31}H_{35}N_4O_4SCl$: 594.21. Anal. Calcd for $C_{31}H_{35}N_4O_4SCl \cdot C_2H_4O_2 \cdot 1.5H_2O$: C, 58.10; H, 6.21; N, 8.21; Cl, 5.20. Found: C, 58.30; H, 6.12; N, 8.20; Cl, 5.25.

EXAMPLE 2

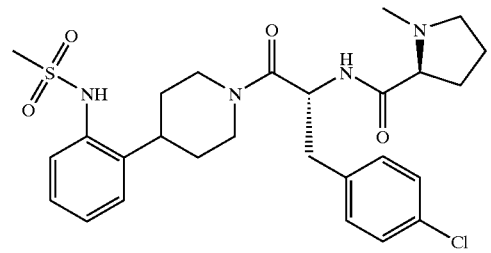

N-[(1R)-1-[(4-Chlorophenyl)methyl]-2-(4-{2-
[(methylsulfonyl)amino]phenyl}-piperidyl)-2-
oxoethyl]((2S)-1-methylpyrrolidin-2-yl)carboxamide The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (210 mg, 0.48 mmol), N-methyl S-proline (Hachem Company) (68 mg, 0.53 mmol), HOAT (Aldrich) (65 mg, 0.48 mmol), EDC (Aldrich) (184 mg, 0.96 mmol) and DIEA (Aldrich) (84 μL, 0.48 mmol). Purification by reverse phase preparative HPLC (Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min]provided the title compound as a colorless oil (120 mg). MS (ESI, pos. ion) m/z: 547 (M+1). Calc'd for $C_{27}H_{35}ClN_4O_4S$: 546.21.

EXAMPLE 3

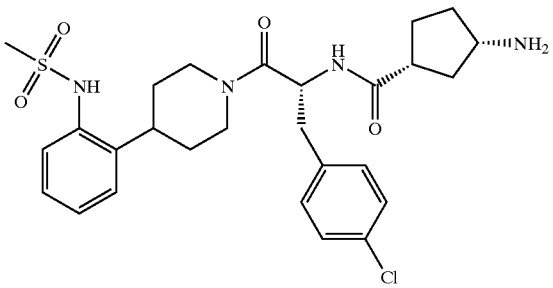

N-[(1R)-1-[(4-Chlorophenyl)methyl]-2-(4-{2-
[(methylsulfonyl)amino]phenyl}-piperidyl)-2-
oxoethyl]((3S, 1R)-3-aminocyclopentyl)
carboxamide Step (a) N-[(1R)-1-[(4-chlorophenyl)methyl]-2-(4-
{2-[(methylsulfonyl)amino]phenyl}-piperidyl)-2-
oxoethyl]-{(3S, 1R)-3-[(tert-butoxy)
carbonylamino]-cyclopentyl}-carboxamide The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), (+)-(1R, 3S)—N-Boc-aminocyclopentane-3-carboxylic acid (PepTech Corporation) (344 mg, 1.5 mmol), HOAT (Aldrich) (232 mg, 1.70 mmol) and EDC (Aldrich) (544, 2.84 mmol) in DMF (10 mL). Purification by silica gel chromatography (100% EtOAc) provided the title compound as a white foam (421 mg). MS (ESI, pos. ion) m/z: 647 (M+1); MS (ESI, neg ion) m/z: 645 (M−1). Calc'd for $C_{32}H_{43}ClN_4O_6S$: 647.23.

Step (b) N-[(1R)-1-[(4-Chlorophenyl)methyl]-2-(4-{2-[(methylsulfonyl)amino]phenyl}-piperidyl)-2-oxoethyl]((3S, 1R) 3-aminocyclopentyl)carboxamide To a 50 mL round-bottomed flask was added N-[(1R)-1-[(4-chlorophenyl)methyl]-2-(4-{2-[(methylsulfonyl)-amino]phenyl}-piperidyl)-2-oxoethyl]{(3S, 1R)-3-[(tert-butoxy)carbonylamino]-cyclopentyl}-carboxamide (Step a) (323 mg, 0.5 mmol) followed by a 50% soln of TFA in $CH_2Cl_2$ (20 mL). After stirring for 2 h, the solvent was removed in vacuo. Purification by preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white foam (145 mg). MS (ESI, pos. ion) m/z: 547 (M+1); (ESI, neg. ion) 545 (M−1). Calc'd for $C_{27}H_{35}ClN_4O_4S$: 546.21. Anal. Calcd for $C_{27}H_{35}ClN_4O_4S\cdot1.2C_2HF_3O_2$: C, 51.63; H, 5.49; N, 8.19. Found: C, 51.69; H, 5.49; N, 8.14.

EXAMPLE 4

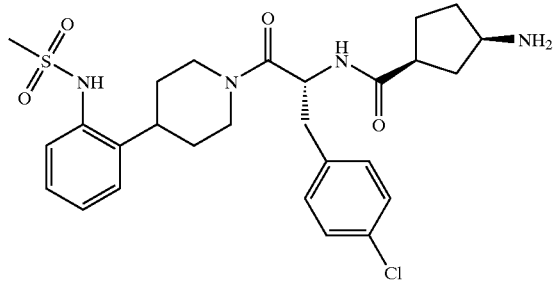

N-[(1R)-1-[(4-Chlorophenyl)methyl]-2-(4-{2-[(methylsulfonyl)amino]phenyl}-piperidyl)-2-oxoethyl]((1S, 3R)-3-aminocyclopentyl)carboxamide Step (a) N-[(1R)-1-[(4-Chlorophenyl)methyl]-2-(4-{2[(methylsulfonyl)amino]phenyl}-piperidyl)-2-oxoethyl]-{(1S,3R)-3-[(tert-butoxy)carbonylamino]-cyclopentyl}-carboxamide The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), (−)-(1S, 3R)—N-Boc-aminocyclopentane-3-carboxylic acid (PepTech Corporation) (344 mg, 1.5 mmol), HOAT (Aldrich) (232 mg, 1.70 mmol) and EDC (Aldrich) (544 mg, 2.84 mmol) in DMF (10 mL). Purification by silica gel chromatography (100% EtOAc) provided the title compound as a white foam (402 mg). MS (ESI, pos. ion) m/z: 647 (M+1); MS (ESI, neg. ion) m/z: 645 (M−1). Calc'd for $C_{32}H_{43}ClN_4O_6S$: 647.23.

Step (b) N-[(1R)-1-[(4-Chlorophenyl)methyl]-2-(4-{2-[(methylsulfonyl)amino]phenyl}-piperidyl)-2-oxoethyl]((1S,3R)-3-aminocyclopentyl)carboxamide The title compound was prepared according to the procedure described in Example 3 Step (b) from N-[(1R)-1-[(4-chlorophenyl)methyl]-2-(4-{2-[(methylsulfonyl)-amino]phenyl}-piperidyl)-2-oxoethyl]{(1S,3R)-3-[(tert-butoxy)carbonylamino]-cyclopentyl}-carboxamide (Step a) (323 mg, 0.5 mmol) and a 50% soln of TFA in $CH_2Cl_2$ (20 mL). Purification by preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white foam (113 mg). MS (ESI, pos. ion) m/z: 547 (M+1); (ESI, neg. ion) m/z: 545 (M−1). Calc'd for $C_{27}H_{35}ClN_4O_4S$: 546.21.

EXAMPLE 5

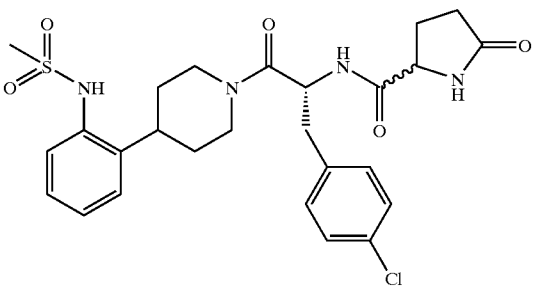

N-[(1R)-1-[(4-Chlorophenyl)methyl]-2-(4-{2-[(methylsulfonyl)amino]phenyl}-piperidyl)-2-oxoethyl](5-oxopyrrolidin-2-yl)carboxamide The title compound was prepared according to the procedure described in Example 1, Step (f) using (2R)-2-amino-3-(4-chlorophenyl)-1-(4-(2-[(methylsulfonyl)-amino] phenyl)piperidyl)propan-1-one (Example 1, Step g) (118 mg, 0.25 mmol), DIEA (Aldrich) (0.05 mL, 0.25 mmol), DL-pyroglutamic acid (Aldrich) (344 mg, 0.5 mmol), HOAT (Aldrich) (68.2 mg, 0.5 mmol) and EDC (Aldrich) (95.8 mg, 0.5 mmol) in DMF (3 mL). Purification by silica gel chromatography (100% EtOAc) provided the title compound as a colorless film (82 mg). MS (ESI, pos. ion) m/z: 547 (M+1); (ESI, neg. ion) in/z: 545 (M−1). Calc'd for $C_{26}H_{31}ClN_4O_5S$: 546.17.

EXAMPLE 6

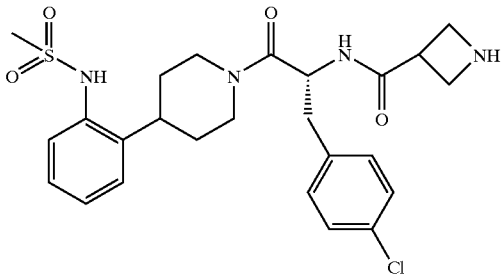

N-[(1R)-1-[(4-Chlorophenyl)methyl]-2-(4-{2-[(methylsulfonyl)amino]phenyl}-piperidyl)-2-oxoethyl]azetidin-3-ylcarboxamide Step (a) tert-Butyl 3-{(N-[(1R)-1-[(4-chlorophenyl)-methyl]-2-(4-(2-[(methylsulfonyl)-amino]phenyl}-piperidyl)-2-oxoethyl]-carbamoyl}azetidinecarboxylate The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), Boc-azetidine-3-carboxylic acid (PepTech Corporation) (344 mg, 1.5 mmol), HOAT (Aldrich) (232 mg, 1.70 mmol) and EDC (Aldrich) (544 mg, 2.84 mmol) in DMF (10 mL). Purification by silica gel chromatography (1:10 MeOH:EtOAc) provided the title compound as a white foam (422 mg). MS (ESI, pos. ion) m/z: 619 (M+1); (ESI, neg. ion) m/z: 617 (M−1). Calc'd for $C_{30}H_{39}ClN_4O_6S$: 619.17.

Step (b) N-[(1R)-1-[(4-Chlorophenyl)methyl]-2-(4-{2-[(methylsulfonyl)amino]phenyl}-piperidyl)-2-oxoethyl]azetidin-3-ylcarboxamide The title compound was prepared according to the procedure described in Example 3 (Step b) from tert-butyl 3-(N-[(1R)-1-[(4-chlorophenyl)methyl]-2-(4-{2-[(methylsulfonyl)-amino]phenyl}-piperidyl)-2-oxoethyl]-carbamoyl)azetidinecarboxylate (Step a) (309 mg, 0.5 mmol) and 50% TFA in $CH_2Cl_2$ (20 mL). Purification by preparative reverse phase HPLC [Phenomenex; 5 μm 250× 21.2 mm, 5% to 95% $CH_3CN$ (0.1% TFA) in $H_2O$ (0.1% TFA) over 30 min, then 100% $CH_3CN$ (0.1% TFA) for 2 min]provided the title compound (TFA salt) as a white foam (205 mg). MS (ESI, pos. ion) m/z: 519 (M+1); (ESI, neg. ion) m/z: 517 (M−1). Calc'd for $C_{25}H_{31}ClN_4O_4S$: 518.18. Anal. Calcd for $C_{25}H_{11}ClN_4O_4S$ 1.4$C_2HF_3O_2$: C, 49.20; H, 4.81; N, 8.26. Found: C, 49.31; H, 4.91; N, 8.25.

EXAMPLE 7

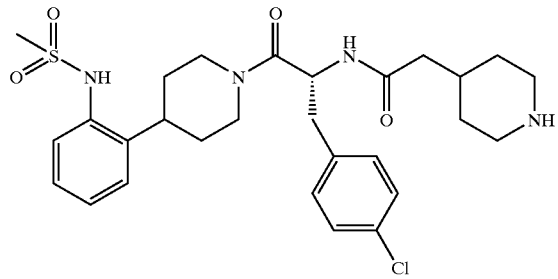

N-[(1R)-1-[(4-Chlorophenyl)methyl]-2-(4-{2-[(methylsulfonyl)amino]phenyl}-piperidyl)-2-oxoethyl]-2-(4-piperidyl)acetamide Step (a) tert-Butyl 4-({N-[(1R)-1-[(4-chlorophenyl)methyl]-2-(4-{2-[(methylsulfonyl)-amino]phenyl}piperidyl)-2-oxoethyl]carbamoyl}methyl)-piperidinecarboxylate The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), N-Boc-4-piperidineacetic acid (AstaTech, Inc.) (365 mg, 1.5 mmol), HOAT (Aldrich) (232 mg, 1.70 mmol) and EDC (Aldrich) (544 mg, 2.84 mmol) in DMF (10 mL). Purification by silica gel chromatography (100% EtOAc) provided the title compound as a white foam (441 mg). MS (ESI, pos. ion) m/z: 661 (M+1); (ESI, neg. ion) m/z: 590 (M−1). Calc'd for $C_{33}H_{45}ClN_4O_6S$: 661.25.

Step (b) N-[(1R)-1-[(4-Chlorophenyl)methyl]-2-(4-{2-[(methylsulfonyl)amino]phenyl}piperidyl)-2-oxoethyl]-2-(4-piperidyl)acetamide The title compound was prepared according to the procedure described in Example 3, Step (b) from tert-butyl 4-({N-[(1R)-1-[(4-chlorophenyl)methyl]-2-(4-(2-[(methylsulfonyl)-amino]phenyl}piperidyl)-2-oxoethyl]-carbamoyl)methyl)-piperidinecarboxylate (Step a) (330 mg, 0.5 mmol) and 50% TFA in $CH_2Cl_2$ (20 mL). Purification by preparative reverse phase HPLC [Phenomenex; 5 μm 250× 21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white foam (242 mg). MS (EST, pos. ion) m/z: 561 (M+1); (ESI, neg. ion) m/z: 559 (M−1). Calc'd for $C_{28}H_{37}ClN_4O_4S$: 560.22. Anal. Calcd for $C_{28}H_{37}ClN_4O_4S.1.6C_2HF_3O_2$: C, 50.40; H, 5.23; N, 7.53. Found: C, 50.54; H, 5.53; N, 7.75.

EXAMPLE 8

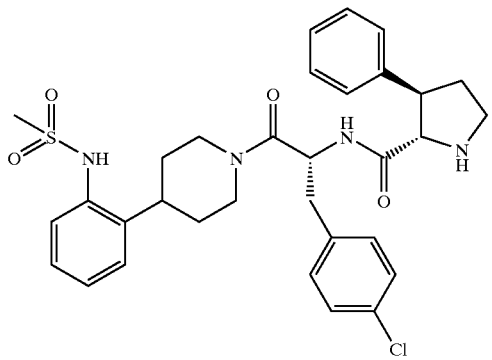

N-[(1R)-1-[(4-Chlorophenyl)methyl]-2-(4-{2-[(methylsulfonyl)amino]phenyl}-piperidyl)-2-oxoethyl][(2S, 3R)-3-phenylpyrrolidin-2-yl)carboxamide Step (a) Fluoren-9-ylmethyl 2-{N-[(1R)-1-[(4-chlorophenyl)methyl]-2-(4-{2-[(methylsulfonyl)amino]phenyl}piperidyl)-2-oxoethyl]carbamoyl}(2S, 3R)-3-phenylpyrrolidine carboxylate The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), Fmoc-L-transPro(3-Ph) (RSP Amino Acid Analogues, Inc.) (620 mg, 1.5 mmol), HOAT (Aldrich) (232 mg, 1.70 mmol) and EDC (Aldrich) (544 mg, 2.84 mmol) in DMF (10 mL). Purification by silica gel chromatography (100% EtOAc) provided the title compound as a white foam (554 mg). MS (ESI, pos. ion) 831 (M+1); (ESI, neg. ion) m/z: 829 (M−1). Calc'd for $C_{47}H_{47}ClN_4O_6S$: 831.42.

Step (b) N-[(1R)-1-[(4-chlorophenyl)methyl]-2-(4-{2[(methylsulfonyl)amino]phenyl}-piperidyl)-2-oxoethyl]((2S, 3R)-3-phenylpyrrolidin-2-yl)carboxamide The title compound was prepared according to the procedure of Sheppeck, J. E., et al. (*Tetrahedron Lett.* 2000, 41, 5329–5333) using fluoren-9-ylmethyl 2-{N-[(1R)-1-[(4-chlorophenyl)methyl]-2-(4-{2-[(methylsulfonyl)amino] phenyl)piperidyl)-2-oxoethyl]carbamoyl}(2S, 3R)-3-phenylpyrrolidine carboxylate (Step a) (415 mg, 0.5 mmol), THF (10 mL), n-octanethiol (Aldrich) (876 mg, 6 mmol) and 1,8-diazabicyclo[5.4.0]undec-7-ene (Aldrich) (5 mg, 0.03 mmol). The reaction mixture was stirred for 5 h at 25° C. and the organic solvent was removed in vacuo. To the residue was added Et$_2$O (20 mL) resulting in precipitation of the compound. The precipitate was collected by filtration and washed with hexane to provide a yellow solid. Purification by preparative reverse phase HPLC [Phenomenex; 5 µm 250×21.2 mm, 5% to 95% CH$_3$CN (0.1% TFA) in H$_2$O (0.1% TFA) over 30 min, then 100% CH$_3$CN (0.1% TFA) for 2 min] provided the title compound (TFA salt) as a white foam (187 mg). MS (ESI, pos. ion) m/z: 609 (M+1); (ESI, neg. ion) m/z: 607 (M−1). Calc'd for C$_{32}$H$_{37}$ClN$_4$O$_4$S: 608.22. Anal. Calcd for C$_{32}$H$_{37}$ClN$_4$O$_4$S.1.4C$_2$HF$_3$O$_2$: C, 54.37; H, 5.03; N, 7.29. Found: C, 54.26; H, 5.19; N, 7.41.

EXAMPLE 9

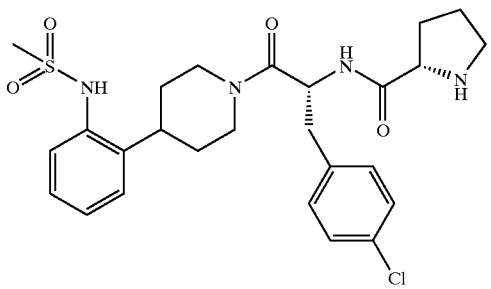

N-[(1R)-1-[(4-Chlorophenyl)methyl]-2-(4-{2-[(methylsulfonyl)amino]phenyl}-piperidyl)-2-oxoethyl]((2S)pyrrolidin-2-yl)carboxamide Step (a) tert-Butyl 2-{N-[(1R)-1-[(4-chlorophenyl)-methyl]-2-(4-{2-[(methylsulfonyl)-amino]-phenyl}-piperidyl)-2-oxoethyl]carbamoyl}-(2S) pyrrolidinecarboxylate The title compound was prepared according to the procedure described in Example 1, Step (f) using (2R)-2-amino-3-(4-chlorophenyl)-1-(4-{2-[(methylsulfonyl)-amino]phenyl}piperidyl)propan-1-one (Example 1, Step g) (471 mg, 1.0 mmol), DIEA (Aldrich) (0.20 mL, 1.0 mmol), Boc-ProOH (Fisher Scientific) (323 mg, 1.5 mmol), HOAT (Aldrich) (232 mg, 1.70 mmol) and EDC (Aldrich) (544 mg, 2.84 mmol) in DMF (10 mL). Purification by silica gel chromatography (100% EtOAc) provided the title compound as a white foam (428 mg). MS (ESI, pos. ion) m/z: 633 (M+1); (ESI, neg. ion) m/z: 631 (M−1). Calc'd for C$_{31}$H$_{41}$ClN$_4$O$_6$S: 633.20.

Step (b) N-[(1R)-1-[(4-Chlorophenyl)methyl]-2-(4-{2-[(methylsulfonyl)amino]phenyl}-piperidyl)-2-oxoethyl]((2S)pyrrolidin-2-yl)carboxamide The title compound was prepared according to the procedure described in Example 3, Step (b) from tert-butyl 2-{N-[(1R)-1-[(4-chlorophenyl)methyl]-2-(4-(2-[(methylsulfonyl)-amino]-phenyl)-piperidyl)-2-oxoethyl]carbamoyl}(2S)pyrrolidinecarboxylate (Step a) (315 mg, 0.5 mmol) and 50% TFA in CH$_2$Cl$_2$ (20 mL). Purification by preparative reverse phase HPLC [Phenomenex; 5 µm 250× 21.2 mm, 5% to 95% CH$_3$CN (0.1% TFA) in H$_2$O (0.1% TFA) over 30 min, then 100% CH$_3$CN (0.1% TFA) for 2 min] provided the title compound (TFA salt) as a white foam (101 mg). MS (ESI, pos. ion) m/z: 533 (M+1); (ESI, neg. ion) m/z: 531 (M−1). Calc'd for C$_{26}$H$_{33}$ClN$_4$O$_4$S: 532.19. Anal. Calcd for C$_{26}$H$_{33}$ClN$_4$O$_4$S.1.2C$_2$HF$_3$O$_2$: C, 50.92; H, 5.15; N, 8.36. Found: C, 50.82; H, 5.32; N, 8.38.

EXAMPLE 10

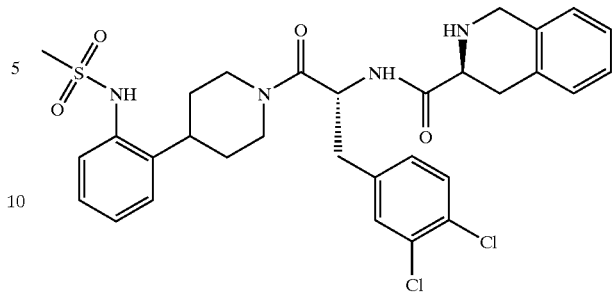

((3S)(3-1,2,3,4-Tetrahydroisoquinolyl))-N-[(1R)-1-[(3,4-dichlorophenyl)methyl]-2-(4-{2-[(methylsulfonyl)-amino]phenyl}piperidyl)-2-oxoethyl]carboxamide Step (a) N-[(1R)-1-[(3,4-Dichlorophenyl)methyl]-2-(4-{2-[(methylsulfonyl)amino]phenyl}-piperidyl)-2-oxoethyl](tert-butoxy)carboxamide The title compound was prepared according to the procedure described in Example 1 Step (f) using 4-{2-[(methylsulfonyl)amino]phenyl}piperidine (Example 1 Step e) (0.9 g, 3.1 mmol), Roc-D-3,4-diCl-Phe-OH (Advanced ChemTech) (1.04 g, 3.1 mmol), EDC (Advanced ChemTech) (0.89 g, 4.65 mmol), HOAT (Aldrich) (0.42 g, 3.1 mmol) and TEA (Aldrich) (0.65 mL, 4.65 mmol) in DMF (10 mL). Purification by silica gel chromatography (1:1 EtOAc:hexane then 100% EtOAc) provided the title compound as a pale yellow solid (0.6 g). MS (ESI, pos. ion) m/z: 570 (M+1); MS (ESI, neg. ion) m/z: 568 (M−1). Calc'd for C$_{25}$H$_{33}$Cl$_2$N$_3$O$_5$S: 570.53.

Step (b) tert-Butyl(3S)-3-{N-[(1R)-1-[(3,4-dichlorophenyl)methyl]-2-(4-{2-[(methylsulfonyl)-amino]phenyl}piperidyl)-2-oxoethyl]carbamoyl}-1,2,3,4-tetrahydroisoquinoline-2-carboxylate To a round-bottomed flask equipped with stirring was added N-[(1R)-1-[(3,4-dichlorophenyl)methyl]-2-(4-{2-[(methylsulfonyl)amino]phenyl}-piperidyl)-2-oxoethyl]-(tert-butoxy)carboxamide (Step a) (0.455 g, 0.8 mmol) and a saturated soln of anhydrous HCl in EtOAc (20 mL). The reaction mixture was stirred at RT for 1 h then concentrated in vacuo to provide a solid. The solid was dissolved in DMF (10 mL), stirred at 0° C. and treated with Boc-L-TicOH (Advanced ChemTech) (0.25 g, 0.9 mmol), HOAT (Aldrich) (0.122 g, 0.9 mmol), TEA (Aldrich) (0.188 mL, 1.35 mmol) then EDC (Advanced ChemTech) (0.26 g, 1.35 mmol). The reaction mixture was warmed to RT over 2 h, then stirred at RT for 12 h. The reaction mixture was diluted with EtOAc (70 mL), washed with satd NaHCO$_3$, (50 mL), satd NaCl (50 mL), dried over Na$_2$SO$_4$, filtered and concentrated in vacuo. Purification by silica gel chromatography (1:1 EtOAc:hexane then 100% EtOAc) provided the title compound as a white foam (0.54 g). MS (ESI, pos. ion) m/z: 729 (M+1); MS (ESI, neg. ion) m/z: 727 (M−1). Calc'd for C$_{36}$H$_{42}$Cl$_2$N$_4$O$_6$S: 728.22.

Step (c) ((3S)(3-1,2,3,4-Tetrahydroisoquinolyl))-N-[(1R)-1-[(3,4-dichlorophenyl)methyl]-2-(4-{2-[(methylsulfonyl)amino]phenyl}piperidyl)-2-oxoethyl]-carboxamide To a 150 mL round-bottomed flask equipped with stirring was added tert-butyl(3S)-3-(N-[(1R)-1-[(3,4- dichlorophenyl)methyl]-2-(4-{2-[(methylsulfonyl)-amino]phenyl)piperidyl)-2-oxoethyl]carbamoyl}-1,2,3,4-tetrahydroisoquinoline-2-carboxylate (Step b) (0.54 g, 0.74 mmol) followed by a saturated soln of HCl in EtOAc (50 mL). The reaction mixture was stirred at RT for 1 h and concentrated in vacuo to a white solid. Recrystallization from MeOH:Et$_2$O (1:20) provided the title compound (HCl salt) as a white solid (0.3 g). MP 181° C. (decomposed). MS (ESI, pos. ion) m/z: 629 (M+1); MS (ESI, neg. ion) m/z: 627 (M−1). Calc'd for $C_{31}H_{34}Cl_2N_4O_4S$: 628.17. Anal. Calcd for $C_{31}H_{34}Cl_2N_4O_4S\cdot HCl]\cdot H_2O$: C, 51.71; H, 5.74; N, 7.78; Cl, 14.77. Found: C, 51.66; H, 5.39; N, 7.49; Cl, 15.07.

EXAMPLE 11

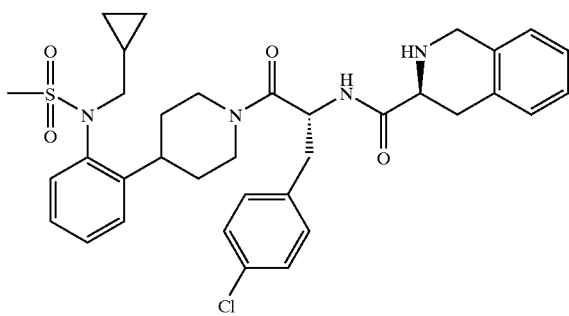

N-[(1R)-1-[(4-Chlorophenyl)methyl]-2-(4-{2-[(cyclopropylmethyl)-(methylsulfonyl)amino]-phenyl}piperidyl)-2-oxoethyl]((3S)(3-1,2,3,4-tetrahydroisoquinolyl))carboxamide Step (a) tert-Butyl 4-(2-[(cyclopropylmethyl)(methylsulfonyl)amino]phenyl}piperidine-carboxylate To a 100 mL round-bottomed flask was added tert-butyl 4-{2-[(methylsulfonyl)amino]phenyl}piperidine-carboxylate (Example 1 Step d) (1.9 grams, 5.4 mmol) and DMF (Aldrich) (30 mL). The solution was magnetically stirred vigorously at 25° C. under N$_2$ atmosphere and treated in portions with NaH as a 60% dispersion in mineral oil (Aldrich) (150 mg, 6.4 mmol). After gas evolution ceased, (bromomethyl)cyclopropane (Aldrich) (675 μL, 940 mg, 7.0 mmol) was introduced via syringe. The reaction mixture was stirred at 25° C. for 15 h. The reaction was quenched by careful addition of satd NH$_4$Cl (150 mL) and extracted with EtOAc (400 mL). The organic layer was washed with H$_2$O (150 mL), satd NaCl (100 mL), dried over Na$_2$SO$_4$, filtered and concentrated in vacuo to afford the title compound as a yellow foam (2.2 g). MS (ESI, pos. ion) m/z: 409 (M+1); (ESI, neg. ion) m/z: 407 (M−1). Calc'd for $C_{21}H_{32}N_2O_4S$: 408.56.

Step (b) N-[(1R)-1-[(4-Chlorophenyl)methyl]-2-(4-{2-[(cyclopropylmethyl)-(methylsulfonyl)amino]phenyl piperidyl)-2-oxoethyl](tert-butoxy)carboxamide To a 100 mL round-bottomed flask was added tert-butyl 4-(2-[(cyclopropylmethyl)(methylsulfonyl)amino]-phenyl}piperidine-carboxylate (Step a) (2.2 g, 5.4 mmol) and CH$_2$Cl$_2$ (20 mL). The solution was magnetically stirred and treated with TFA (Aldrich) (20 mL). After 20 min stirring, the mixture was concentrated in vacuo. The resulting yellow film was partitioned between CH$_2$Cl$_2$ (150 mL) and satd NaHCO$_3$ (50 mL). The organic layer was washed with satd NaCl (50 mL), dried over Na$_2$SO$_4$, filtered and concentrated to give a colorless oil (1.7 g).

To a separate 100 mL round-bottomed flask was added Boc-p-Cl-D-PheOH (PepTech Corporation) (2.14 g, 7.17 mmol), DMF (10 mL) and CH$_2$Cl$_2$ (10 mL). The solution was magnetically stirred at 25° C. and treated with DIEA (Aldrich) (3.13 mL, 18.2 mmol), followed by O-(7-azabenzotriazol-1-yl)-1,1,3,3-tetramethyluronium hexafluorophosphate (PerSeptive Biosystems) (2.72 g, 7.17 mmol). The resulting yellow solution was stirred for 10 min then treated with a solution of the colorless oil prepared in the previous paragraph (1.7 g, 5.5 mmol) in CH$_2$Cl$_2$ (20 mL). The reaction mixture was stirred at 25° C. for 15 h, diluted with CH$_2$Cl$_2$ (300 mL) and washed with water (75 mL), 1 M H$_3$PO$_4$ (75 mL), satd NaHCO$_3$ (75 mL), and satd NaCl (50 mL). The organic layer was dried over Na$_2$SO$_4$, filtered and concentrated in vacuo to afford a yellow oil. The oil was purified by silica gel chromatography (3:10 EtOAc:hexane) to give the title compound as a white foam (1.99 g). MS (ESI, pos. ion) m/z: 590 (M+1); (ESI, neg. ion) m/z: 588 (M−1). Calc'd for $C_{30}H_{40}ClN_3O_5S$: 590.17.

Step (c) tert-Butyl 3-{N-[(1R)-1-[(4-chlorophenyl)methyl]-2-(4-{2-[(cyclopropylmethyl)-(methylsulfonyl)amino]phenyl}piperidyl)-2-oxoethyl]carbamoyl}(3S)-1,2,3,4-tetrahydroisoquinoline-2-carboxylate To a 10 mL round-bottomed flask was added N-[(1R)-1-[(4-chlorophenyl)methyl]-2-{4-(2-[(cyclopropylmethyl)-(methylsulfonyl)amino]phenyl}-piperidyl)-2-oxoethyl]-(tert-butoxy)carboxamide (Step b) (450 mg, 0.76 mmol) and CH$_2$Cl$_2$ (3 mL). The solution was magnetically stirred and treated with TFA (Aldrich) (3 mL). After stirring 25 min, the mixture was concentrated in vacuo to a yellow film. The film was dissolved in CH$_2$Cl$_2$ (50 mL), washed with satd NaHCO$_3$ (2×25 mL), and satd NaCl (25 mL), dried over Na$_2$SO$_4$, filtered and concentrated in vacuo to afford a white foam (430 mg). The foam was dissolved in THF (20 mL), added to a 100 mL round-bottomed flask and magnetically stirred. The solution was treated with EDC (Aldrich) (259 mg, 1.35 mmol), followed by HOBT (Aldrich) (267 mg, 1.98 mmol) and Boc-L-TicOH (PepTech Corporation) (305 mg, 1.08 mmol). The reaction mixture was stirred for 18 h at 25° C., and concentrated in vacuo to a yellow residue. The residue was partitioned between EtOAc (100 mL) and 1 M H$_3$PO$_4$ (75 mL). The aqueous layer was extracted with EtOAc (2×25 mL) and the organic layers were combined, washed with 10% Na$_2$CO$_3$ (75 mL), satd NaCl (50 mL), dried over Na$_2$SO$_4$, filtered and concentrated in vacuo to afford a yellow oil. Purification by silica gel chromatography (10:25:65 MeOH:EtOAc:hexane) provided the title compound as a white foam (480 mg). MS (ESI, pos. ion) m/z: 749 (M+1); (ESI, neg. ion) m/z: 747 (M−1). Calc'd for $C_{40}H_{49}ClN_4O_6S$: 749.36.

Step (d) N-[(1R)-1-[(4-Chlorophenyl)methyl]-2-(4-{2-[(cyclopropylmethyl)-(methylsulfonyl)amino]phenyl}-piperidyl)-2-oxoethyl]((3S)(3-1,2,3,4-tetrahydroisoquinolyl))carboxamide To a 250 mL round-bottomed flask equipped with stirring was added tert-butyl 3-{N-[(1R)-1-[(4-chlorophenyl)-methyl]-2-(4-{2-[(cyclopropylmethyl)-(methylsulfonyl)-amino]phenyl}piperidyl)-2-oxoethyl]carbamoyl}(3S)-1,2,3,4-tetrahydroisoquinoline-2-carboxylate (Step c) (1.9 g, 2.5 mmol) followed by a saturated soln of HCl in EtOAc (150 mL). The mixture was stirred at RT for 1 h then concentrated

EXAMPLE 12

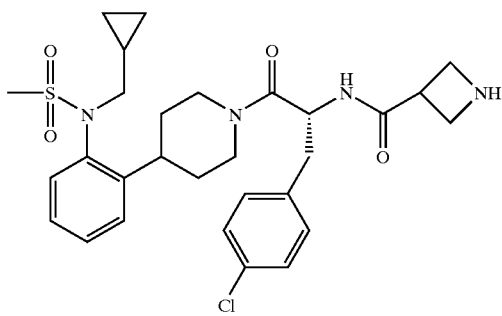

N-[(1R)-1-[(4-Chlorophenyl)methyl]-2-(4-{2-[(cyclopropylmethyl)-(methylsulfonyl)amino]phenyl)-piperidyl}-2-oxoethyl]azetidin-3-ylcarboxamide Step (a) tert-Butyl 3-(N-[(1R)-1-[(4-chlorophenyl)methyl]-2-(4-{2-[(cyclopropylmethyl)-(methylsulfonyl)amino]phenyl}piperidyl)-2-oxoethyl]carbamoyl)azetidine-carboxylate The title compound was prepared according to the procedure described in Example 11 (Step c) using N-[(1R)-1-[(4-chlorophenyl)methyl]-2-(4-{2-[(cyclopropylmethyl)-(methylsulfonyl)amino]phenyl}-piperidyl)-2-oxoethyl](tert-butoxy)carboxamide (Example 11 Step b) (450 mg, 0.76 mmol) and 50% TFA in $CH_2Cl_2$ (6 mL) followed by EDC (Aldrich) (259 mg, 1.35 mmol), HOBT (Aldrich) (270 mg, 2.0 mmol) and N-Boc-azetidine-4-carboxylic acid (PepTech Corporation) (220 mg, 1.1 mmol) in THF (20 mL). Purification by silica gel chromatography (10:25:65 MeOH:EtOAc:hexane) provided the title compound as a white foam (365 mg). MS (ESI, pos. ion) m/z: 673 (M+1); (ESI, neg. ion) m/z: 671 (M–1). Calc'd for $C_{34}H_{45}ClN_4O_6S$: 673.26.

Step (b) N-[(1R)-1-[(4-Chlorophenyl)methyl]-2-(4-{2-[(cyclopropylmethyl)-(methylsulfonyl)amino]phenyl}piperidyl)-2-oxoethyl]azetidin-3-ylcarboxamide The title compound was prepared according to the procedure described in Example 3 (Step b) using tert-butyl 3-(N-[(1R)-1-[(4-chlorophenyl)methyl]-2-(4-{2-[(cyclopropylmethyl)-(methylsulfonyl)amino]phenyl}piperidyl)-2-oxoethyl]carbamoyl)azetidine-carboxylate (Step a) (565 mg, 0.84 mmol) and 50% TFA in $CH_2Cl_2$ (6 mL). Purification by reverse phase preparative HPLC [YMC-Pack ODS-AM 250×20 mm 5 μm column, 40% to 75% $CH_3CN$ (0.1% TFA) in $H_2O$ (0.1% TFA) over 10 min] provided the title compound (TFA salt) as an amorphous white solid (420 mg). MS (ESI, pos. ion) m/z: 573 (M+1). Calcd for $C_{29}H_{37}ClN_4O_4S$: 572.22. Anal. Calcd for $C_{29}H_{37}ClN_4O_4S \cdot 1.7C_2HF_3O_2$: C, 50.74; H, 5.09; N, 7.30, S, 4.18. Found: C. 50.47; H, 5.03; N, 7.36; S, 4.28.

in vacuo to 75 mL, providing a white precipitate. The precipitate was collected by filtration and dried in vacuo to provide the HCl salt as a white solid (0.93 g). MS (ESI, pos. ion) m/z: 649 (M+1). Calc'd for $C_{35}H_{41}ClN_4O_4S$: 648.25.

Anal. Calcd for $C_{35}H_{41}ClN_4O_4S \cdot 1.1HCl \cdot 1.1H_2O$: C, 59.28; H, 6.30; N, 7.90; Cl, 10.50. Found: C, 58.95; H, 6.3; N, 7.86; Cl, 10.29. MP 190–200° C.

EXAMPLE 13

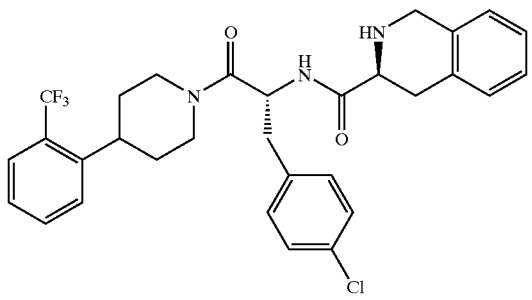

N-((1R)-1-[(4-Chlorophenyl)methyl]-2-oxo-2-{4-[2-(trifluoromethyl)phenyl]-piperidyl}ethyl)((3S)(3-1,2,3,4-tetrahydroisoquinolyl))carboxamide Step (a) tert-Butyl 4-[2-(trifluoromethyl)phenyl]-1,2,5,6-tetrahydropyridinecarboxylate The title compound was prepared according to the procedure described in Preparation A using 2-(trifluoromethyl)phenylboronic acid (Aldrich) (1.89 g, 10 mmol), tert-butyl 4-[(trifluoromethyl)sulfonyloxy]-1,2,5,6-tetrahydropyridinecarboxylate [prepared by the method of Wustrow, D. J. and Wise, L. D., *Synthesis*, 1991, 993–995, from tert-butyl-4-oxopiperidine-1-carboxylate (Aldrich), LDA (Aldrich) and N-phenyltrifluoromethanesulfonimide (Aldrich)] (3.64 g, 11 mmol), tetrakis(triphenylphosphine) palladium (0) (Strem Chemicals) (0.578 g, 0.5 mmol), LiCi (Aldrich) (1.27g, 30 mmol), and $Na_2CO_3$ (Aldrich) (2.46 g, 30 mmol) in water (15 mL) and DME (20 mL). Purification by silica gel chromatography (5:1 hexane:EtOAc) provided the title compound as a white foam (2.01 g). MS (ESI, pos. ion) m/z: 328 (M+1); MS (ESI, neg. ion) m/z: 326 (M–1). Calc'd for $C_{17}H_{20}F_3NO_2$: 327.34.

Step (b) tert-Butyl 4-[2-(trifluoromethyl)phenyl]piperidinecarboxylate

The title compound was prepared according to the procedure described in Preparation B from tert-butyl 4-[2-(trifluoromethyl)phenyl]-1,2,5,6-tetrahydro pyridinecarboxylate (Step a) (1.96 g, 6.0 mmol) and 10% Pd/C (Aldrich) (0.5 g) in EtOH (30 mL) under 50 psi $H_2$. The title compound was obtained as white foam (1.87). MS (ESI, pos. ion) m/z: 330 (M+1); MS (ESI, neg. ion) m/z: 328 (M–1). Calc'd for $C_{17}H_{22}F_3NO_2$: 329.36.

Step (c) 4-[2-(Trifluoromethyl)phenyl]piperidine Hydrochloride

The title compound was prepared according to the procedure described in Example 1 (Step e) from tert-butyl 4-[2-(trifluoromethyl)phenyl]piperidine carboxylate (Step b) (1.64 g, 5 mmol) and satd HCl in EtOAc (50 m[). The title compound was obtained as a white solid (1.32 g). MS (ESI, pos. ion) m/z: 230 (M+1); MS (ESI, neg. ion) m/z: 228 (M–1). Calc'd for $C_{12}H_{15}CF_3N$: 265.70.

Step (d) N-((1R)-1-[(4-Chlorophenyl)methyl]-2-oxo-2-{4-[2-(trifluoromethyl}phenyl]-piperidyl)ethyl)(tert-butoxy)carboxamide The title compound was prepared according to the procedure described in Example 1 (Step f) from 4-[2-(trifluoromethyl)phenyl]piperidine hydrochloride (Step c)

(0.792 g, 3.0 mmol), DIEA (0.54 mL, 3.0 mmol), Boc-p-Cl-D-PheOH (PepTech Corporation) (1.36 g, 4.5 mmol), HOAT (Aldrich) (0.615 g, 4.5 mmol) and EDC (Aldrich) (0.864 g, 4.5 mmol) in DMF (5 mL). Purification by silica gel chromatography (5:2 hexane:EtOAc) provided the title compound as a white foam (1.06 g). MS (ESI, pos. ion) m/z: 511 (M+1); MS (ESI, neg. ion) m/z: 509 (M−1). Calc'd for $C_{26}H_{30}ClF_3N_2O_3$: 510.98.

Step (e) (2R)-2-Amino-3-(4-chlorophenyl)-1-{4-[2-(trifluoromethyl)phenyl]-piperidyl}propan-1-one hydrochloride The title compound was prepared according to the procedure described in Example 1 (Step e) from N-((1R)-1-[(4-chlorophenyl)methyl]-2-oxo-2-{4-[2-(trifluoromethyl)phenyl]-piperidyl}ethyl)(tert-butoxy)-carboxamide (Step d) (1.02 g, 2.0 mmol) and satd HCl in EtOAc (50 mL). The title compound was obtained as white solid (0.89 g). MS (ESI, pos. ion) m/z: 411 (M+1); MS (ESI, neg. ion) m/z: 409 (M−1). Calc'd for $C_{21}H_{22}ClF_3N_2O$: 410.14.

Step (f) tert-Butyl 3-[N-((1R)-1-[(4-chlorophenyl)methyl]-2-oxo-2-{4-[2-(trifluoromethyl)-phenyl]piperidyl}-ethyl)carbamoyl](3S)-1,2,3,4-tetrahydroisocquinoline-2-carboxylate The title compound was prepared according to the procedure described in Example 1 (Step f) from (2R)-2-amino-3-(4-chlorophenyl)-1-{4-[2-(trifluoromethyl)-phenyl]-piperidyl}propan-1-one hydrochloride (Step e) (890 mg, 2.0 mmol), DIEA (0.40 mL, 2.0 mmol), Boc-L-TicOH (Bachem Company) (544 mg, 2.8 mmol), HOAT (Aldrich) (382 mg, 2.8 mmol) and EDC (Aldrich) (544 mg, 2.84 mmol) in DMF (10 mL). Purification by silica gel chromatography (5:2 hexane:EtOAc) provided the title compound as a white foam (702 mg). MS (ESI, pos. ion) m/z: 670 (M+1); MS (ESI, neg. ion) m/z: 668 (M−1). Calc'd for $C_{36}H_{39}ClF_3N_3O_4$: 669.26.

Step (g) N-((1R)-1-[(4-Chlorophenyl)methyl]-2-oxo-2-{4-[2-(trifluoromethyl)phenyl]-piperidyl}ethyl)((3S)(3-1,2,3,4-tetrahydroisoquinolyl))carboxamide Trifluoroacetate The title compound was prepared according to the procedure described in Example 3 (Step b) from tert-butyl 3-[N-((1R)-1-[(4-chlorophenyl)methyl]-2-oxo-2-{4-[2-(trifluoromethyl)-phenyl]piperidyl}ethyl)-carbamoyl](3S)-1,2,3,4-tetrahydroisoquinoline-2-carboxylate (Step f) (335 mg, 0.5 mmol) and 50% TFA in $CH_2Cl_2$ (20 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white solid (202 mg). MS (ESI, pos. ion) m/z: 570 (M+1); (ESI, neg. ion) m/z: 568 (M−1). Calc'd for $C_{31}H_{31}ClF_3N_3O_2$: 569.21.

EXAMPLE 14

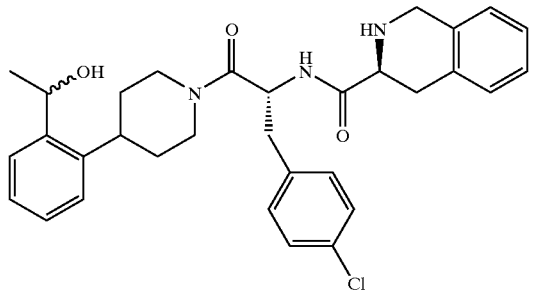

N-((1R)-1-[(4-Chlorophenyl)methyl]-2-{4-[2-(hydroxyethyl)phenyl]piperidyl}-2-oxoethyl)((3S)(3-1,2,3,4-tetrahydroisoquinolyl))carboxamide Step (a) tert-Butyl 4-(2-acetylphenyl)-1,2,5,6-tetrahydropyridinecarboxylate The title compound was prepared according to the procedure described in Preparation A using 2-acetylphenylboronic acid (Aldrich) (1.63 g, 10 mmol), tert-butyl 4-[(trifluoromethyl)sulfonyloxy]-1,2,5,6-tetrahydropyridinecarboxylate [prepared by the method of Wustrow, D. J. and Wise, I. D. *Synthesis*, 1991, 993-995, from tert-butyl-4-oxopiperidine-1-carboxylate (Aldrich), LDA (Aldrich) and N-phenyltrifluoromethane-sulfonimide (Aldrich)) (3.64 g, 11 mmol), tetrakis(triphenylphosphine) palladium (0) (Strem Chemicals) (0.578 g, 0.5 mmol), LiCl (Aldrich) (1.27g, 30 mmol), and $Na_2CO_3$ (Aldrich) (2.46 g, 30 mmol) in water (15 mL) and DME (20 mL). Purification by silica gel chromatography (5:1 hexane:EtOAc) provided the title compound as a white foam (1.77 g). MS (ESI, pos. ion) m/z: 302 (M+1); MS (ESI, neg. ion) m/z: 300 (M−1). Calc'd for $C_{18}H_{23}NO_3$: 301.38.

Step (b) tert-Butyl 4-[2-(hydroxyethyl)phenyl]piperidinecarboxylate

The title compound was repared according to the procedure described in Preparation B using tert-butyl 4-(2-acetylphenyl)-1,2,5,6-tetrahydropyridine carboxylate (Step a) (1.51 g, 5.0 mmol) and 10% Pd/C (Aldrich) (0.5 g) in MeOH (30 mL) under 50 psi $H_2$ for 48 h. The title compound was obtained as a white foam (1.49 g). MS (ESI, pos. ion) m/z: 306 (M+1); MS (ESI, neg. ion) m/z: 304 (M−1). Calc'd for $C_{18}H_{27}NO_3$: 305.41.

Step (c) 1-(2-(4-Piperidyl)phenyl)ethan-1-ol hydrochloride

The title compound was prepared according to the procedure described in Example 1 (Step e) using tert-butyl 4-(2-(hydroxyethyl)phenyl]piperidinecarboxylate (Step b) (1.22 g, 4.0 mmol) and satd anhydrous HCl in EtOAc (50 mL). The title compound was obtained as a white solid (0.96 g). MS (ESI, pos. ion) m/z: 206 (M+1); MS (ESI, neg. ion) m/z: 204 (M−1). Calc'd for $C_{13}H_{19}NO$: 205.15.

Step (d) N-((1R)-1-[(4-Chlorophenyl)methyl]-2-{4-[2-(hydroxyethyl)phenyl]piperidyl}-2-oxoethyl)(tert-butoxy)carboxamide The title compound was prepared according to the procedure described in Example 1 (Step f) using 1-(2-(4-piperidyl)phenyl)ethan-1-ol hydrochloride (Step c) (0.72 g, 3.0 mmol), DIEA (0.54 mL, 3.0 mmol), Boc-p-Cl-D-PheOH (PepTech Corporation) (1.36 g, 4.5 mmol), HOAT (Aldrich) (0.615 g, 4.5 mmol) and EDC (Aldrich) (0.864 g, 4.5 mmol) in DMF (5 mL). Purification by silica gel chromatography (100% EtOAc) provided the title compound as a white foam (1.09 g). MS (EST, pos. ion) m/z: 487 (M+1); MS (ESI, neg. ion) m/z: 485 (M−1). Calc'd for $C_{27}H_{35}ClN_2O_4$: 486.23.

Step (e) (2R)-2-Amino-3-(4-chlorophenyl)-1-{4-[2-(hydroxyethyl)phenyl]piperidyl}-propan-1-one hydrochloride The title compound was prepared according to the procedure described in Example 1 (Step e) using N-((1R)-1-[(4-chlorophenyl)methyl]-2-(4-[2-(hydroxyethyl)phenyl]piperidyl)-2-oxoethyl)(tert-butoxy)carboxamide (Step d) (0.976 g, 2.0 mmol) and satd anhydrous HCl in EtOAc (30 mL). The title compound was obtained as a white solid (0.846 g). MS (ESI, pos. ion) m/z: 387 (M+1) MS (EST, neg. ion) m/z: 385 (M−1). Calc'd for $C_{22}H_{27}ClN_2O_2$: 386.18.

Step (f) tert-Butyl 3-[N-((1R)-1-[(4-chlorophenyl)methyl]-2-{4-[2-(hydroxyethyl)phenyl]-piperidyl}-2-oxoethyl)carbamoyl](3S)-1,2,3,4-tetrahydroisoquinoline-2-carboxylate The title compound was prepared according to the procedure described in Example 1 (Step f) using (2R)-2-amino-3-{4chlorophenyl)-1-(4-[2-(hydroxyethyl)phenyl]-piperidyl}-propan-1-one hydrochloride (Step e) (846 mg, 2.0 mmol), DIEA (0.40 mL, 2.0 mmol), Boc-L-TicOH (Bachem Company) (544 mg, 2.8 mmol), HOAT (Aldrich) (382 mg, 2.8 mmol) and EDC (Aldrich) (544 mg, 2.84 mmol) in DMF (10 mL). Purification by silica gel chromatography (100% EtOAc) provided the title compound as a white foam (739 mg). MS (EST, pos. ion) m/z: 646 (M+1); MS (ESI, neg. ion) m/z: 644 (M−1). Calc'd for $C_{37}H_{44}ClN_3O_5$: 645.30.

Step (g) N-((1R)-1-[(4-Chlorophenyl)methyl]-2-{4-[2-(hydroxyethyl)phenyl]piperidyl)-2-oxoethyl)((3s)(3-1,2,3,4-tetrahydroisoquinolyl))carboxamide The title compound was prepared according to the procedure described in Example 3 (Step b) using tert-butyl 3-[N-((1R)-1-[(4-chlorophenyl)methyl]-2-(4-[2-(hydroxyethyl)phenyl]-piperidyl]-2-oxoethyl)carbamoyl]-(3S)-1,2,3,4-tetrahydroisoquinoline-2-carboxylate (Step f) (323 mg, 0.5 mmol) and 50% TFA in $CH_2Cl_2$ (20 mL). Purification by reverse phase preparative HPLC (Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white solid (145 mg). MS (ESI, pos. ion) m/z: 546 (M+1); (ESI, neg. ion) m/z: 544 (M−1). Calc'd for $C_{32}H_{36}ClN_3O_3$: 545.24.

EXAMPLE 15

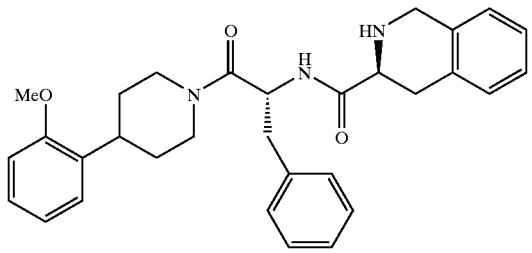

((3S)(3-1,2,3,4-Tetrahydroisoquinolyl))-N-{(1R)-2-[4-(2-methoxyphenyl)-piperidyl]-2-oxo-1-benzylethyl}carboxamide

Step (a) N-{(1R)-2-[4-(2-Methoxyphenyl) piperidyl]-2-oxo-1-benzylethyl}(tert-butoxy) carboxamide The title compound was prepared according to the procedure described in Example 1 (Step f) using 4-(2-methoxyphenyl)piperidine (Maybridge) (2.68 g, 0.014 mol), Boc-D-PheOH (Advanced ChemTech) (3.71 g, 0.014 mmol), HOAT (Aldrich) (1.9 g, 0.014 mol) and EDC (Advanced ChemTech) (4.02 g, 0.021 mol). Purification by silica gel chromatography (1:1 EtOAc:hexane) provided the title compound as a colorless oil (5.0 g). MS (ESI, pos. ion) m/z: 439 (M+1). Calc'd for $C_{26}H_{34}N_2O_4$: 438.56.

Step (b) tert-Butyl(3S)-3-(N-{(1R)-2-[4-(2-methoxyphenyl)piperidyl]-2-oxo-1-benzylethyl}carbamoyl)-1,2,3,4-tetrahydroisoquinoline-2-carboxylate The title compound was prepared according to the procedure described in Example 10 (Step b) using N-{(1R)-2-[4-(2-methoxyphenyl)piperidyl]-2-oxo-1-benzylethyl}(tert-butoxy)carboxamide (Step a) (5.0 g, 11 mmol) and satd anhydrous HCl in EtOAc (70 mL) which provided a white solid (4.11 g, 100%). A portion of the white solid (1.2 g, 3.2 mmol) was treated with Boc-L-TicOH (Advance ChemTech) (0.887 g, 3.2 mmol), HOAT (Aldrich) (0.435 g, 3.2 mmol), TEA (Aldrich) (0.67 mL, 4.8 mmol) and EDC (Advanced ChemTech) (0.92 g, 4.8 mmol). Purification by silica gel chromatography (1:1 EtOAc:hexane then 100% EtOAc) provided the title compound as a white foam (1.4 g). MS (ESI, pos. ion) m/z: 598 (M+1); (ESI, neg. ion) m/z: 596 (M−1). Calc'd for $C_{36}H_{43}N_3O_5$: 597.32.

Step (c) ((3S)(3-1,2,3,4-Tetrahydroisoquinolyl))-N-((1R)-2-[4-(2-methoxyphenyl)-piperidyl]-2-oxo-1-benzylethyl}carboxamide The title compound was prepared according to the procedure described in Example 3 (Step b) from tert-butyl (3S)-3-(N-((1R)-2-[4-(2-methoxyphenyl)piperidyl]-2-oxo-1-benzylethyl]carbamoyl)-1,2,3,4-tetrahydro-isoquinoline-2-carboxylate (Step b) (1.4 g, 2.34 mmol) and 50% TFA in $CH_2Cl_2$ (80 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 10U % $CH_3CN$ (0.1% TFA) for 2 min] provided the title compound (TFA salt) as a white foam (0.5 g). MS (ESI, pos. ion) m/z: 498 (M+1). Calc'd for $C_{31}H_{35}N_3O_3$: 497.27.

EXAMPLE 16

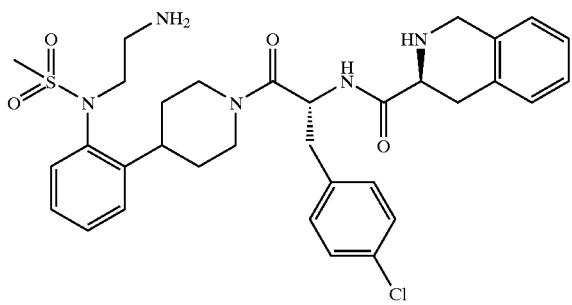

N-[(1R)-2-(4-{(2-[(2-Aminoethyl)(methylsulfonyl)amino]phenyl}piperidyl)-1-[(4-chlorophenyl)methyl]-2-oxoethyl]((3S)(3-1,2,3,4-tetrahydroisoquinolyl))-carboxamide

Step (a) tert-Butyl 4-(2-{[2-(1,3-dioxoisoindolin-2-yl)ethyl](methylsulfonyl)-amino}phenyl)piperidinecarboxylate To a 250 mL round-bottomed flask equipped with stirring was added tert-butyl 4-{2-[(methylsulfonyl)-amino]phenyl}piperidine-carboxylate (Example 1 Step d) (2.12 g, 6.0 mmol), DMF (100 mL), N-(2-bromomethyl)-phthalimide (Aldrich) (4.57 g, 18 mmol) and $K_2CO_3$ (Aldrich) (7.45 g, 54 mmol). The mixture was stirred at 75° C. for 24 h, filtered and concentrated in vacuo to afford a yellow oil. The oil was dissolved in a 1:1 mixture of EtOAc in THF (100 mL), washed with 0.1 M HCl (100 mL), satd NaCl (100 mL), dried over $Na_2SO_4$, filtered and concentrated in vacuo. The residue was purified by silica gel chromatography (1:1 hexane:EtOAc) to provide the title compound as a white foam (1.98 g). MS (ESI, pos. ion) m/z: 528 (M+1); MS (ESI, neg. ion) m/z: 526 (M−1). Calc'd for $C_{27}H_{33}N_3O_6S$: 527.21.

Step (b) 2-{2-[(Methylsulfonyl)(2-(4-piperidyl)phenyl)amino]ethyl}isoindoline-1,3-dione hydrochloride To a 150 mL round-bottomed flask equipped with stirring was added tert-butyl 4-(2-{[2-(1,3-dioxo-isoindolin-2-yl)ethyl](methylsulfonyl)-amino}-phenyl)-piperidinecarboxylate (Step a) (1.58 g, 3 mmol) and EtOAc (5 mL). The mixture was treated with a satd solution of anhydrous HCl in EtOAc (70 mL) at 0° C. The reaction mixture was warmed to RT and stirred for 3 h. The solvent was removed in vacuo to provide the title compound as a white foam (1.38 g). MS (ESI, pos. ion) m/z: 428 (M+1); MS (ESI, neg. ion) m/z: 426 (M−1). Calc'd for $C_{22}H_{25}N_3O_4S$: 427.16.

Step (c) N-{(1R)-2-[4-(2-{[2-(1,3-Dioxoisoindolin-2-yl)ethyl](methylsulfonyl)-amino)phenyl)-piperidyl]-1-[(4-chlorophenyl)methyl]-2-oxoethyl}(tert-butoxy)carboxamide The title compound was prepared according to the procedure described in Example 1, (Step f) from 2-(2-[(methylsulfonyl)(2-(4-piperidyl)phenyl)amino]ethyl)isoindoline-1,3-dione hydrochloride (Step b) (1.28 g, 2.8 mmol), DIEA (0.54 mL, 3.0 mmol), Boc-p-Cl-D-PheOH (PepTech Corporation) (1.36 g, 4.5 mmol), HOAT (Aldrich) (0.615 g, 4.5 mmol) and EDC (Aldrich) (0.864 g, 4.5 mmol) in DMF (15 mL). Purification by silica gel chromatography (1:1 hexane:EtOAc) provided the title compound as a white foam (1.83 g %). MS (ESI, pos. ion) m/z: 709 (M+1); MS (ESI, neg. ion) m/z: 707 (M−1). Calc'd for $C_{36}H_{41}ClN_4O_7S$: 708.24.

Step (d) 2-{2-[(2-(1-[(2R)-2-Amino-3-(4-chlorophenyl)propanoyl](4-piperidyl))phenyl)-(methylsulfonyl)amino]ethyl}isoindoline-1,3-dione Hydrochloride The title compound was prepared according to the procedure described in (Step b) from N-((1R)-2-[4-(2-{[2-(1,3-dioxoisoindolin-2-yl)ethyl](methylsulfonyl)-amino}phenyl)-piperidyl]-1-[(4-chlorophenyl)methyl]-2-oxoethyl)(tert-butoxy)carboxamide (Step c) (1.77 g, 2.5 mmol) and satd anhydrous HCl in EtOAc (50 mL). The title compound was obtained as a white solid (1.61 g). MS (ESI, pos. ion) m/z: 609 (M+1); MS (ESI, neg. ion) m/z: 607 (M−1). Calc'd for $C_{31}H_{14}Cl_2N_4O_5S$: 645.60.

Step (e) tert-Butyl 3-(N-{(1R)-2-[4-(2-{[2-(1,3-dioxoisoindolin-2-yl)ethyl](methylsulfonyl)-amino}phenyl)piperidyl]-1-[(4-chlorophenyl)methyl]-2-oxoethyl}carbamoyl)(3S)-1,2,3,4-tetrahydroisoquinoline-2-carboxylate The title compound was prepared according to the procedure described in Example 1 (Step f) using 2-{2-[(2-[(2R)-2-amino-3-(4-chlorophenyl)propanoyl](4-piperidyl)})phenyl)-(methylsulfonyl)amino]ethyl)isoindoline-1,3-dione hydrochloride (Step d) (643 mg, 1.0 mmol), DIEA (0.20 mL, 1.0 mmol), Boc-L-TicOH (Bachem Company) (394 mg, 1.42 mmol), HOAT (Aldrich) (232 mg, 1.70 mmol) and EDC (Aldrich) (544 mg, 2.84 mmol) in DMF (5 mL). Purification by silica gel chromatography (3:2 hexane:EtOAc) provided the title compound as a white foam (628 mg). MS (ESI, pos. ion) m/z: 868 (M+I); MS (ESI, neg. ion) m/z-866 (M−1). Calc'd for $C_{46}H_{50}ClN_5O_8S$: 867.31.

Step (f) tert-Butyl 3-{N-[(1R)-2-(4-{2-[(2-aminoethyl)(methylsulfonyl)amino]-phenyl}-piperidyl)-1-[(4-chlorophenyl)methyl]-2-oxoethyl]carbamoyl}(3S)-1,2,3,4-tetrahydroisoquinoline-2-carboxylate To a 50 mL round-bottomed flask equipped with stirring was added a solution of tert-butyl 3-(N-((1R)-2-[4-(2-{[2-(1,3-dioxoisoindolin-2-yl)ethyl](methylsulfonyl)-amino}phenyl)piperidyl]-1-[(4-chlorophenyl)methyl]-2-oxoethyl)carbamoyl)(3S)-1,2,3,4-tetrahydroisoquinoline-2-carboxylate (Step e) (433.5 mg, 0.5 mmol) in 3:1 EtOH:1,2-dichloroethane (15 mL) followed by hydrazine (Aldrich) (49 mg, 1.5 mmol). The reaction mixture was stirred at 60° C. for 12 h. The organic solvents were removed in vacuo to provide a white solid which was dissolved in EtOAc (20 mL) and washed with satd $NaHCO_3$ (20 mL) and satd NaCl (20 mL). The organic layer was dried over $Na_2SO_4$, filtered and concentrated in vacuo. Purification by silica gel chromatography (100% EtOAc) provided the title compound as a white foam (349 mg). MS (ESI, pos. ion) m/z: 738 (M+1); MS (ESI, neg. ion) m/z: 736 (M−1). Calc'd for $C_{38}H_{48}ClN_5O_6S$: 737.30.

Step (g) N-[(1R)-2-(4-{2-[(2-Aminoethyl)(methylsulfonyl)amino]phenyl)piperidyl)-1-[(4-chlorophenyl)methyl]-2-oxoethyl]((3S)(3-1,2,3,4-tetrahydroisoquinolyl))-carboxamide The title compound was prepared according to the procedure described in Example 3 (Step b) from tert-butyl 3-{N-[(1R)-2-(4-(2-[(2-aminoethyl)-(methylsulfonyl)amino]phenyl}piperidyl)-1-[(4-chlorophenyl)methyl]-2-oxoethyl]carbamoyl}(3S)-1,2,3,4-tetrahydroisoquinoline-2-carboxylate (Step f) (294.8 mg, 0.4 mmol) and 50% TFA in $CH_2Cl_2$ (20 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white solid (224 mg). MS (ESI, pos. ion) m/z: 638 (M+1); (ESI, neg. ion) m/z: 636 (M−1). Calc'd for $C_{33}H_{40}ClN_5O_4S$: 637.25. Anal. Calcd for $C_{33}H_{40}ClN_5O_4S.2.5C_2H_3O_2$: C, 49.43; H, 4.64; N, 7.41. Found: C, 49.39; H, 4.78; N, 7.58.

EXAMPLE 17

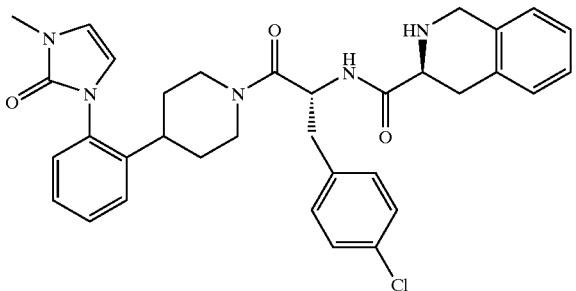

((3S)(3-1,2,3,4-Tetrahydroisoquinolyl))-N-((1R)-1-[(4-chlorophenyl)methyl]-2-{4-[2-(3-methyl-2-oxo(4-imidazolinyl))phenyl]piperidyl}-2-oxoethyl)carboxamide Step (a) tert-Butyl 4-(2-{[(2,2-dimethoxyethyl)methyl-amino]carbonylamino}-phenyl)piperidinecarboxylate The title compound was prepared according to the procedures described by WO01/44230, Wong, O. et al. (*Heterocycles* 1987, 26, 3153–8) and Ciufolini and Xi, J. Org. Chem., 62, 2320–21 (1997). To a 50 mL round-bottomed flask equipped with stirring was added Preparation B (0.85 g, 3.08 mmol), N,N'-disuccinimidyl carbonate (Aldrich) (1.57 g, 6.16 mmol) and DMF (10 mL). The reaction mixture was stirred for 12 h at RT. A solution of methylaminoacetaldehyde dimethylacetal (1.0 mL, 7.78 mmol) (Aldrich) in 5:2 DMF:$CH_2Cl_2$ (7 mL) was added via syringe and stirring was continued for an additional 12 h. The reaction mixture was diluted with EtOAc (50 mL) and the organic phase washed with satd $NaHCO_3$ (40 mL), satd NaCl (40 mL), dried over $Na_2SO_4$ and concentrated in vacuo. Purification by silica gel chromatography (1:1 EtOAc:hexane then 100% EtOAc) provided the title compound as a yellow oil (1.04 g). MS (ESI, pos. ion) m/z: 422 (M+1). Calc'd for $C_{22}H_{35}N_3O_5$: 421.26.

Step (b) N-((1R)-1-[(4-Chlorophenyl)methyl]-2-{4-[2-(3-methyl-2-oxo(4-imidazolinyl))-phenyl]piperidyl}-2-oxoethyl)(tert-butoxy)carboxamide To a 150 mL round-bottomed flask equipped with stirring was added tert-butyl 4-(2-{[(2,2-dimethoxyethyl)methylamino]carbonylamino}phenyl)-piperidinecarboxylate (Step a) (1.4 g, 3.3 mmol) and a 50% aqueous TFA soln (50 mL). The reaction mixture was stirred at RT for 2 h, then concentrated in vacuo. The residue was dissolved in $CH_2Cl_2$ (10 mL), stirred at 0° C. and treated with Boc-p-Cl-D-PheOH (Advanced ChemTech) (0.94 g, 3.15 mmol), HOBT (Novabiochem) (0.425 g, 3.15 mmol), TEA (Aldrich) (0.44 mL, 3.15 mmol) and EDC (Advanced ChemTech) (0.91 g, 4.7 mmol). The reaction was warmed to RT over 2 h and stirred at RT for 12 h. The reaction mixture was diluted with $CH_2Cl_2$ (60 mL) and the organic phase was washed with satd $NaHCO_3$ (50 mL), and satd NaCl (50 mL), dried over $Na_2SO_4$, and concentrated in vacuo. Purification by silica gel chromatography (100% EtOAc) provided the title compound as a pale yellow oil (0.55 g). MS (ESI, pos. ion) m/z: 539 (M+1). Calc'd for $C_{29}H_{35}ClN_4O_4$: 538.23.

Step (c) tert-Butyl(3S)-3-[N-((1R)-1-[(4-chlorophenyl)methyl]-2-{4-[2-(3-methyl-2-oxo(4-imidazolinyl))phenyl]piperidyl}-2-oxoethyl)carbamoyl]-1,2,3,4-tetrahydroisoquinoline-2-carboxylate The title compound was prepared according to the procedure described in Example 10 (Step b) using N-((1R)-1-[(4-chlorophenyl)methyl]-2-{4-[2-(3-methyl-2-oxo(4-imidazolinyl))-phenyl]piperidyl}-2-oxoethyl)(tert-butoxy)carboxamide (Step b) (0.237 g, 0.44 mmol) and satd anhydrous HCl in EtOAc, followed by Boc-L-TicOH (Advanced ChemTech) (0.123 g, 0.44 mmol), HOAT (Aldrich) (0.06 g, 0.44 mmol), TEA (Aldrich) (0.06 mL, 0.44 mmol) and EDC (Advanced ChemTech) (0.126 g, 0.66 mmol) in DMF (10 mL). Purification by silica gel chromatography (EtOAc then 1:9 MeOH:EtOAc) provided the title compound as a pale yellow foam (0.12 g). MS (ESI, pos. ion) m/z: 698 (M+1). Calc'd for $C_{39}H_{44}ClN_5O_5$: 697.30.

Step (d) ((3S)(3-1,2,3,4-Tetrahydroisoquinolyl))-N-((1R)-1-[(4-chlorophenyl)methyl]-2-{4-[2-(3-methyl-2-oxo(4-imidazolinyl))phenyl]piperidyl}-2-oxoethyl)carboxamide The title compound was prepared according to the procedure described in Example 10 (Step c) from tert-butyl (3S)-3-[N-((1R)-1-[(4-chlorophenyl)methyl]-2-(4-[2-(3-methyl-2-oxo(4-imidazolinyl))phenyl]piperidyl)-2-oxoethyl)carbamoyl]-1,2,3,4-tetrahydroisoquinoline-2-carboxylate (Step c) (0.12 g, 0.17 mmol) and satd anhydrous HCl in EtOAc (50 mL). Recrystallization from 1:10 $CH_2Cl_2$:$Kt_2O$ provided the title compound (HCl salt) as a white solid (0.06 g). MP 178° C. (decomposed). MS (ESI, pos. ion) m/z: 598 (M+1). Calc'd for $C_{34}H_{36}ClN_5O_3$: 597.25. Anal. Calcd for $C_{34}H_{35}ClN_5O_3.HCl.1.25H_2O$—C, 62.15; H, 6.06; N, 10.66; Cl, 10.79. Found: C, 62.20; H, 6.02; N, 10.68; Cl, 10.65.

EXAMPLE 18

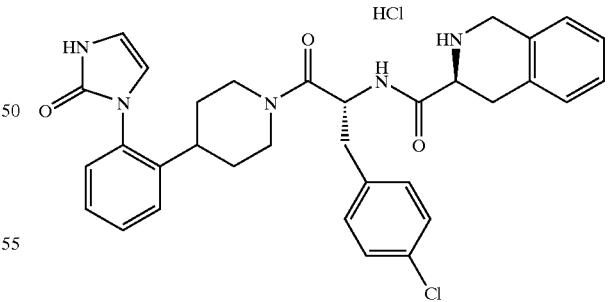

((3S)(3-1,2,3,4-Tetrahydroisoquinolyl))-N-((1R)-1-[(4-chlorophenyl)methyl]-2-oxo-2-{4-[2-(2-oxo(4-imidazolinyl))phenyl]piperidyl}ethyl)carboxamide Step (a) tert-Butyl 4-(2-{[(2,2-dimethoxyethyl)amino]-carbonylamino}phenyl)piperidine-carboxylate The title compound was prepared according to the procedure described in Example 17 (Step a) WO01/44230, Wong, O. et al. (*Heterocyclcs* 1987, 26, 3153–8) and Ciufolini and Xi, J. Org. Chem., 62, 2320–21 (1997) from Lert-butyl 4-(2-aminophenyl)piperidinecarboxylate (0.85 g, 3.08 mmol), N,N'-disuccinimidyl carbonate (Aldrich) (1.57 g, 6.16 mmol) and aminoacetylaldehyde dimethylacetal (Aldrich) (1.0 mL, 9.18 mmol). Purification by silica gel chromatography (1:1 EtOAc:hexane then 100% EtOAc) provided the title compound as a yellow oil (0.742 g). MS (ESI, pos. ion) m/z: 408 (M+1). Calc'd for $C_{21}H_{33}N_3O_5$: 407.24.

Step (b) N-((1R)-1-[(4-Chlorophenyl)methyl]-2-oxo-2-{4-[2-(2-oxo(4-imidazolinyl))phenyl]-piperidyl}ethyl)(tert-butoxy) carboxamide The title compound was prepared according to the procedure described in Example 17 (Step b) using tert-butyl 4-(2-{[(2,2-dimethoxyethyl)amino]carbonylamino}phenyl)piperidine-carboxylate (Step a) (0.742 g, 1.82 mmol) and a 50% aqueous TFA soln (20 mL) followed by Boc-p-Cl-D-PheOH (Advanced ChemTech) (0.545 g, 1.82 mmol), EDC (Advanced ChemTech) (0.523 g, 2.73 mmol), HOBT (Novabiochem) (0.246 g, 1.82 mmol) and TFA (Aldrich) (0.25 mL, 1.82 mmol) in $CH_2Cl_2$ (10 mL). Purification by silica gel chromatography (100% EtOAc then 1:9 MeOH:EtOAc) provided the title compound as a white solid (0.675 g). MS (ESI, pos. ion) m/z: 525 (M+1). Calc'd for $C_{28}H_{33}ClN_4O_4$: 524.22.

Step (c) tert-Butyl(3S)-3-[N-((1R)-1-[(4-chlorophenyl)methyl]-2-oxo-2-{4-[2-(2-oxo(4-imidazolinyl))phenyl]piperidyl}ethyl)carbamoyl]-1,2,3,4-tetrahydroisoquinoline-2-carboxylate The title compound was prepared according to the procedure described in Example 10 (Step b) using N-((1R)-1-[(4-chlorophenyl)methyl]-2 oxo-2-{4-[2-(2-oxo(4-imidazolinyl))phenyl]-piperidyl}ethyl)(tert butoxy) carboxamide (Step b) (0.283 g, 0.54 mmol) and satd anhydrous HCl in EtOAc, followed by Boc-L-TicOH (Advanced ChemTech) (0.18 g, 0.65 mmol), EDC (Advanced ChemTech) (0.155 g, 0.81 mmol), HOBT (Novabiochem) (0.073 g, 0.54 mmol) and TEA (Aldrich) (0.075 mL, 0.54 mmol) in $CH_2Cl_2$ (10 mL). Purification by silica gel chromatography (100% EtOAc then 1:9 MeOH:EtOAc) provided the title compound as a white foam (0.3 g). MS (ESI, pos. ion) m/z: 684 (M+1). Calc'd for $C_{38}H_{42}ClN_5O_5$: 683.29.

Step (d) ((3S)(3-1,2,3,4-Tetrahydroisoquinolyl))-N-((1R)-1-[(4-chlorophenyl)methyl]-2-oxo-2-{4-[2-(2-oxo(4-imidazolinyl))phenyl]piperidyl}ethyl) carboxamide The title compound was prepared according to the procedure described in Example 10 (Step c) from tert-butyl (3S)-3-[N-((1R)-1-[(4-chlorophenyl)methyl]-2-oxo-2-(4-[2-(2-oxo(4-imidazolinyl))phenyl]piperidyl)ethyl) carbamoyl]-1,2,3,4-tetrahydroisoquinoline-2-carboxylate (Step c) (0.3 g, 0.44 mmol) and satd anhydrous HCl in EtOAc (20 mL). Recrystallization from 1:20 MeOH:$Et_2O$ provided the title compound (HCl salt) as a white solid (0.15 g). MP 191° C. (decomposed). MS (ESI, pos. ion) m/z: 584 (M+1). Calc'd for $C_{33}H_{34}ClN_5O_3$: 597.25. Anal. Calcd for $C_{33}H_{34}ClN_5O_3HCl.2.25H_2O$: C, 59.95; H, 6.02: N, 10.59; Cl, 10.13. Found: C, 59.93; H, 5.83; N, 10.45; Cl, 10.57.

EXAMPLE 19

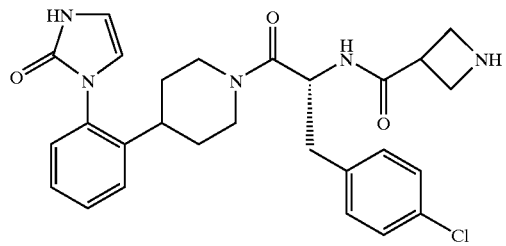

N-((1R)-1-[(4-Chlorophenyl)methyl]-2-oxo-2-{4-[2-(2-oxo(4-imidazolinyl))phenyl]-piperidyl}ethyl) azetidin-3-ylcarboxamide Step (a) tert-Butyl 3-[N-((1R)-1-[(4-chlorophenyl)-methyl]-2-oxo-2-{4-[2-(2-oxo(4-imidazolinyl))-phenyl]piperidyl}ethyl)carbamoyl] azetidinecarboxylate The title compound was prepared according to the procedure described in Example 10 (Step b) using N-((1R)-1-[(4-chlorophenyl)methyl]-2-oxo-2-{4-[2-(2-oxo(4-imidazolinyl))phenyl]-piperidyl)ethyl) (tert-butoxy) carboxamide (Example 18 Step b) (0.227 g, 0.433 mmol) and satd HCl in EtOAc (20 mL), followed by Boc-azetidine-3-carboxylic acid (PepTech Corporation) (0.105 g, 0.52 mmol), EDC (Advanced ChemTech) (0.125 g, 0.65 mmol), HOBT (Novabiochem) (0.058 g, 0.433 mmol) and TEA (Aldrich) (0.058 mL, 0.433 mmol) in $CH_2Cl_2$ (10 mL). Purification by silica gel chromatography (100% EtOAc then 1:9 MeOH:EtOAc) provided the title compound as a white foam (0.2 g). MS (ESL pos. ion) m/z: 608 (M+1). Calc'd for $C_{32}H_{38}ClN_5O_5$: 607.26.

Step (b) N-((1R)-1-[(4-Chlorophenyl)methyl]-2-oxo-2-{4-[2-(2-oxo(4-imidazolinyl))phenyl]-piperidyl}ethyl)azetidin-3-ylcarboxamide The title compound was prepared according to the procedure described in Example 16 (Step b) using tert-butyl 3-[N-((1R)-1-[(4-chlorophenyl)methyl]-2-oxo-2-(4-[2-(2-oxo(4-imidazolinyl))phenyl]piperidyl)ethyl}carbamoyl] azetidinecarboxylate (Step a) (0.2 g, 0.33 mmol) and satd anhydrous HCl in EtOAc (20 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white solid (0.02 g) MS (ESI, pos. ion) m/z: 508 (M+1) Calc'd for $C_{27}H_{30}ClN_5O_3$: 507.20.

EXAMPLE 20

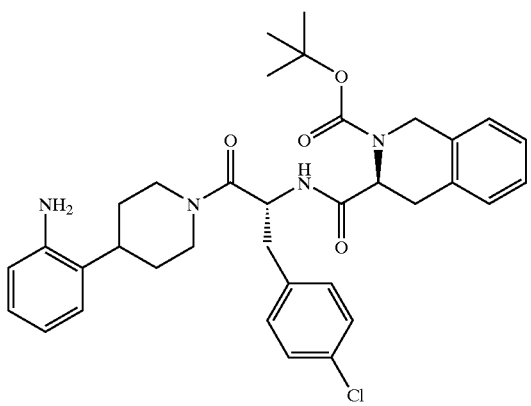

tert-Butyl 3-(N-{(1R)-2-[4-(2-aminophenyl)
piperidyl]-1-[(4-chlorophenyl)methyl]-2-
oxoethyl}carbamoyl)(3S)-1,2,3,4-
tetrahydroisoquinoline-2-carboxylate

Step (a) tert-Butyl 4-(2-[(fluoren-9-ylmethoxy)carbonylamino]phenyl}piperidine-carboxylate To a 250 mL round-bottomed flask equipped with stirring was added Preparation B (5.52 g, 20 mmol) followed by 1,2-dichloroethane (100 mL) and DIEA (Aldrich) (4.4 mL, 22 mmol). The reaction mixture was stirred for 5 min at RT, then treated with 9-fluorenylmethylchloroformate (Aldrich) (5.69 g, 22 mmol). After stirring for 8 h at RT, the reaction was quenched by the addition of satd NH$_4$Cl (60 mL). The organic layer was separated and the aqueous layer extracted with CH$_2$Cl$_2$ (3×50 mL) The organic fractions were combined, washed with satd NaCl, dried over Na$_2$SO$_4$, filtered and concentrated in vacuo. Purification by silica gel chromatography (5:1 hexane:EtOAc) provided the title compound as a pale yellow foam (8.96 g). MS (ESI, pos. ion) m/z: 499 (M+1); MS (ESI, neg. ion) m/z: 497 (M−1). Calc'd for C$_{31}$H$_{34}$N$_2$O$_4$: 498.25.

Step (b) (Fluoren-9-ylmethoxy)-N-(2-(4-piperidyl)phenyl)carboxamide Hydrochloride The title compound was prepared according to the procedure described in Example 16 (Step b) from tert-butyl 4-(2-[(fluoren-9-ylmethoxy)carbonylamino]phenyl) piperidine-carboxylate (Step a) (7.49 g, 15 mmol) and satd anhydrous HCl in EtOAc (50 mL). The title compound was obtained as a white solid (6.51 g). MS (ESI, pos. ion) m/z: 399 (M+1); MS (ESI, neg. ion) m/z: 397 (M−1). Calc'd for C$_{26}$H$_{27}$ClN$_2$O$_2$: 398.20.

Step (c) N-[(1R)-1-[(4-Chlorophenyl)methyl]-2-(4-{2-[(fluoren-9-ylmethoxy)carbonylamino]-phenyl}piperidyl)-2-oxoethyl](tert-butoxy)carboxamide The title compound was prepared according to the procedure described in Example 1 (Step f) from (fluoren-9-ylmethoxy)-N-(2-(4-piperidyl)phenyl)-carboxamide hydrochloride (Step b) (6.51 g, 15 mmol), DIEA (2.7 mL, 15 mmol), Boc-p-Cl-D-PheOH (PepTech Corporation) (6.8 g, 22.5 mmol), HOAT (Aldrich) (3.1 g, 22.5 mmol) and EDC (Aldrich) (4.32 g, 22.5 mmol) in DMF (25 mL). Purification by silica gel chromatography (3:1 hexane:EtOAc) provided the title compound as a white foam (6.87 g). MS (ESI, pos. ion) m/z: 680 (M+1); MS (ESI, neg. ion) m/z: 678 (M−1). Calc'd for C$_{40}$H$_{42}$ClN$_3$O$_5$: 679.28.

Step (d) N-(2-{1-[(2R)-2-Amino-3-(4-chlorophenyl)propanoyl](4-piperidyl)}phenyl)(fluoren-9-ylmethoxy)carboxamide Hydrochloride The title compound was prepared according to the procedure described in Example 16 (Step b) from N-[(1R)-1-[(4-chlorophenyl)methyl]-2-(4-{2-[(fluoren-9-ylmethoxy)carbonylamino]-phenyl}piperidyl)-2-oxoethyl](tert-butoxy)carboxamide (Step c) (6.8 g, 10 mmol) and satd anhydrous HCl in EtOAc (50 mL). The title compound was obtained as a white solid (6.1 g). MS (ESI, pos. ion) m/z: 580 (M+1); MS (ESI, neg. ion) m/z: 578 (M−1). Calc'd for C$_{35}$H$_{35}$Cl$_2$N$_3$O$_3$: 579.23.

Step (e) tert-Butyl 3-{N-[(1R)-1-[(4-chlorophenyl)-methyl]-2-(4-{2-[(fluoren-9-ylmethoxy)carbonylamino]-phenyl}piperidyl)-2-oxoethyl]carbamoyl}(3S)-1,2,3,4-tetrahydroisoquinoline-2-carboxylate The title compound was prepared according to the procedure described in Example 1 (Step f) from N-(2-{1-[(2R)-2-amino-3-(4-chlorophenyl)propanoyl](4-piperidyl)}phenyl)(fluoren-9-ylmethoxy)carboxamide hydrochloride (Step d) (6.1 g, 9.9 mmol), DIEA (2.0 mL, 10 mmol), Roc-L-TicOH (Bachem Company) (4.16 g, 15 mmol), HOAT (Aldrich) (2.04 g, 15 mmol) and EDC (Aldrich) (2.87 g, 15 mmol) in DMF (25 mL). Purification by silica gel chromatography (3:1 hexane:KtOAc) provided the title compound as a white foam (7.09 g). MS (ESI, pos. ion) m/z: 839 (M+1); MS (ESI, neg. ion) m/z: 837 (M−1). Calc'd for C$_{50}$H$_{51}$ClN$_4$O$_6$: 838.35.

Step (f) tert-Butyl 3-(N-{(1R)-2-[4-(2-aminophenyl)-piperidyl]-1-1-[(4-chlorophenyl)methyl]-2-oxoethyl}-carbamoyl)(3S)-1,2,3,4-tetrahydroisoquinoline-2-carboxylate The title compound was prepared according to the procedure described in Example 8 (Step b) using tert-butyl 3-{N-[(1R)-1-[(4-chlorophenyl)methyl]-2-(4-[2-[(fluoren-9-ylmethoxy)carbonylamino]phenyl}piperidyl)-2-oxoethyl]carbamoyl}(3S)-1,2,3,4-tetrahydroisoquinoline-2-carboxylate (Step e) (5.88 g, 7.0 mmol), n-octanethiol (Aldrich) (1.23 g, 8.4 mmol) and 1,8-diazabicyclo[5.4.0]undec-7-ene (Aldrich) (63.8 mg, 0.42 mmol) in THF (50 mL). The title compound was obtained as a yellow solid (3.73 g). MS (ESI, pos. ion) m/z: 617 (M+1); MS (ESI, neg. ion) m/z: 615 (M−1). Calc'd for C$_{35}$H$_{41}$ClN$_4$O$_4$: 618.28.

EXAMPLE 21

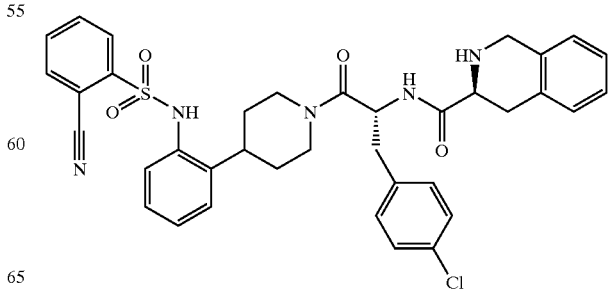

N-{(1R)-1-[(4-Chlorophenyl)methyl]-2-[4-(2-{[(2-cyanophenyl)sulfonyl]amino}-phenyl)piperidyl]-2-oxoethyl}((3S)(3-1,2,3,4-tetrahydroisoquinolyl))carboxamide Step (a) tert-Butyl 3-(N-{(1R)-1-[(4-chlorophenyl)methyl]-2-[4-(2-{[(2-cyanophenyl)sulfonyl]amino}-phenyl)piperidyl]-2-oxoethyl}carbamoyl)(3S)-1,2,3,4-tetrahydroisoquinoline-2-carboxylate To a 50 mL round-bottomed flask equipped with stirring was added tert-butyl 3-(N-{(1R)-2-[4-(2-aminophenyl)piperidyl]-1-[(4-chlorophenyl)methyl]-2-oxoethyl}carbamoyl)(3S)-1,2,3,4-tetrahydroisoquinoline-2-carboxylate (Example 20) (154 mg, 0.25 mmol), 1,2-dichloroethane (10 mL) and pyridine (0.03 mL, 0.3/5 mmol). The reaction mixture was stirred for 5 min at RT, treated with 2-cyanobenzenesulfonyl chloride (Lancaster Synthesis) (50 mg, 0.25 mmol) and stirred at RT for 16 h. The reaction was quenched with satd $NH_4Cl$ (10 mL), the organic layer separated, and the aqueous layer extracted with $CH_2Cl_2$ (2×10 mL). The organic fractions were combined, washed with satd NaCl (10 mL), dried over $Na_2SO_4$, filtered and concentrated in vacuo. Purification by silica gel chromatography (100% EtOAc) provided the title compound as a white foam (167 mg). MS (ESI, pos. ion) m/z: 782 (M+1); MS (ESI, neg. ion) m/z: 780 (M−1). Calc'd for $C_{42}H_{44}ClN_5O_6S$: 781.27.

Step (b) N-{(1R)-1-[(4-Chlorophenyl)methyl]-2-[4-(2-{[(2-cyanophenyl)sulfonyl]amino}-phenyl)piperidyl]-2-oxoethyl}((3S)(3-1,2,3,4-tetrahydroisoquinolyl))-carboxamide The title compound was prepared according to the procedure described in Example 3 (Step b) using tert-butyl 3-(N-{(1R)-1-[(4-chlorophenyl)methyl]-2-[4-(2-{[(2-cyanophenyl}sulfonyl]amino}phenyl)piperidyl]-2-oxoethyl]carbamoyl)(3S)-1,2,3,4-tetrahydroisoquinoline-2-carboxylate (Step a) (167 mg, 0.21 mmol) and 50% TFA in $CH_2Cl_2$ (10 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min] provided the title compound (TFA salt) as a white foam (76 mg). MS (ESI, pos. ion) m/z: 682 (M+1); (ESI, neg. ion) m/z: 680 (M−1). Calc'd for $C_{37}H_{36}ClN_5O_4S$: 681.22.

EXAMPLE 22

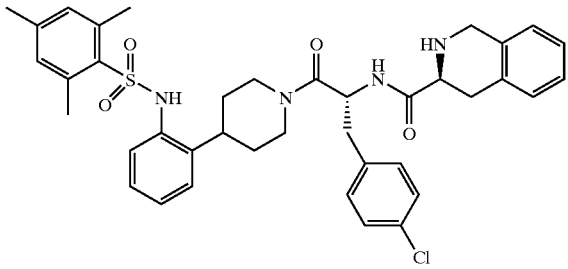

N-{(1R)-1-[(4-Chlorophenyl)methyl]-2-oxo-2-[4-(2-{[(2,4,6-trimethylphenyl)sulfonyl]amino}phenyl)-piperidyl]ethyl}((3S)(3-1,2,3,4-tetrahydroisoquinolyl))-carboxamide Step (a) tert-Butyl 3-(N-{(1R)-1-[(4-chlorophenyl)-methyl]-2-oxo-2-[4-(2-{[(2,4,6-trimethylphenyl)-sulfonyl]-amino}phenyl)piperidyl]-ethyl}carbamoyl)(3S)-1,2,3,4-tetrahydroisoquinoline-2-carboxylate The title compound was prepared according to the procedure described in Example 21 (Step a) by treating tert-butyl 3-(N-{(1R)-2-[4-(2-aminophenyl)piperidyl]-1-[(4-chlorophenyl)methyl]-2-oxoethyl}carbamoyl)(3S)-1,2,3,4-tetrahydroisoquinoline-2-carboxylate (Example 20) (154 mg, 0.25 mmol) with 2-mesitylenesulfonyl chloride (Aldrich) (55 mg, 0.25 mmol) and pyridine (0.03 mL, 0.375 mmol) in 1,2-dichloroethane (10 mL). Purification by silica gel chromatography (100% EtOAc) provided the title compound as a white foam (146 mg). MS (ESI, pos. ion) m/z: 799 (M+1); MS (ESI, neg. ion) m/z: 797 (M−1) Calc'd for $C_{44}H_{51}ClN_4O_6S$: 798.32.

Step (b) N-{(1R)-1-[(4-Chlorophenyl)methyl]-2-oxo-2-[4-(2-{[(2,4,6-trimethylphenyl)sulfonyl]amino}-phenyl)piperidyl]ethyl}((3S)(3-1,2,3,4-tetrahydroisoquinolyl))carboxamide The title compound was prepared according to the procedure described in Example 3 (Step b) using tert-butyl 3-(N-((1R)-1-[(4-chlorophenyl)methyl]-2-oxo-2-[4-(2-{[(2,4,6-trimethylphenyl)sulfonyl]amino}phenyl) piperidyl] ethyl)carbamoyl)(3S)-1,2,3,4-tetrahydroisoquinoline-2-carboxylate (Step a) (146 mg, 0.18 mmol) and 50% TFA in $CH_2Cl_2$ (10 mL). Purification by reverse phase preparative HPLC [Phenomenex; 5 μm 250×21.2 mm, 5% to 95% $CH_3CN$ (0.1% TFA) in $H_2O$ (0.1% TFA) over 30 min, then 100% $CH_3CN$ (0.1% TFA) for 2 min) provided the title compound (TFA salt) as a white foam (81 mg). MS (ESI, pos. ion) m/z: 699 (M+1); (ESI, neg. ion) m/z: 697 (M−1). Calc'd for $C_{30}H_{43}ClN_4O_4S$: 698.27.

EXAMPLE 23

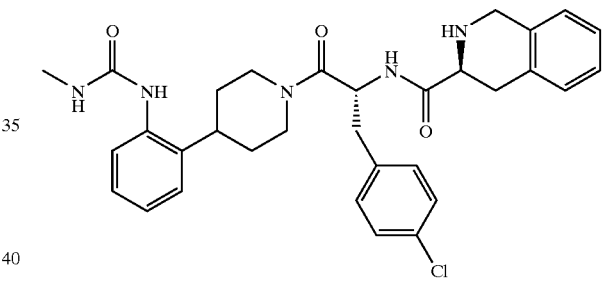

N-[(1R)-1-[(4-Chlorophenyl)methyl]-2-(4-{2-[(methylamino)carbonylamino]-phenyl}piperidyl)-2-oxoethyl]((3S)(3-1,2,3,4-tetrahydroisoquinolyl))-carboxamide Step (a) tert-Butyl 3-{N-[(1R)-1-[(4-chlorophenyl)methyl]-2-(4-{2-[(methylamino)carbonylamino]phenyl}piperidyl)-2-oxoethyl]carbamoyl}(3S)-1,2,3,4-tetrahydroisoquinoline-2-carboxylate To a 50 mL round-bottomed flask equipped with stirring was added tert-butyl 3-(N-{(1R)-2-[4-(2-aminophenyl)piperidyl]-1-[(4-chlorophenyl)methyl]-2-oxoethyl}carbamoyl)(3S)-1,2,3,4-tetrahydroisoquinoline-2-carboxylate (Example 20) (462 mg, 0.75 mmol) followed by $CH_3CN$ (15 mL) and ethylisocyanate (Chemservice, Inc.) (45.6 mg. 0.80 mmol). The reaction mixture was stirred at RT for 16 h, then the solvent was removed in vacuo. The resulting yellow oil was dissolved in EtOAc (20 mL) and washed with satd $NaHCO_3$ (20 mL) and satd NaCl (20 mL). The organic layer was dried over $Na_2SO_4$, filtered and concentrated in vacuo. Purification by silica gel chromatography (100% EtOAc) provided the title compound as a white foam (397 mg). MS (ESI, pos. ion) m/z: 674 (M+1); MS (ESI, neg. ion) m/z: 672 (M−1). Calc'd for $C_{37}H_{44}ClN_5O_0$: 673.30.

Step (b) N-[(1R)-1-[(4-Chlorophenyl)methyl]-2-(4-{2-[(methylamino)carbonylamino]-phenyl}piperidyl)-2-oxoethyl]((3S)(3-1,2,3,4-tetrahydroisoquinolyl))-carboxamide The title compound was prepared according to the procedure described in Example 3 (Step b) using tert-butyl 3-{N-[(1R)-1[(4-chlorophenyl)methyl]-2-(4-{2-[(methylamino)carbonylamino]phenyl}piperidyl)-2-oxoethyl]carbamoyl}(3S)-1,2,3,4-tetrahydroisoquinoline-2-carboxylate (Step a) (397 mg, 0.59 mmol) and 50% TFA in CH$_2$Cl$_2$ (20 mL). Purification by reverse phase preparative HPLC [Phenomenex; 5 μm 250×21.2 mm, 5% to 95% CH$_3$CN (0.1% TFA) in H$_2$O (0.1% TFA) over 30 min, then 100% CH$_3$CN (0.1% TFA) for 2 min] provided the title compound (TFA salt) as a white foam (266 mg). MS (ESI, pos. ion) m/z: 574 (M+1); (ESI, neg. ion) in/z: 572 (M−1). Calc'd for C$_{32}$H$_{36}$ClN$_5$O$_3$: 573.25. Anal. Calcd for C$_{32}$H$_{36}$ClN$_5$O$_3$.1.8C$_2$HF$_3$O$_2$: C, 54.86; H. 4.89; N, 8.99. Found: C, 55.11; H, 5.04; N, 9.11.

EXAMPLE 24

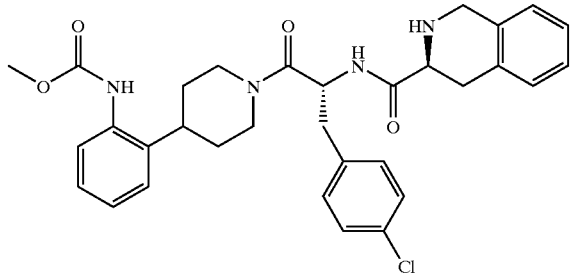

N-((1R)-1-[(4-Chlorophenyl)methyl]-2-{4-[2-(methoxycarbonylamino)phenyl]piperidyl}-2-oxoethyl)((3S)(3-1,2,3,4-tetrahydroisoquinolyl))-carboxamide Step (a) tert-Butyl 3-[N-((1R)-1-[(4-chlorophenyl)-methyl]-2-{4-[2-(methoxycarbonylamino)-phenyl]-piperidyl}-2-oxoethyl)carbamoyl](3S)-1,2,3,4-tetrahydroisoquinoline-2-carboxylate To a 50 mL round-bottomed flask equipped with stirring was added tert-butyl 3-(N-{(1R)-2-[4-(2-aminophenyl) piperidyl]-1-[(4-chlorophenyl)methyl]-2-oxoethyl}carbamoyl)(3S)-1,2,3,4-tetrahydroisoquinoline-2-carboxylate (Example 20) (462 mg, 0.75 mmol) and CH$_2$Cl$_2$ (15 mL) followed by DIEA (0.16 mL, 0.9 mmol). The reaction mixture was stirred for 5 min at RT then treated with methyl chloroformate (Aldrich) (84.6 mg, 0.9 mmol) at 0° C. The reaction mixture was stirred at RT for 12 h then quenched with satd NaHCO$_3$ (15 mL). The organic layer was separated and the aqueous layer was extracted with CH$_2$Cl$_2$ (2×15 mL). The organic fractions were combined, washed with satd NaCl (15 mL), dried over Na$_2$SO$_4$, filtered and concentrated in vacuo. Purification by silica gel chromatography (100% EtOAc) provided the title compound as a white foam (412 mg). MS (ESI, pos. ion) m/z: 675 (M+1); MS (ESI, neg. ion) m/z: 673 (M−1). Calc'd for C$_{11}$H$_{13}$ClN$_4$O$_6$: 674.29.

Step (b) N-((1R)-1-[(4-Chlorophenyl)methyl]-2-{4-[2-(methoxycarbonylamino)phenyl]piperidyl}-2-oxoethyl)-((3S)(3-1,2,3,4-tetrahydroisoquinolyl)) carboxamide trifluoroacetate The title compound was prepared according to the procedure described in Example 3 (Step b) using tert-butyl 3-[N-((1R)-1-[(4-chlorophenyl)methyl]-2-(4-[2-(methoxycarbonylamino)-phenyl]-piperidyl}-2-oxoethyl)-carbamoyl](3S)-1,2,3,4-tetrahydroisoquinoline-2-carboxylate (Step a) (412 mg, 0.61 mmol) and 50% TFA in CH$_2$Cl$_2$ (20 mL). Purification by reverse phase preparative HPLC [Phenomenex; 5 μm 250×21.2 mm, 5% to 95% CH$_3$CN (0.1% TFA) in H$_2$O (0.1% TFA) over 30 min, then 100% CH$_3$CN (0.1% TFA) for 2 min] provided the title compound as a white foam (159 mg). MS (ESI, pos. ion) m/z: 575 (M+1); (ESI, neg. ion) m/z: 573 (M−1). Calc'd for C$_{32}$H$_{35}$ClN$_4$O$_4$: 574.23. Anal. Calcd for C$_{32}$H$_{35}$ClN$_4$O$_4$.18C$_2$HF$_3$O$_2$: C, 57.45; H, 5.06; N, 7.75. Found: C, 57.66; H, 5.09; N, 7.62.

EXAMPLE 25

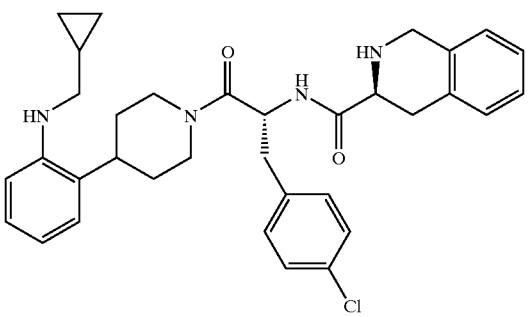

N-[(1R)-1-[(4-Chlorophenyl)methyl]-2-(4-{2-[(cyclopropylmethyl)amino]-phenyl}piperidyl)-2-oxoethyl]((3S)(3-1,2,3,4-tetrahydroisoquinolyl)) carboxamide Step (a) tert-Butyl 3-{N-[(1R)-1-[(4-chlorophenyl) methyl]-2-(4-{2-[(cyclopropylmethyl)-amino] phenyl}piperidyl)-2-oxoethyl]carbamoyl}(3S)-1,2,3,4-tetrahydroisoquinoline-2-carboxylate To a 50 round-bottomed flask equipped with stirring was added tert-butyl 3-(N-{(1R)-2-[4-(2-aminophenyl) piperidyl]-1-[(4-chlorophenyl)methyl]-2-oxoethyl} carbamoyl)(3S)-1,2,3,4-tetrahydroisoquinoline-2-carboxylate (Example 20) (462 mg, 0.75 mmol) followed by 1,2-dichloroethane (20 mL) and cyclopropyl-carboxaldehyde (Aldrich) (58 mg, 0.83 mmol). The reaction mixture was stirred for 6 h, then treated with sodium triacetoxyborohydride (Aldrich) (176 mg, 0.83 mmol) at 0° C. After stirring for 12 h at RT, the reaction mixture was quenched with satd NaHCO$_3$ (20 mL). The organic layer was separated and the aqueous layer extracted with CH$_2$Cl$_2$ (2×20 mL). The organic fractions were combined, washed with satd NaCl (50 mL), dried over Na$_2$SO$_4$, filtered and concentrated in vacuo. Purification by silica gel chromatography (1:10 MeOH:EtOAc) provided the title compound as a white foam (431 mg). MS (ESI, pos. ion) m/z: 671 (M+1); MS (ESI, neg. ion) m/z: 669 (M−1). Calcd for C$_{39}$H$_{47}$ClN$_4$O$_4$: 670.33.

Step (b) N-[(1R)-1-[(4-Chlorophenyl)methyl]-2-(4-{2-[(cyclopropylmethyl)amino]-phenyl}piperidyl)-2-oxoethyl]((3S)(3-1,2,3,4-tetrahydroisoquinolyl))-carboxamide The title compound was prepared according to the procedure described in Example 3 (Step b) using tert-butyl 3-{N-[(1R)-1-[(4-chlorophenyl)methyl]-2-(4-(2-[(cyclopropylmethyl)-amino]phenyl}piperidyl)-2-oxoethyl]

carbamoyl}(3S)-1,2,3,4-tetrahydroisoquinoline-2-carboxylate (Step a) (431 mg, 0.64 mmol) and 50% TFA in CH$_2$Cl$_2$ (20 mL). Purification by reverse phase preparative HPLC [Phenomenex; 5 μm 250×21.2 mm, 5% to 95% CH$_3$CN (0.1% TFA) in H$_2$O (0.1% TFA) over 30 min, then 100% CH$_3$CN (0.1% TFA) for 2 min] provided the title compound (TFA salt) as a white foam (207 mg). MS (ESI, pos. ion) m/z: 571 (M+1); (ESI, neg. ion) m/z: 569 (M−1). Calc'd for C$_{34}$H$_{39}$ClN$_4$O$_2$: 570.28. Anal. Calcd for C$_{34}$H$_{39}$ClN$_4$O$_2$-2.4C$_2$HF$_3$O$_2$: C, 55.16; H, 4.94; N, 6.63. Found: C, 55.18; H, 5.13; N, 6.61.

EXAMPLE 26

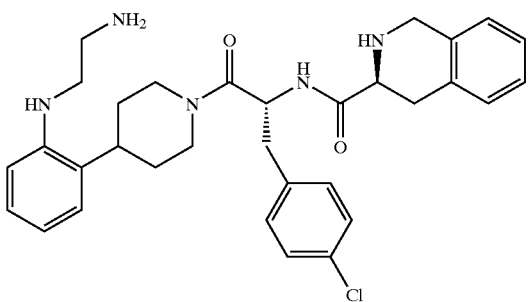

N-[(1R)-2-(4-{2-[(2-Aminoethyl)amino]phenyl}piperidyl)-1-[(4-chlorophenyl)methyl]-2-oxoethyl]((3S)(3-1,2,3,4-tetrahydroisoquinolyl))carboxamide Step (a) tert-Butyl 3-[N-((1R)-2-{4-[2-({2-[(tert-butoxy)carbonylamino]ethyl}-amino)phenyl]-piperidyl}-1-[(4-chlorophenyl)methyl]-2-oxoethyl)carbamoyl](3s)-1,2,3,4-tetrahydroisoquinoline-2-carboxylate The title compound was prepared according to the procedure described in Example 25 (Step a) using tert-butyl 3-(N-{(1R)-2-[4-(2-aminophenyl)piperidyl]-1-[(4-chlorophenyl)methyl]-2-oxoethyl}carbamoyl)(3S)-1,2,3,4-tetrahydroisoquinoline-2-carboxylate (Example 20) (462 mg, 0.75 mmol), tert-butyl N-(2-oxoethyl)carbamate (Aldrich) (131 mg, 0.83 mmol) and NaBH(OAc)$_3$ (Aldrich) (176 mg, 0.83 mmol) in CH$_2$Cl$_2$ (20 mL). Purification by silica gel chromatography (1:10 McOH:EtOAc) provided the title compound as a white foam (386 mg). MS (ESI, pos. ion) m/z: 760 (M+1); (ESI, neg. ion) m/z: 758 (M−1). Calc'd for C$_{42}$H$_{54}$ClN$_5$O$_6$: 759.38.

Step (b) N-[(1R)-2-(4-{2-[(2-Aminoethyl)amino]phenyl}piperidyl)-1-[(4-chlorophenyl)methyl]-2-oxoethyl] ((3S)(3-1,2,3,4-tetrahydroisoquinolyl))carboxamide The title compound was prepared according to the procedure described in Example 3 (Step b) using tert-butyl 3-[N-((1R)-2-{4-[2-({2-[(tert-butoxy)carbonyl-amino]ethyl}-amino)phenyl]-piperidyl}-1-[(4-chlorophenyl)methyl]-2-oxoethyl)carbamoyl](3S)-1,2,3,4-tetrahydroisoquinoline-2-carboxylate (Step a) (386 mg, 0.5 mmol) and 50% TFA in CH$_2$Cl$_2$ (20 mL). Purification by reverse phase preparative HPLC [Phenomenex; 5 μm 250× 21.2 mm, 5% to 95% CH$_3$CN (0.1% TFA) in H$_2$O (0.1% TFA) over 30 min, then 100% CH$_3$CN (0.1% TFA) for 2 min] provided the title compound (TFA salt) as a white foam (162 mg). MS (ESI, pos. ion) m/z: 560 (M+1); (ESI, neg. ion) m/z: 558 (M−1). Calc'd for C$_{32}$H$_{38}$ClN$_5$O$_2$: 559.27. Anal. Calcd for C$_{32}$H$_{38}$ClN$_5$O$_2$-3C$_2$HF$_3$O$_2$: C, 50.59; H, 4.58; N, 7.76. Found: C, 50.98; H, 4.87; N, 8.01.

Other compounds included in this invention are set forth in Tables 1-8 below.

TABLE 1

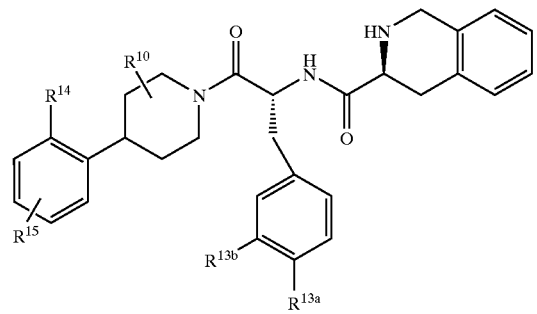

| # | R$^{14}$ | R$^{15}$ | R$^{10}$ | R$^{13a}$ | R$^{13b}$ |
|---|---|---|---|---|---|
| 27. | methylsulfonylamino | H | H | Cl | H |
| 28. | N-propyl-N-(CypCH$_2$)aminomethyl | H | H | Cl | H |
| 29. | N-propyl-N-(CypCH$_2$)aminomethyl | H | H | Br | H |
| 30. | N,N-di(CypCH$_2$)aminomethyl | H | H | Cl | H |
| 31. | N-(methylsulfonyl)-N-(aminoethyl)amino | H | H | Cl | Cl |
| 32. | methylsulfonylamino | H | 3-cypCH$_2$NHC=OCH$_2$— | Cl | H |
| 33. | 2-pyridylcarbonylamino | H | H | Cl | H |
| 34. | benzylaminocarbonyl | H | H | Cl | H |

TABLE 1-continued

| # | R14 | R15 | R10 | R13a | R13b |
|---|---|---|---|---|---|
| 35. | (2,2-dioxo-isothiazolidin-N-yl, N-methyl) | H | H | Cl | H |
| 36. | N-methyl-N-methylcarbonylamino | H | H | Cl | H |
| 37. | N-propyl-N-methylsulfonylamino | H | H | Cl | H |
| 38. | methylsulfonylamino | H | 3-NH$_2$—(CH$_2$)$_2$NHC=OCH$_2$— | Cl | H |
| 39. | N-(CypCH$_2$)-N-(MeSO$_2$)aminomethyl | H | H | Cl | H |
| 40. | N-(CypCH$_2$)-N-propylaminomethyl | F | H | Cl | H |
| 41. | N-(phenylpropyl)-N-(MeSO$_2$)amino | H | H | Cl | H |
| 42. | methylsulfonylamino | 4-CF$_3$ | H | Cl | H |
| 43. | methylcarbonyl | H | H | Cl | H |
| 44. | N-pyrrolidinylcarbonyl | H | H | Cl | H |
| 45. | CH$_3$C=ONH | H | H | Cl | H |
| 46. | methylsulfonylamino | H | 3-phenyl(CH$_2$)$_2$NHC=OCH$_2$— | Cl | H |
| 47. | methoxy | H | H | Cl | H |
| 48. | amino | H | H | Cl | H |
| 49. | N-(3-pyridylcarbonyl)-N-(aminoethyl)amino | H | H | Cl | H |
| 50. | N-(isopropylcarbonyl)-N-(aminoethyl)amino | H | H | Cl | H |
| 51. | N-(pentylcarbonyl)-N-(aminoethyl)amino | H | H | Cl | H |
| 52. | N-(ethylcarbonyl)-N-(aminoethyl)amino | H | H | Cl | H |
| 53. | N-(t-butylcarbonyl)-N-(aminoethyl)amino | H | H | Cl | H |
| 54. | N-(butylcarbonyl)-N-(aminoethyl)amino | H | H | Cl | H |
| 55. | N-(isobutylcarbonyl)-N-(aminoethyl)amino | H | H | Cl | H |
| 56. | N-(propylcarbonyl)-N-(aminoethyl)amino | H | H | Cl | H |
| 57. | N-(phenylcarbonyl)-N-(aminoethyl)amino | H | H | Cl | H |
| 58. | N-(3-methoxyphenylcarbonyl)-N-(aminoethyl)amino | H | H | Cl | H |
| 59. | N-(benzylcarbonyl)-N-(aminoethyl)amino | H | H | Cl | H |
| 60. | N-(cyclohexylcarbonyl)-N-(aminoethyl)amino | H | H | Cl | H |
| 61. | N-(cyclopentylcarbonyl)-N-(aminoethyl)amino | H | H | Cl | H |
| 62. | N-(cyclopropylcarbonyl)-N-(aminoethyl)amino | H | H | Cl | H |
| 63. | N-(cyclobutylcarbonyl)-N-(aminoethyl)amino | H | H | Cl | H |
| 64. | N-(2-thienylmethylcarbonyl)-N-(aminoethyl)amino | H | H | Cl | H |
| 65. | N-(methoxymethylcarbonyl)-N-(aminoethyl)amino | H | H | Cl | H |
| 66. | N-(methoxymethylcarbonyl)-N-(CypCH$_2$)amino | H | H | Cl | H |
| 67. | N-(methylthiopropyl)-N-(CypCH$_2$)amino | H | H | Cl | H |
| 68. | N-(methylcarbonyl)-N-(CypCH$_2$)amino | H | H | Cl | H |
| 69. | N-(isopropylcarbonyl)-N-(CypCH$_2$)amino | H | H | Cl | H |
| 70. | N-(isobutylcarbonyl)-N-(CypCH$_2$)amino | H | H | Cl | H |
| 71. | N-(ethylcarbonyl)-N-(CypCH$_2$)amino | H | H | Cl | H |
| 72. | N-(3-methoxyphenylcarbonyl)-N-(CypCH$_2$)amino | H | H | Cl | H |
| 73. | N-(benzylcarbonyl)-N-(CypCH$_2$)amino | H | H | Cl | H |
| 74. | N-(phenylethyl)-N-(CypCH$_2$)amino | H | H | Cl | H |
| 75. | N-(2-imidazolyl)-N-(CypCH$_2$)amino | H | H | Cl | H |
| 76. | N-(4-methyl-5-imidazolyl)-N-(CypCH$_2$)amino | H | H | Cl | H |
| 77. | N-(4-imidazolylmethyl)-N-(CypCH$_2$)amino | H | H | Cl | H |
| 78. | N-(2-thienylmethyl)-N-(CypCH$_2$)amino | H | H | Cl | H |
| 79. | N-(2-thienylmethylcarbonyl)-N-(CypCH$_2$)amino | H | H | Cl | H |
| 80. | N-(3-furylmethyl)-N-(CypCH$_2$)amino | H | H | Cl | H |
| 81. | N-(phenylcarbonyl)-N-(CypCH$_2$)amino | H | H | Cl | H |
| 82. | N-(cyclopentylcarbonyl)-N-(CypCH$_2$)amino | H | H | Cl | H |
| 83. | N-(cyclohexylcarbonyl)-N-(CypCH$_2$)amino | H | H | Cl | H |
| 84. | N-(cyclopropylcarbonyl)-N-(CypCH$_2$)amino | H | H | Cl | H |
| 85. | N-(propyl)-N-(aminoethyl)amino | H | H | Cl | H |
| 86. | N-(CypCH$_2$)-N-(aminoethyl)amino | H | H | Cl | H |
| 87. | N-(ethyl)-N-(aminoethyl)amino | H | H | Cl | H |
| 88. | N-(hexyl)-N-(aminoethyl)amino | H | H | Cl | H |
| 89. | N-(heptyl)-N-(aminoethyl)amino | H | H | Cl | H |
| 90. | N-(butyl)-N-(aminoethyl)amino | H | H | Cl | H |

TABLE 1-continued

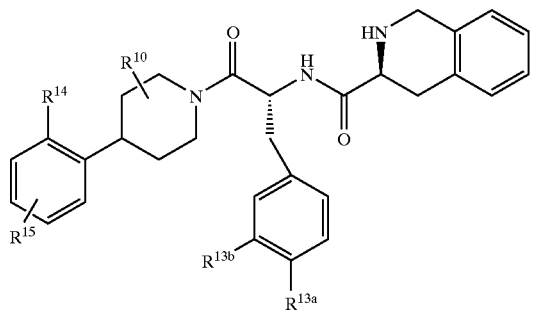

| # | $R^{14}$ | $R^{15}$ | $R^{10}$ | $R^{13a}$ | $R^{13b}$ |
|---|---|---|---|---|---|
| 91. | N-(3-ethylbutyl)-N-(aminoethyl)amino | H | H | Cl | H |
| 92. | N-(2-ethylbutyl)-N-(aminoethyl)amino | H | H | Cl | H |
| 93. | N-(phenylethyl)-N-(aminoethyl)amino | H | H | Cl | H |
| 94. | N-(methylsulfonyl)-N-(N',N'-diethylaminoethyl)amino | H | H | Cl | H |
| 95. | N-(methylsulfonyl)-N-(N',N'-dipropylaminoethyl)amino | H | H | Cl | H |
| 96. | N-(methylsulfonyl)-N-(N',N'-dimethylaminoethyl)amino | H | H | Cl | H |
| 97. | N-(methylsulfonyl)-N-(N',N'-di(CypCH$_2$)aminoethyl)amino | H | H | Cl | H |
| 98. | N-methyl-N-(hydroxyethyl)aminomethyl | H | H | Cl | H |
| 99. | N-(pentyl)-N-(aminoethyl)amino | H | H | Cl | H |
| 100. | N,N-di(CypCH$_2$)amino | H | H | Cl | H |
| 101. | 2-oxo-benzimidazol-1-yl | H | H | Cl | H |
| 102. | N-(2-thienylmethylcarbonyl)-N-(CypCH$_2$)amino | H | H | Cl | H |
| 103. | N-(benzylaminocarbonyl)-N-(CypCH$_2$)amino | H | H | Cl | H |
| 104. | N-(benzylaminocarbonyl)-N-(aminoethyl)amino | H | H | Cl | H |
| 105. | N-(isobutyl)-N-(aminoethyl)amino | H | H | Cl | H |

TABLE 2

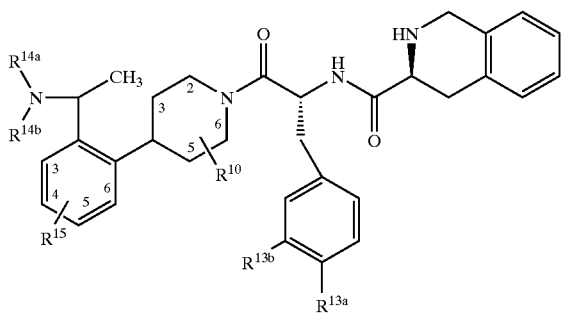

| # | $R^{14a}$ | $R^{14b}$ | $R^{15}$ | $R^{10}$ | $R^{13a}$ | $R^{13b}$ |
|---|---|---|---|---|---|---|
| 106. | cyclopropylmethyl | methyl | H | H | Cl | H |
| 107. | cyclopropylmethyl | H | H | H | Cl | H |
| 108. | methylcarbonyl | methyl | H | H | Cl | H |
| 109. | isobutyl | methyl | H | H | Cl | H |
| 110. | propyl | methyl | H | H | Cl | H |
| 111. | methylsulfonyl | methyl | H | H | Cl | H |
| 112. | ethyl | methyl | H | H | Cl | H |
| 113. | ethoxycarbonylcyclopropylmethyl | methyl | H | H | Cl | H |
| 114. | isopentyl | methyl | H | H | Cl | H |
| 115. | 4-methylcarbonylaminobenzyl | methyl | H | H | Cl | H |
| 116. | methyl | H | 4-Br | H | Cl | H |
| 117. | methyl | methyl | H | H | Cl | H |
| 118. | 3-thienylmethyl | methyl | H | H | Cl | H |
| 119. | benzyloxyethyl | methyl | H | H | Cl | H |
| 120. | 2-methoxybenzyl | methyl | H | H | Cl | H |
| 121. | methyl | H | H | H | Cl | H |
| 122. | 4-pyridylmethyl | methyl | H | H | Cl | H |
| 123. | 2-pyrrolidinylmethyl | methyl | H | H | Cl | H |
| 124. | 3-methoxybenzyl | methyl | H | H | Cl | H |
| 125. | benzyl | methyl | H | H | Cl | H |
| 126. | aminoethyl | methyl | H | H | Cl | H |
| 127. | 4-methoxybenzyl | methyl | H | H | Cl | H |
| 128. | cyclohexylmethyl | methyl | H | H | Cl | H |

TABLE 2-continued

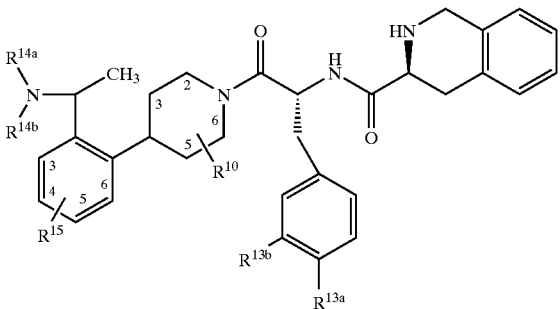

| # | $R^{14a}$ | $R^{14b}$ | $R^{15}$ | $R^{10}$ | $R^{13a}$ | $R^{13b}$ |
|---|---|---|---|---|---|---|
| 129. | 2-aminopropyl | methyl | H | H | Cl | H |
| 130. | methylamino | methyl | H | H | Cl | H |
| 131. | 3-cyanobenzyl | methyl | H | H | Cl | H |
| 132. | isopropyl | methyl | H | H | Cl | H |
| 133. | CypCH2— | methylcarbonyl | H | H | Cl | H |
| 134. | methylcarbonyl | methyl | H | H | Cl | H |

TABLE 3

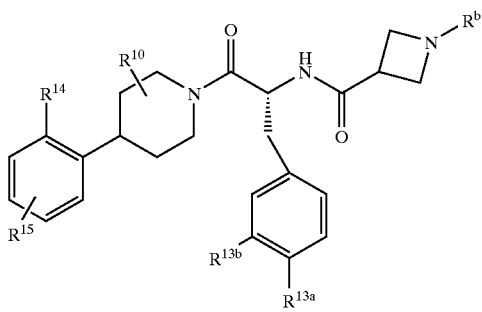

| # | $R^{14}$ | $R^{10}$ | $R^{15}$ | $R^{13a}$ | $R^{13b}$ | $R^b$ |
|---|---|---|---|---|---|---|
| 135. | N—(CH$_3$SO$_2$)—N—(CypCH$_2$)amino | H | H | Cl | H | isobutyl |
| 136. | N—(CH$_3$SO$_2$)—N—(CypCH$_2$)amino | H | H | Cl | H | —CH$_2$C(CH$_3$)$_3$ |
| 137. | N—(CH$_3$SO$_2$)—N—(CypCH$_2$)amino | H | H | Cl | H | —CH$_2$cyp |
| 138. | N—(CH$_3$SO$_2$)—N—(CypCH$_2$)amino | H | H | Cl | H | butyl |
| 139. | N—(CH$_3$SO$_2$)—N—(CypCH$_2$)amino | H | H | Cl | H | pentyl |
| 140. | N—(CH$_3$SO$_2$)—N—(CypCH$_2$)amino | H | H | Cl | H | —CH$_2$chxl |
| 141. | N—(CH$_3$SO$_2$)—N—(CypCH$_2$)amino | H | H | Cl | H | ethyl |
| 142. | N—(CH$_3$SO$_2$)—N—(CypCH$_2$)amino | H | H | Cl | H | methyl |
| 143. | N—(CH$_3$SO$_2$)—N—(CypCH$_2$)amino | H | H | Cl | H | isopropyl |
| 144. | N—(CH$_3$SO$_2$)—N—(CypCH$_2$)amino | H | H | Cl | H | benzyl |
| 145. | N—(CH$_3$SO$_2$)amino | H | H | Cl | H | H |
| 146. | N—(CH$_3$SO$_2$)—N—(CypCH$_2$)amino— | H | H | Cl | H | propyl |
| 147. | 1,2,3-triazol-2-ylmethyl | H | H | Cl | H | H |
| 148. | N—(CypCH$_2$)—N—propylaminoCH$_2$— | H | H | Cl | H | Boc |
| 149. | N—(CypCH$_2$)—N—propylaminoCH$_2$— | H | H | Cl | H | H |
| 150. | 1-imidazolylmethyl | H | H | Cl | H | H |
| 151. | 1-tetrazolylmethyl | H | H | Cl | H | H |
| 152. | 2,5-dimethylpyrrolidin-1-yl | H | H | Cl | H | H |
| 153. | 2-oxo-pyrrolidin-1-ylmethyl | H | H | Cl | H | H |
| 154. | 2-oxo-pyrrolidin-5-ylmethyl | H | H | Cl | H | isopropyl |
| 155. | 2-oxo-pyrrolidin-1-ylmethyl | H | H | Cl | H | ethyl |
| 156. | 2-oxo-pyrrolidin-1-ylmethyl | H | H | Cl | H | CypCH$_2$— |
| 157. | 2-oxo-pyrrolidin-1-ylmethyl | H | H | Cl | H | —CH$_2$C(CH$_3$)$_3$ |
| 158. | 8-aza-bicyclo[3.2.1]oct-8-ylmethyl | H | H | Cl | H | H |
| 159. | 8-aza-bicyclo[3.2.1]oct-8-ylmethyl | H | H | Cl | H | isopropyl |
| 160. | 8-aza-bicyclo[3.2.1]oct-8-ylmethyl | H | H | Cl | H | ethyl |
| 161. | 8-aza-bicyclo[3.2.1]oct-8-ylmethyl | H | H | Cl | H | CypCH$_2$— |
| 162. | 8-aza-bicyclo[3.2.1]oct-8-ylmethyl | H | H | Cl | H | —CH$_2$C(CH$_3$)$_3$ |
| 163. | phenoxymethyl | H | H | Cl | H | H |
| 164. | 1-methylpiperazin-4-ylmethyl | H | H | Cl | H | H |
| 165. | 2,6-dimethylpiperdin-1-ylmethyl | H | H | Cl | H | H |
| 166. | 3-pyridyloxymethyl | H | H | Cl | H | H |

TABLE 3-continued

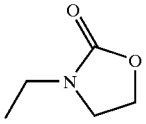

| # | R14 | R10 | R15 | R13a | R13b | Rb |
|---|---|---|---|---|---|---|
| 167. | 1,2,3-triazol-2-ylmethyl | H | H | Cl | H | isopropyl |
| 168. | 1,2,3-triazol-2-ylmethyl | H | H | Cl | H | H |
| 169. | 1,2,3-triazol-2-ylmethyl | H | H | Cl | H | CypCH2— |
| 170. | 1,2,4-triazol-1-ylmethyl | H | H | Cl | H | H |
| 171. | 2-oxopyridylmethyl | H | H | Cl | H | H |
| 172. | 1,2,3-triazol-2-ylmethyl | H | H | Cl | H | isobutyl |
| 173. | 4-morpholinomethyl | H | H | Cl | H | H |
| 174. | 2-CH3-imidazol-1-ylmethyl | H | H | Cl | H | H |
| 175. | 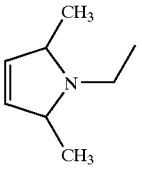 | H | H | Cl | H | H |
| 176. | 2-propylimidazol-1-ylmethyl | H | H | Cl | H | H |
| 177. | 1-piperidylmethyl | H | H | Cl | H | H |
| 178. | 1-pyrrolidinylmethyl | H | H | Cl | H | H |
| 179. | N—(MeSO2)—N—(CypCH2)aminomethyl | H | H | Cl | H | H |
| 180. | 2-isopropylimidazol-1-ylmethyl | H | H | Cl | H | H |
| 181. | 1,2,3-triazol-2-ylmethyl | H | H | Cl | H | —CH2C(CH3)3 |
| 182. | 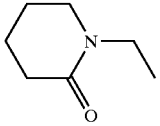 | H | H | Cl | H | H |
| 183. | | H | H | Cl | H | H |
| 184. | 1,2,3-triazol-2-ylmethyl | H | H | Cl | H | chxl |
| 185. | N—(MeSO2)—N—(CypCH2)aminomethyl | H | H | Cl | H | cycloheptyl |
| 186. | N—(MeSO2)—N—(CypCH2)aminomethyl | H | H | Cl | H | morpholino |
| 187. | N—(MeSO2)—N—(CypCH2)aminomethyl | H | H | Cl | H | 2-(ethyl)butyl |
| 188. | N—(MeSO2)—N—(CypCH2)aminomethyl | H | H | Cl | H | chxl |
| 189. | 1-pyrazolylmethyl | H | H | Cl | H | CypCH2— |
| 190. | 1-pyrazolylmethyl | H | H | Cl | H | ethyl |
| 191. | 1-pyrazolylmethyl | H | H | Cl | H | H |
| 192. | 1-pyrazolylmethyl | H | H | Cl | H | isopropyl |
| 193. | 1,2,3-triazo1-1-ylmethyl | H | H | Cl | H | isopropyl |
| 194. | N-propyl-N—(CypCH2)aminomethyl | H | H | Cl | H | isobutyl |
| 195. | N-propyl-N—(CypCH2)aminomethyl | H | H | Cl | H | ethyl |
| 196. | N—(CypCH2)—N-propylaminomethyl | H | H | Cl | H | —CH2C(CH3)3 |
| 197. | 1,2,3-triazol-1-ylmethyl | H | H | Cl | H | isobutyl |
| 198. | N—(CH3SO2)—N—(CypCH2)amino | H | H | Br | H | isobutyl |
| 199. | N—(CH3SO2)—N—(CypCH2)amino | H | H | Br | H | —CH2C(CH3)3 |
| 200. | N—(CH3SO2)—N—(CypCH2)amino | H | H | Br | H | —CH2cyp |
| 201. | N—(CH3SO2)—N—(CypCH2)amino | H | H | Br | H | butyl |
| 202. | N—(CH3SO2)—N—(CypCH2)amino | H | H | Br | H | pentyl |
| 203. | N—(CH3SO2)—N—(CypCH2)amino | H | H | Br | H | —CH2chxl |
| 204. | N—(CH3SO2)—N—(CypCH2)amino | H | H | Br | H | ethyl |
| 205. | N—(CH3SO2)—N—(CypCH2)amino | H | H | Br | H | methyl |
| 206. | N—(CH3SO2)—N—(CypCH2)amino | H | H | Br | H | isopropyl |

TABLE 3-continued

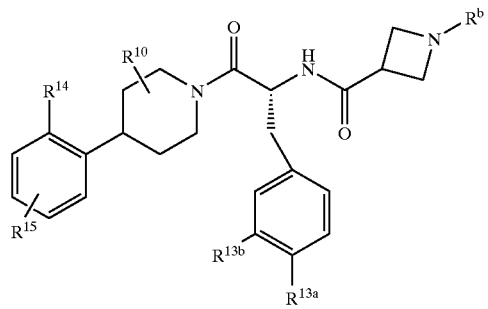

| # | R14 | R10 | R15 | R13a | R13b | Rb |
|---|---|---|---|---|---|---|
| 207. | N—(CH₃SO₂)—N—(CypCH₂)amino | H | H | Br | H | H |
| 208. | N—(CypCH₂)—N—(MeSO₂)amino | H | H | Cl | H | cyclopentyl |
| 209. | N—(CypCH₂)—N—(MeSO₂)amino— | H | H | Cl | H | 2-butyl |
| 210. | 1,2,3-triazol-1-ylmethyl | H | H | Cl | H | ethyl |
| 211. | 1,2,3-triazol-1-ylmethyl | H | H | Cl | H | —CH₂C(CH₃)₃ |
| 212. | N—(MeSO₂)—N-(aminoethyl)amino | H | H | Cl | H | H |
| 213. | N—(MeSO₂)—N-(N',N'-di(methyl)aminoethyl)amino | H | H | Cl | H | H |
| 214. | N—(MeSO₂)—N-(N',N'-di(methyl)aminoethyl)amino | H | H | Cl | H | propyl |
| 215. | N—(MeSO₂)—N-(N',N'-di(methyl)aminoethyl)amino | H | H | Cl | H | ethyl |
| 216. | N—(MeSO₂)—N-(N',N'-di(methyl)aminoethyl)amino | H | H | Cl | H | methyl |
| 217. | N—(MeSO₂)—N-(N',N'-di(ethyl)aminoethyl)amino | H | Cl | H | H | H |
| 218. | N—(MeSO₂)—N-(N',N'-di(propyl)aminoethyl)amino | H | H | Cl | H | H |
| 219. | N—(MeSO₂)—N-(N',N'-di(t-butylmethyl)aminoethyl)amino | H | H | Cl | H | H |
| 220. | N—(MeSO₂)—N-(N',N'-di(isobutyl)aminoethyl)amino | H | H | Cl | H | H |
| 221. | N—(MeSO₂)—N-(N',N'-di(CypCH₂)aminoethyl)amino | H | H | Cl | H | H |
| 222. | N—(MeSO₂)—N-(N',N'-di(2-furylCH₂)aminoethyl)amino | H | H | Cl | H | H |
| 223. | N—(MeSO₂)—N-(N',N'-di(2-thienylCH₂)aminoethyl)amino | H | H | Cl | H | H |
| 224. | N—(MeSO₂)—N-(N',N'-di(benzyl)aminoethyl)amino | H | H | Cl | H | H |
| 225. | 1-methyl-2-oxo-imidazolin-3-yl | H | H | Cl | H | H |

TABLE 4

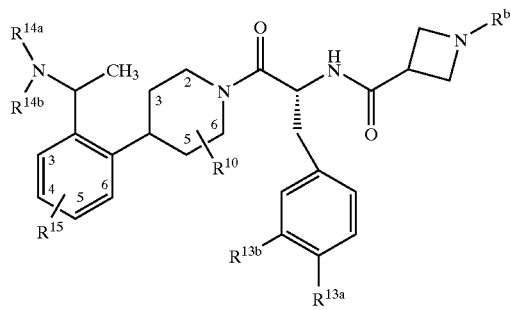

| # | R14a | R14b | R15 | R10 | R13a | R13b | Rb |
|---|---|---|---|---|---|---|---|
| 226. | cyclopropylmethyl | methyl | H | H | Cl | H | H |
| 227. | cyclopropylmethyl | H | H | H | Cl | H | H |
| 228. | methylcarbonyl | methyl | H | H | Cl | H | CypCH₂ |
| 229. | isobutyl | methyl | H | H | Cl | H | H |
| 230. | propyl | methyl | H | H | Cl | H | H |
| 231. | methylsulfonyl | methyl | H | H | Cl | H | H |
| 232. | ethyl | methyl | H | H | Cl | H | H |
| 233. | ethoxycarbonylcyclopropylmethyl | methyl | H | H | Cl | H | H |
| 234. | isopentyl | methyl | H | H | Cl | H | H |
| 235. | 4-methylcarbonylaminobenzyl | methyl | H | H | Cl | H | H |
| 236. | methyl | H | 4-Br | H | Cl | H | H |
| 237. | methylcarbonyl | methyl | H | H | Cl | H | isobutyl |
| 238. | methylcarbonyl | methyl | H | H | Cl | H | ethyl |
| 239. | methylcarbonyl | methyl | H | H | Cl | H | H |
| 240. | methylcarbonyl | methyl | H | H | Cl | H | isopropyl |
| 241. | cyclohexylmethyl | methyl | H | H | Cl | H | H |
| 242. | methyl | methyl | H | H | Cl | H | H |
| 243. | 3-thienylmethyl | methyl | H | H | Cl | H | H |
| 244. | benzyloxyethyl | methyl | H | H | Cl | H | H |

TABLE 4-continued

| # | R$^{14a}$ | R$^{14b}$ | R$^{15}$ | R$^{10}$ | R$^{13a}$ | R$^{13b}$ | R$^b$ |
|---|---|---|---|---|---|---|---|
| 245. | 2-methoxybenzyl | methyl | H | H | Cl | H | H |
| 246. | methyl | H | H | H | Cl | H | H |
| 247. | 4-pyridylmethyl | methyl | H | H | Cl | H | H |
| 248. | 2-pyrrolidinylmethyl | methyl | H | H | Cl | H | H |
| 249. | 3-methoxybenzyl | methyl | H | H | Cl | H | H |
| 250. | benzyl | methyl | H | H | Cl | H | H |
| 251. | aminoethyl | methyl | H | H | Cl | H | H |
| 252. | 4-methoxybenzyl | methyl | H | H | Cl | H | H |

TABLE 5

| # | R$^6$ |
|---|---|
| 253. | 4-bromophenyl |
| 254. | 2-naphthyl |
| 255. | 1,4-biphenyl |
| 256. | 1-naphthyl |
| 257. | 3,4-dichlorophenyl |
| 258. | 4-methoxyphenyl |
| 259. | 4-iodophenyl |
| 260. | 3-chlorophenyl |
| 261. | 4-trifluoromethylphenyl |
| 262. | 3-pyridyl |

TABLE 6

| # | R$^{19}$ | R$^{16}$ |
|---|---|---|
| 263. | —CH$_2$cyp | 6-quinolyl |
| 264. | —CH$_2$cyp | 4-(benzyloxy)phenyl |
| 265. | —CH$_2$cyp | —CH$_2$CH$_2$NHCH$_3$ |
| 266. | —CH$_2$cyp | 3,4-dimethoxyphenyl |
| 267. | —CH$_2$cyp | 4-(phenoxy)phenyl |
| 268. | —CH$_2$cyp | —CH$_2$CH$_2$NH$_2$ |
| 269. | —CH$_2$cyp | 4-piperidyl |
| 270. | —CH$_2$cyp | 4-fluorophenyl |
| 271. | —CH$_2$cyp | 4-(1-pyrrolyl)phenyl |
| 272. | —CH$_2$cyp | 5-methoxyindol-2-yl |
| 273. | —CH$_2$cyp | 3-quinolyl |
| 274. | —CH$_2$cyp | 3-cyanophenyl |
| 275. | —CH$_2$cyp | 4-(1-isobutyl)piperidyl |
| 276. | —CH$_2$cyp | 4-(1-ethyl)piperidyl |
| 277. | propyl | 3-fluorophenyl-CH$_2$— |
| 278. | —CH$_2$cyp | 3-methoxyphenyl |
| 279. | propyl | 2-CF$_3$-phenyl-CH$_2$— |
| 280. | —CH$_2$cyp | 2-methylthiophenyl |
| 281. | —CH$_2$cyp | —CH(Me)phenyl |
| 282. | —CH$_2$cyp | 3,4-dimethoxyphenyl-CH$_2$CH$_2$ |
| 283. | —CH$_2$cyp | 3-fluorophenyl |

TABLE 6-continued

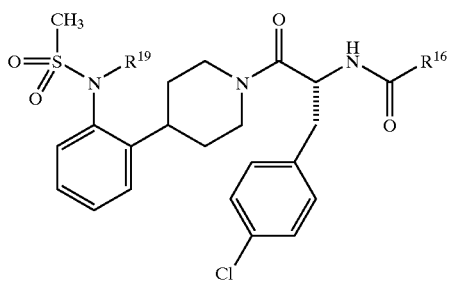

| # | R<sup>19</sup> | R<sup>16</sup> |
|---|---|---|
| 284. | —CH$_2$cyp | 4-pyridyl |
| 285. | —CH$_2$cyp | 4-(1-methyl)piperidyl |
| 286. | —CH$_2$cyp | 3-(aminomethyl)phenyl |
| 287. | —CH$_2$cyp | 2-methylthio pyrid-3-yl |
| 288. | —CH$_2$cyp | 1-aminochxl |
| 289. | —CH$_2$cyp | (1-phenyl)aminomethyl |
| 290. | —CH$_2$cyp | 3-tetrahydrofuranyl |
| 291. | —CH$_2$cyp | 2-thienyl |
| 292. | —CH$_2$cyp | 2-indolyl |
| 293. | —CH$_2$cyp | cyclohexyl |
| 294. | —CH$_2$cyp | 1-aminoethyl |
| 295. | —CH$_2$cyp | 3-piperidyl |
| 296. | —CH$_2$cyp | phenyl |
| 297. | —CH$_2$cyp | 4-chlorophenyl |
| 298. | —CH$_2$cyp | 2-(4-pyridyl)oxazolyl |
| 299. | propyl | 3-fluorophenyl |
| 300. | propyl | 2-fluorophenyl |
| 301. | —CH$_2$cyp | 2-naphthyl |
| 302. | —CH$_2$cyp | 3-indolyl |
| 303. | —CH$_2$cyp | 3-pyridyl |
| 304. | —CH$_2$cyp | 3-isoquinolyl |
| 305. | —CH$_2$cyp | 1-methylcyclopropyl |
| 306. | —CH$_2$cyp | 2-chlorophenyl |
| 307. | —CH$_2$cyp | phenyl(1-amino)ethyl |
| 308. | —CH$_2$cyp | 2-(1,2,3,4-tetrahydronaphthyl) |
| 309. | —CH$_2$cyp | phenyl-HC=C(CH$_3$)— |
| 310. | —CH$_2$cyp | isopropyl |
| 311. | —CH$_2$cyp | phenyl-CH(CH$_3$)CH$_2$— |
| 312. | —CH$_2$cyp | phenyl(1-hydroxy)ethyl |
| 313. | —CH$_2$cyp | 3-indolylethyl |
| 314. | propyl | 2-fluorophenylethyl |
| 315. | —CH$_2$cyp | 1-phenoxypropyl |
| 316. | —CH$_2$cyp | —CH$_2$C(CH$_3$)$_3$ |
| 317. | propyl | 1-(4-fluoronaphthyl) |
| 318. | H | 4-aminochxl |
| 319. | —CH$_2$cyp | 2-benzothienyl |
| 320. | —CH$_2$cyp | 2-(1-methylindolyl) |
| 321. | —CH$_2$cyp | 5-(4-chloro-1,3-dimethyl) pyridylpyrazolyl |
| 322. | —CH$_2$cyp | 2-indanylCH$_2$— |
| 323. | H | 3-aminocyclopentyl- |
| 324. | H | 5-indolyl |
| 325. | —CH$_2$cyp | phenyl(1-methylamino)ethyl |
| 326. | —CH$_2$cyp | 3-indolylCH$_2$— |
| 327. | H | 1-methyl-pyrrolidin-5-yl |
| 328. | H | 3-phenyl-2-pyrrolidinyl |
| 329. | —CH$_2$cyp | 2-(7-pyridyl)oxazolyl |
| 330. | —CH$_2$cyp | 2-benzoxazolyl |
| 331. | —CH$_2$cyp | 2-methoxyphenyl |

TABLE 6-continued

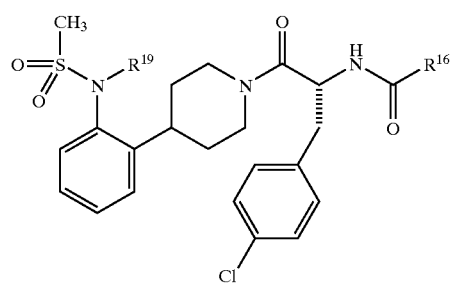

| # | R<sup>19</sup> | R<sup>16</sup> |
|---|---|---|
| 332. | —CH$_2$cyp | 3-(phenoxy)phenyl |
| 333. | —CH$_2$cyp | 2-benzofuran |
| 334. | H | 3-pyridylethyl |
| 335. | H | 1-methyl-5-pyridyl-2-oxo-pyrrolidin-4-yl |
| 336. | —CH$_2$cyp | 4-dimethylaminophenyl-CH$_2$— |
| 337. | propyl | (2,5-di-trifluoromethylphenyl)ethyl |
| 338. | —CH$_2$cyp | 2-methyl-3-indolyl |
| 339. | —CH$_2$cyp | 1-(benzylamino)ethyl |
| 340. | H | 2-(4-pyridyloxazolyl) |
| 341. | H | 2-quinolyl |
| 342. | propyl | 4-piperidyl |
| 343. | CypCH$_2$— | 4-ethoxycarbonylpiperid-1-yl |
| 344. | CypCH$_2$— | 1-piperazinyl |
| 345. | CypCH$_2$— | 4-Boc-piperid-1-yl |
| 346. | propyl | 3-CF$_3$-phenyl |
| 347. | propyl | 4-CF$_3$-phenyl |
| 348. | CypCH$_2$— | 3-CF$_3$-phenyl |
| 349. | CypCH$_2$— | 4-CF$_3$-phenyl |
| 350. | propyl | 4-fluorophenyl |
| 351. | propyl | 2-naphthyl |
| 352. | propyl | phenyl |
| 353. | propyl | 3-pyridyl |
| 354. | propyl | 4-pyridyl |
| 355. | CypCH$_2$— | 4-pyridyl |
| 356. | CypCH$_2$— | 4-(benzyl)phenyl |
| 357. | CypCH$_2$— | 4-(phenylamino)phenyl |
| 358. | CypCH$_2$— | 2-(phenylethyl)phenyl |
| 359. | CypCH$_2$— | 1-(cyclopentyl)-1-(phenyl)methyl |
| 360. | CypCH$_2$— | 4-(tert-butyl)phenyl |
| 361. | CypCH$_2$— | 1-methyl-2-indolyl |
| 362. | CypCH$_2$— | 5-nitro-3-phenyl-2-indolyl |
| 363. | CypCH$_2$— | 4-chloro-1,3-dimethyl-1H-pyrazolo[3,4-b]pyrid-6-yl |
| 364. | CypCH$_2$— | 2-(4-chlorophenyloxy)-2-methylethyl |
| 365. | CypCH$_2$— | 3-chlorophenyl |
| 366. | H | 1-methyl-2-pyrrolyl |
| 367. | H | 2-oxo-1-pyrrolyl |
| 368. | H | 2-oxo-5-pyrrolyl |
| 369. | CypCH$_2$— | 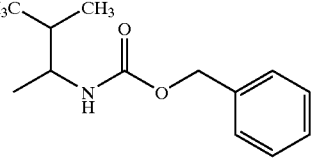 |

TABLE 7

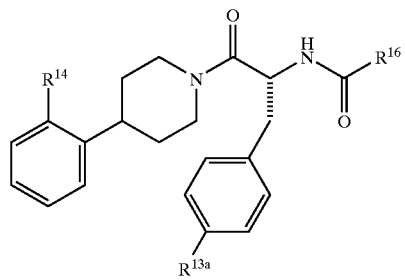

| # | R14 | R16 | R13a |
|---|---|---|---|
| 370. | 1-(N-(CypCH2)amino)ethyl | 6-quinolyl | Cl |
| 371. | 1-(N,N-(CypCH2)2amino)ethyl | 6-quinolyl | Cl |
| 372. | 1-(N-(CypCH2)-N-propylamino)ethyl | 6-quinolyl | Cl |
| 373. | (N,N-(CypCH2)2amino)CH2— | 6-quinolyl | Cl |
| 374. | N-(CypCH2)-N-propylaminomethyl | 6-quinolyl | Cl |
| 375. | N-(CypCH2)-N-ethylaminomethyl | 6-quinolyl | Cl |
| 376. | N,N-(propyl)2aminomethyl | 6-quinolyl | Cl |
| 377. | 1-(N-(CypCH2)-N-butylamino)ethyl | 6-quinolyl | Cl |
| 378. | 1-(N-CypCH2)-N-isopentylamino)ethyl | 6-quinolyl | Cl |
| 379. | 1-(N-(CypCH2)-N-(ChxlCH2)amino)ethyl | 6-quinolyl | Cl |
| 380. | 1-(N-(CypCH2)-N-(CH3S(CH2)3)amino)ethyl | 6-quinolyl | Cl |
| 381. | N-(CypCH2)-N-(MeSO2)aminomethyl | 6-quinolyl | Cl |
| 382. | 1-(N-CypCH2)-N-(3-thienylmethyl)amino)ethyl | 6-quinolyl | Cl |
| 383. | 1-(N-CypCH2)-N-(CH3C═O)amino)ethyl | 6-quinolyl | Cl |
| 384. | 1-hydroxyethyl | 6-quinolyl | Cl |
| 385. | 1-(N-(CypCH2)-N-isobutylamino)ethyl | 6-quinolyl | Cl |
| 386. | 1-(N-(CypCH2)-N-(phenylethyl)amino)ethyl | 6-quinolyl | Cl |
| 387. | N-(CypCH2)-N-(MeSO2)aminomethyl | 6-quinolyl | Cl |
| 388. | 1-(N-(CypCH2)-N-(pentyl)amino)ethyl | 6-quinolyl | Cl |
| 389. | N,N-di(isobutyl)aminomethyl | 6-quinolyl | Cl |
| 390. | 1-(N-(CypCH2)-N-(2-ethylbutyl)amino)ethyl | 6-quinolyl | Cl |
| 391. | 1-(N-(CypCH2)-N-(3-methylphenyl)amino)ethyl | 6-quinolyl | Cl |
| 392. | N-(MeSO2)-N-(CypCH2)aminomethyl | 3-isoquinolyl | Cl |
| 393. | 1-(N-(CypCH2)amino)ethyl | 3-isoquinolyl | Cl |
| 394. | N-(MeSO2)-N-(CypCH2)aminomethyl | 4-piperidyl | Cl |
| 395. | N-propyl-N-(CypCH2)aminomethyl | piperid-1-ylethyl | Cl |
| 396. | 1,2,3-triazol-1-ylmethyl | 1-ethylpiperid-4-yl | Cl |
| 397. | N-propyl-N-(CypCH2)aminomethyl | 1-isobutylpiperid-4-yl | Cl |
| 398. | N-isopropyl-N-(CypCH2)aminomethyl | 1-ethylpiperid-4-yl | Cl |
| 399. | N-ethyl-N-(CypCH2)aminomethyl | 1-ethylpiperid-4-yl | Cl |
| 400. | N-cyclopentyl-N-(CypCH2)aminomethyl | 1-ethylpiperid-4-yl | Cl |
| 401. | 1,2,3-triazol-1-ylmethyl | 1-isopropylpiperid-4-yl | Cl |
| 402. | 1,2,3-triazol-1-ylmethyl | 1-(CypCH2)piperid-4-yl | Cl |
| 403. | 1,2,3-triazol-1-ylmethyl | 1-isobutylpiperid-4-yl | Cl |
| 404. | 1,2,3-triazol-1-ylmethyl | 1-[(CH3)3CCH2)piperid-4-yl | Cl |
| 405. | N-(CypCH2)-N-propylaminomethyl | 6-quinolyl | Br |
| 406. | N-(CypCH2)-N-propylaminomethyl | 3-quinolyl | Br |
| 407. | N-(CypCH2)-N-propylaminomethyl | 4-piperidyl | Br |
| 408. | N-(CypCH2)-N-propylaminomethyl | 1-ethylpiperid-4-yl | Br |
| 409. | N-propyl-N-(CypCH2)aminomethyl | 1-isobutylpiperid-4-yl | Br |
| 410. | N-(CypCH2)-N-propylaminomethyl | 1-isopropylpiperid-4-yl | Br |
| 411. | N-(CypCH2)-N-propylaminomethyl | 1-(CypCH2)piperid-4-yl | Br |
| 412. | N-(CypCH2)-N-propylaminomethyl | 1-isobutylpiperid-4-yl | Br |
| 413. | N-(CypCH2)-N-propylaminomethyl | 1-[(CH3)3CCH2)piperid-4-yl | Br |
| 414. | N-(CypCH2)-N-propylaminomethyl | piperid-1-ylethyl | Br |
| 415. | N-(CypCH2)-N-propylaminomethyl | ethylaminoethyl | Br |
| 416. | 1-(N-(CypCH2)amino)ethyl | 2-quinolyl | Cl |
| 417. | 1-(N-(CypCH2)amino)ethyl | 4-piperidyl | Cl |

TABLE 8

(structure shown)

| # | R[19] | R[8a] |
|---|---|---|
| 418. | —CH₂cyp | (4-methyl-benzo[c]isothiazol-3-yl) |
| 419. | —CH₂cyp | phenyl |
| 420. | —CH₂cyp | benzyl |
| 421. | —CH₂cyp | 1-methylimidazol-4-yl |
| 422. | —CH₂cyp | 3,5-dimethylisoxazol-4-yl |
| 423. | —CH₂cyp | 2-methoxycarbonylthien-3-yl |
| 424. | —CH₂cyp | 4-fluorophenyl |
| 425. | —CH₂cyp | 4-methylcarbonylaminophenyl |
| 426. | —CH₂cyp | 2-(phenylcarbonylaminomethyl)thien-5-yl |
| 427. | —CH₂cyp | 1-naphthyl |
| 428. | —CH₂cyp | 6-quinolyl |
| 429. | —CH₂cyp | 2-(trifluoromethylcarbonyl)-1,2,3,4-tetrahydroisoquinol-7-yl |

Although the pharmacological properties of the compounds of Formula I vary with structural change, in general, activity possessed by compounds of Formula I may be demonstrated in vivo. The pharmacological properties of the compounds of this invention may be confirmed by a number of pharmacological in vitro assays. The exemplified pharmacological assays which follow have been carried out with the compounds according to the invention and their salts.

Biological Evaluation

A number of models exist for the study of obesity (see, e.g., Bray, G. A., 1992, Prog. Brain Res. 93: 333–341; and Bray, G. A., 1989, Amer. J. Clin. Nutr. 5: 891–902). Animals having mutations which lead to syndromes that include obesity symptoms have also been identified.

Attempts have been made to utilize such animals as models for the study of obesity, and the best studied animal models to date for genetic obesity are mice. For reviews, see, e.g., Friedman, J. M. et al., 1991, Mamm. Gen. 1: 130–144; Friedman, J. M. and Liebel, R. L., 1992, Cell 69: 217–220.

Assays which demonstrate MCR4/MCR3 agonistic activity of compounds are well known in the art. One particularly useful assay is the BioTrak™ cAMP direct enzyme immunoassay (EIA) system from Amersham Pharmacia Biotech, which quantitates the cAMP response of cells to MC ligands. This system allows the simple quantitation of total cellular cAMP measurement in cells exposed to selective ligands. Briefly summarized: HEK cells stably transfected with the MC-1, MC-3 or MC-4 receptors are plated into 96 well microtiter plates and grown overnight. Cells are dosed with the appropriate MC ligand for 1 hour and then lysed. A fraction of the lysed cell extract is transferred to the assay plate. The ELISA assay is performed according to kit instructions. Each plate contains a series of cAMP standards for calculating a standard curve, as well as a full MC agonist as a positive control for each MC receptor. cAMP activity is calculated as a % of the maximum cAMP activity of the full MC agonist control.

Penile Erection Test in the Rat

Method that can be used includes a modified version of that reported by Heaton et al. (J. Urol., 145, 1099–1102, 1991.) and Ghasi-Kanzari et al. (Pharmacol. Toxicol., 81, 81–84, 1997.). Rats are kept under a reversed 12-hr light/dark cycle for 5 days prior to testing. On the test day, animals are administered compound via intraperitoneal route of administration 1 hr after the lights go off and then immediately placed in individual Plexiglas cages (32×14×13 cm). Under red lighting, rats are observed for 1 hr. The number of penile erections and yawns are recorded. There are 10 animals per treatment group and bromocriptine (4 mg/kg) is used as the reference agent as well as a vehicle control. Data are analyzed by comparing treated groups with vehicle control using Mann Whitney U tests.

Fast-Induced Food Intake in Mice

Male C57BL/6 mice (25–30 g) were used for studies. Food was removed from group-housed mice (5-8/cage) overnight (16–18 hr). The next day, mice were dosed with compound (in 20% Captisol or HPMC/Tween or PBS, depending on the solubility) and then placed into individual cages. Fifteen min following systemic dosing or 30 min following intracerebroventricular (i.c.v) dosing (i.e., time to recover from anesthesia), a pre-weighed amount of food was placed in each cage. Food was then weighed 1, 2 and 4 hr after replacement. Cumulative food intake was determined as the difference between the initial weight of the food and the weight of the food at each time point. For statistical analysis, food intake values of compound treated animals were compared with that of vehicle treated animals using ANOVA followed by a post-hoc test (i.e., FLSD) when warranted. For these studies, group sizes for each treatment were 8–10 animals. For i.c.v. dosing, animals were anesthetized using isoflurane. Next, the i.c.v. injection was made using a free-hand technique. Mice were allowed 30 min to recover prior to the start of the test.

Examples 11, 12 and 16 caused a reduction in feeding at concentrations of 30 mg/kg or below.

Formulations

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard soft capsules and tablets, with the solid oral preparations being preferred over the liquid preparations.

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The compounds and compositions of the present invention may, for example, be administered orally, mucosally, topically, rectally, pulmonarily such as by inhalation spray, nasal or buccal or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For example, in the case of a 70 kg adult human, these may contain an amount of active ingredient from about 0.7 to 3500 mg, preferably from about 5 to 1500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.1 and about 50 mg/kg body weight and most preferably between about 0.5 to 20 mg/kg body weight, may be appropriate may be appropriate. The daily dose can be administered in one to four doses per day.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules.

Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose for the treatment of sexual disfunction compounds of the present invention can be given orally or as a nasal spray.

In the case of skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula I

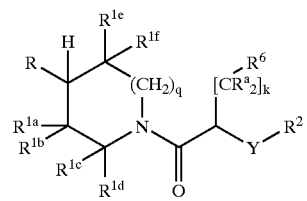

wherein Y is —NH—;

wherein R is phenyl ortho substituted with a radical selected from $R^4$ and optionally substituted with a radical selected from $R^4$;

wherein $R^{1a}$, $R^{1b}$, $R^{1c}$, $R^{1d}$, $R^{1e}$, and $R^{1f}$ are independently selected from $R^4$; or wherein $R^{1a}$ and $R^{1b}$ or $R^{1d}$ and $R^{1c}$ form oxo;

wherein $R^2$ is selected from
a) —$(CH_2)_n$—$C_{3-6}$-cycloalkyl,
b) —$(CH_2)_n$-phenyl,
c) —$(CH_2)_n$-5–10-membered heterocyclyl, and d)

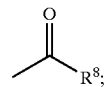

wherein the cycloalkyl and aryl groups are optionally substituted with 1 to 3 radicals selected from $R^4$; and the heterocyclyl groups are optionally substituted with 1 to 3 radicals selected from $R^4$ and oxo;

wherein $R^3$ is independently selected from H, chloro, bromo, iodo, phenyl, fluoro, amino, $C_{1-2}$-alkyl, $C_{1-2}$-haloalkyl, $C_{1-2}$-haloalkoxy, and $C_{1-2}$-alkoxy;

wherein $R^4$ is selected from H, $C_{1-2}$-alkyl, —$(CH_2)_n$—$C_{5-6}$-cycloalkyl, —$(CH_2)_n$-phenyl, —$(CH_2)_n$-4–10-membered heterocyclyl, fluoro, chloro, —$(CH_2)_n$—$OR^{9a}$, —$NR^{9a}SO_2R^7$, —$NR^{9a}R^{9b}$, $C(O)NR^{9a}R^{9b}$, —$NR^{9a}C(O)R^7$, cyano, nitro, —$(CH_2)_n$—$C(O)R^7$, —$C(O)OR^{9a}$, —$(CH_2)_n$—$C(S)R^7$, —$(CH_2)_n$—C=

$(NR^{9a})R^7$, $-NR^{9a}C=(NR^{9a})N(R^7)_2$, $-[C(R^7)_2]_p$ $NR^{9a}R^{9b}$, $-[CH_2]_p NR^{9a}SO_2R^7$, $-[CH_2]_p NR^{9a}C(O)$ $R^7$, $-SO_2NR^{9a}R^{9b}$, $-S(O)_m R^7$, $-C(R^7)_2SO_2CF_3$, $C_{1-2}$-hydroxyalkyl $C_{1-2}$-haloalkyl and $C_{1-2}$-haloalkoxy;

wherein $R^5$ is selected from halo, $-OR^{9a}$, $-NR^{9a}R^{9b}$, $-[C(R^7)_2]_n NR^{9a}R^{9b}$, and $-SO_2NR^{9a}R^{9b}$;

wherein $R^6$ is naphthyl or phenyl optionally substituted with one or two $R^3$;

wherein $R^7$ is selected from H, $C_{1-4}$-alkyl, $-(CH_2)_n-C_{3-6}$-cycloalkyl, $-(CH_2)_n$-4–10-membered heterocyclyl,
$-(CH_2)_n$-phenyl, amino-$C_{1-4}$-alkyl, $C_{1-4}$-alkylamino, $C_{2-4}$-alkenyl, $C_{1-4}$-alkylthio-$C_{1-4}$-alkyl, $C_{1-4}$-alkylcarbonylamino-$C_{1-4}$-alkyl, $C_{1-4}$-alkylamino-$C_{1-4}$-alkyl, $C_{1-4}$-alkoxy-$C_{1-4}$-alkyl and $C_{1-4}$-alkoxy;

wherein $R^8$ is selected from
a) amino-$C_{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenyl-$C_{1-4}$-alkylamino-$C_{1-4}$-alkyl,
f) phenylamino-$C_{1-4}$-alkyl,
g) 4–10-membered heterocyclyl-$C_{1-4}$-alkylamino-$C_{1-4}$-alkyl,
h) N-(4–10-membered heterocyclyl-$C_{1-4}$-alkyl)amino,
i) $C_{1-4}$-alkyl,
j) $C_{3-6}$-cycloalkyl-$(CH_2)$ n—,
k) aryl-$(CH_2)_n$—,
l) 4–10-membered heterocyclyl-$(CH_2)_n$—,
m) $R^{9a}O$—,
n) amino-$C_{1-4}$-alkoxy,
o) phenyl-$C_{1-4}$-alkyl where the alkyl portion is substituted with amino, hydroxy or $C_{1-4}$-alkylamino, and
p) 4–10-membered heterocyclyl-$C_{1-4}$-alkylenyl where the alkylenyl portion is substituted with amino, hydroxy or $C_{1-4}$-alkylamino;
wherein the cycloalkyl and aryl groups are optionally substituted with 1 to 3 groups selected from $R^4$; and the heterocyclyl groups are optionally substituted with 1 to 3 groups selected from $R^4$ and oxo;

wherein $R^{9a}$ is selected from H, $C_{1-6}$-alkyl, $C_{3-6}$-cycloalkyl-$(CH_2)_n$—, 4–10-membered heterocyclyl-$(CH_2)_n$—, and phenyl-$(CH_2)_n$—;

wherein $R^{9b}$ is selected from H, $C_{1-6}$-alkyl, $C_{2-6}$-alkenyl, $C_{3-6}$-cycloalkyl-$(CH_2)_n$—, 4–10-membered heterocyclyl-$(CH_2)_n$—, phenyl-$(CH_2)_n$—, amino-$C_{1-6}$-alkyl, $C_{1-6}$-alkylcarbonylamino-$C_{1-6}$-alkyl, $C_{3-6}$-cycloalkylamino-$C_{1-6}$-alkyl, $C_{3-6}$-cycloalkyl-$C_{1-6}$-alkylamino-$C_{1-6}$-alkyl, 5–6-membered heteroarylamino-$C_{1-6}$-alkyl, 5–6-membered heteroaryl-$C_{1-6}$-alkylamino-$C_{1-6}$-alkyl, phenylamino-$C_{1-6}$-alkyl, phenyl-$C_{1-6}$-alkylamino-$C_{1-6}$-alkyl, 5–6-membered heteroaryloxy-$C_{1-6}$-alkyl, 5–6-membered heteroaryl-$C_{1-6}$-alkyloxy-$C_{1-6}$-alkyl, phenyl-$C_{1-6}$-alkyloxy-$C_{1-6}$-alkyl, phenyloxy-$C_{1-6}$-alkyl, $C_{1-6}$-alkylthio-$C_{1-6}$-alkyl, $C_{1-6}$-alkylamino-$C_{1-6}$-alkyl, $C_{1-6}$-hydroxyalkyl and $C_{1-6}$-alkoxy-$C_{1-6}$-alkyl;

wherein $R^a$ are independently H or methyl;
wherein k is 1;
wherein m is 0, 1 or 2;
wherein n is 0, 1, 2 or 3;
wherein p is 1 or 2; and
wherein q is 1;

and a pharmaceutically-acceptable salt thereof; provided $R^2$ is not $-CO_2$(tert-butyl) when $R^4$ is hydrogen or methoxy and when $R^6$ is phenyl.

2. A compound of claim 1, wherein R is

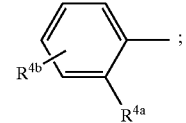

wherein $R^{1a}$, $R^{1b}$, $R^{1c}$, $R^{1d}$, $R^{1e}$, and $R^{1f}$ are H;
wherein $R^2$ is selected from
a) $-(CH_2)_n-C_{3-6}$-cycloalkyl,
b) $-(CH_2)_n$-phenyl, and
c) $-(CH_2)_n$-6–10-membered heterocyclyl;
wherein the cycloalkyl and aryl groups are optionally substituted with 1 to 2 groups selected from $R^{4b}$; and the heterocyclyl group is optionally substituted with 1 to 2 groups selected from $R^{4b}$ and oxo;

wherein $R^3$ is independently selected from H, chloro, bromo, iodo, fluoro, amino, methyl, trifluoromethyl, trifluoromethoxy and methoxy;

wherein $R^{4a}$ is selected from $-(CH_2)_n-OR^{9a}$, $-NR^{9a}SO_2R^{7a}$, 4–6-membered heterocyclyl, $-[CH_2]_p NR^{9a}SO_2R^{7a}$, $-NR^{9a}R^{9b}$, $-C(O)NR^{9a}R^{9b}$, $-NR^{9b}C(O)R^{7a}$, $-[CH_2]_p NR^{9b}C(O)R^{7a}$, $-(CH_2)_n-C(O)R^{7a}$, nitro, $-C(O)OR^{9a}$, $-(CH_2)_n-C(S)R^{7a}$, $-[C(R^{7a})_2]_p NR^{9a}R^{9b}$, $-SO_2NR^{9a}R^{9b}$, $S(O)_m R^{7a}$ and $-C(R^{7a})_2SO_2CF_3$;

wherein $R^{4b}$ is selected from H, $C_{1-2}$-alkyl, $-(CH_2)_n-C_{5-6}$-cycloalkyl, $-(CH_2)_n$-phenyl, $-(CH_2)_n$-4–10-membered heterocyclyl, fluoro, chloro, $-OR^{9a}(CH_2)_n$, $-OR^{9a}$, $-NR^{9a}SO_2R^{7a}$, $-NR^{9a}R^{9b}$, $-C(O)NR^{9a}R^{9b}$, $-NR^{9a}C(O)R^{7b}$, $-(CH_2)_n-C(O)R^{7a}$, nitro, $-C(O)R^{9a}$, $-(CH_2)_n-C(S)R^{7a}$, $-[C(R^{7a})_2]_p NR^{9a}R^{9b}$, $-SO_2NR^{9a}R^{9b}$, $-S(O)_m R^{7a}$, $-C(R^{7a})_2 SO_2CF_3$, cyano, $C_{1-2}$-haloalkyl and $C_{1-2}$-haloalkoxy;

wherein $R^{7a}$ is selected from H, $C_{1-3}$-alkyl, $-(CH_2)_n-C_{3-6}$-cycloalkyl, $-(CH_2)_n$-4–10-membered heterocyclyl and $-(CH_2)_n$-phenyl;

wherein $R^{7b}$ is selected from H, amino-$C_{1-3}$-alkyl, $C_{1-3}$-alkoxy, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl, $C_{1-3}$-alkoxy-$C_{1-3}$-alkyl, H, $C_{1-3}$-alkyl, $-(CH_2)_n-C_{3-6}$-cycloalkyl, $-(CH_2)_n$-4–10-membered heterocyclyl and $-(CH_2)_n$-phenyl;

wherein $R^{9a}$ is selected from H, $C_{1-6}$-alkyl, $C_{5-6}$-cycloalkyl-$(CH_2)_n$—, 4–10-membered heterocyclyl-$(CH_2)_n$—, and phenyl-$(CH_2)_n$—;

wherein $R^{9b}$ is selected from H, $C_{1-6}$-alkyl, $C_{5-6}$-cycloalkyl-$(CH_2)_n$—, 4–10-membered heterocyclyl-$CH_2)_n$—, phenyl-$(CH_2)_n$—, amino-$C_{1-3}$-alkyl, $C_{1-3}$-alkylcarbonylamino-$C_{1-3}$-alkyl, $C_{5-6}$-cycloalkylamino-$C_{1-3}$-alkyl, $C_{5-6}$-cycloalkyl-$C_{1-3}$-alkylamino-$C_{1-3}$-alkyl, 5–6-membered heteroarylamino-$C_{1-3}$-alkyl, 5–6-membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6-membered heteroaryloxy-$C_{1-3}$-alkyl, 5–6-membered heteroaryl-$C_{1-3}$-alkyloxy-$C_{1-3}$-alkyl, phenyl-$C_{1-3}$-alkyloxy-$C_{1-3}$-alkyl, phenyloxy-$C_{1-3}$-alkyl, $C_{1-3}$-alkylthio-$C_{1-3}$-alkyl, $C_{1-3}$-alkylamino-$C_{1-3}$-alkyl, $C_{1-3}$-hydroxyalkyl and $C_{1-3}$-alkoxy-$C_{1-3}$-alkyl;

wherein $R^a$ are H;
wherein k is 1;
wherein m is 2;
wherein n is 0, 1, 2 or 3; and wherein p is 1 or 2;
and a pharmaceutically-acceptable salt thereof.

3. A compound of claim 2, wherein R is

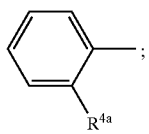

wherein $R^2$ is selected from indolyl$(CH_2)_n$—, phenyl$(CH_2)_n$—, benzoxazolyl$(CH_2)_n$—, oxazolo[4,5-b]pyridyl$(CH_2)_n$—, oxazolo[5,4-b]pyridyl$(CH_2)_n$—, benzoxazolyl$(CH_2)_n$—, 1,2,3,4-tetrahydro-isoquinolyl$(CH_2)_n$—, pyridyl$(CH_2)_n$— and 2,3-dihydro-benzo[1,4]dioxanyl$(CH_2)_n$—;
wherein $R^2$ is optionally substituted with 1 to 2 groups selected from $R^{4b}$;
wherein $R^3$ is independently selected from H, chloro, bromo, amino, methyl, trifluoromethyl and methoxy;
wherein $R^{4a}$ is selected from 4–5-membered heterocyclyl, —$NR^{9a}SO_2R^{7a}$, —$NR^{9a}R^{9b}$, —$C(O)NR^{9a}R^{9b}$, —$C_{1-3}$—$NR^{9a}SO_2R^{7a}$, —$C_{1-3}$—$NR^{9a}C(O)R^{7b}$, —$NR^{9b}C(O)R^{7a}$ and —$C_{1-3}$—$NR^{9a}R^{9b}$;
wherein $R^6$ is phenyl optionally substituted with one or two $R^3$;
wherein $R^{7a}$, is selected from H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;
wherein $R^{7b}$ is selected from H, amino-$C_{1-3}$-alkyl, $C_{1-3}$-alkoxy, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl, $C_{1-3}$-alkoxy-$C_{1-3}$-alkyl, H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;
wherein $R^{9a}$ is selected from H, $C_{1-6}$-alkyl, $C_{5-6}$-cycloalkyl-$(CH_2)_n$—, 4–10-membered heterocyclyl-$(CH_2)_n$—, and phenyl-$(CH_2)_n$—;
wherein $R^{9b}$ is selected from H, $C_{1-6}$-alkyl, $C_{5-6}$-cycloalkyl-$(CH_2)_n$—, 4–10-membered heterocyclyl-$(CH_2)_n$—, phenyl-$(CH_2)_n$—, amino-$C_{1-3}$-alkyl, $C_{1-3}$-alkylcarbonylamino-$C_{1-3}$-alkyl, $C_{5-6}$-cycloalkylamino-$C_{1-3}$-alkyl, $C_{5-6}$-cycloalkyl-$C_{1-3}$-alkylamino-$C_{1-3}$-alkyl, 5–6-membered heteroarylamino-$C_{1-3}$-alkyl, 5–6-membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6-membered heteroaryloxy-$C_{1-3}$-alkyl, 5–6-membered heteroaryl-$C_{1-3}$-alkyloxy-$C_{1-3}$-alkyl, phenyl-$C_{1-3}$-alkyloxy-$C_{1-3}$-alkyl, phenyloxy-$C_{1-3}$-alkyl, $C_{1-3}$-alkylthio-$C_{1-3}$-alkyl, $C_{1-3}$-alkylamino-$C_{1-3}$-alkyl, $C_{1-3}$-hydroxyalkyl and $C_{1-3}$-alkoxy-$C_{1-3}$-alkyl;
wherein k is 1;
wherein m is 2;
wherein n is 0, 1, 2 or 3; and
wherein p is 1 or 2;
and a pharmaceutically-acceptable salt thereof.

4. A compound of claim 1 wherein R is

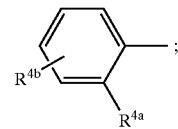

wherein $R^{1a}$, $R^{1b}$, $R^{1c}$, $R^{1d}$, $R^{1e}$, and $R^{1f}$ are H;
wherein $R^2$ is selected from

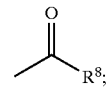

wherein $R^3$ is independently selected from H, chloro, bromo, iodo, fluoro, amino, methyl, trifluoromethyl, trifluoromethoxy and methoxy;
wherein $R^{4a}$ is selected from —$C_{1-2}$-alkyl-$NR^{9a}SO_2R^{7a}$, —$NR^{9a}SO_2R^{7a}$, 4–5-membered heterocyclyl —$NR^{9a}R^{9b}$, —$C(O)NR^{9a}R^{9b}$, —$C_{1-2}$-alkyl-$NR^{9a}C(O)R^{7b}$, —$NR^{9b}C(O)R^{7a}$ and —$C_{1-2}$-alkyl-$NR^{9a}R^{9b}$;
wherein $R^{4b}$ is selected from H, $C_{1-2}$-alkyl, —$(CH_2)_n$—$C_{5-6}$-cycloalkyl, —$(CH_2)_n$-phenyl, —$(CH_2)_n$-4–10-membered heterocyclyl, fluoro, chloro, —$OR^7$, —$NR^7SO_2R^7$, —$N(R^7)_2$, cyano, —$(CH_2)_n$—$C(O)R^7$, —$C(O)OR^7$, —$(CH_2)_n$—$C(S)R^7$, —$[C(R^7)_2]_pN(R^7)_2$, —$SO_2N(R^7)_2$, —$S(O)_mR^7$, —$C(R^7)_2SO_2CF_3$, $C_{1-2}$-haloalkyl and $C_{1-2}$-haloalkoxy;
wherein $R^5$ is selected from chloro, fluoro, hydroxyl, —$NR^{7a}R^{7b}$ and —$SO_2N(R^{7a})_2$;
wherein $R^6$ is phenyl optionally substituted with one or two $R^3$;
wherein $R^{7a}$ is selected from H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;
wherein $R^{7b}$ is selected from H, amino-$C_{1-3}$-alkyl, $C_{1-3}$-alkoxy, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl, $C_{1-3}$-alkoxy-$C_{1-3}$-alkyl, H, $C_{1-3}$-alkyl, —$(CH_2)_n$—$C_{3-6}$-cycloalkyl, —$(CH_2)_n$-4–10-membered heterocyclyl and —$(CH_2)_n$-phenyl;
wherein $R^8$ is selected from
a) amino-$C^{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenylamino-$C_{1-4}$-alkyl,
f) phenyl-$C_{1-2}$-alkylamino-$C_{1-4}$-alkyl,
g) 4–10-membered heterocyclyl-$C_{1-4}$-alkylamino-$C_{1-4}$-alkyl,
h) N-(4–10-membered heterocyclyl-$C_{1-4}$-alkyl)amino,
i) $C_{1-4}$-alkyl,
j) $C_{3-6}$-cycloalkyl-$(CH_2)_n$—,
k) aryl-$(CH_2)_n$—,
l) 4–10-membered heterocyclyl-$(CH_2)_n$—,
m) amino-$C_{1-4}$-alkoxy,
n) phenyl-$C_{1-4}$-alkyl where the alkyl portion is substituted with amino, hydroxy or $C_{1-4}$-alkylamino, and
o) 4–10-membered heterocyclyl-$C_{1-4}$-alkylenyl where the alkylenyl portion is substituted with amino, hydroxy or —$C_{1-4}$-alkylamino;
wherein the cycloalkyl and aryl groups are optionally substituted with 1 to 2 groups selected from $R^{4b}$; and the heterocyclyl groups are optionally substituted with 1 to 2 groups selected from $R^{4b}$ and oxo;

wherein $R^{9a}$ is selected from H, $C_{1-6}$-alkyl, $C_{5-6}$-cycloalkyl-$(CH_2)_n$—, 4–10-membered heterocyclyl-$(CH_2)_n$—, and phenyl-$(CH_2)_n$—;

wherein $R^{9b}$ is selected from H, $C_{1-6}$-alkyl, $C_{5-6}$-cycloalkyl-$(CH_2)_n$—, 4–10-membered heterocyclyl-$(CH_2)_n$—, phenyl-$(CH_2)_n$—, amino-$C_{1-3}$-alkyl, $C_{1-3}$-alkylcarbonylamino-$C_{1-3}$-alkyl, $C_{5-6}$-cycloalkylamino-$C_{1-3}$-alkyl, $C_{5-6}$-cycloalkyl-$C_{1-3}$-alkylamino-$C_{1-3}$-alkyl, 5–6-membered heteroarylamino-$C_{1-3}$-alkyl, 5–6-membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6-membered heteroaryloxy-$C_{1-3}$-alkyl, 5–6-membered heteroaryl-$C_{1-3}$-alkyloxy-$C_{1-3}$-alkyl, phenyl-$C_{1-3}$-alkyloxy-$C_{1-3}$-alkyl, phenyloxy-$C_{1-3}$-alkyl, $C_{1-3}$-alkylthio-$C_{1-3}$-alkyl, $C_{1-3}$-alkylamino-$C_{1-3}$-alkyl, $C_{1-3}$-hydroxyalkyl and $C_{1-3}$-alkoxy-$C_{1-3}$-alkyl;

wherein $R^a$ are H;
wherein k is 1;
wherein m is 2;
wherein n is 0, 1, 2 or 3; and
wherein p is 1 or 2;
and a pharmaceutically-acceptable salt thereof.

5. A compound of claim 4 wherein $R^8$ is

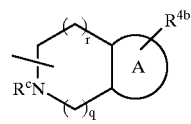

or optionally substituted azetidinyl;
wherein A is selected from phenyl or 5–6-membered heteroaryl;
wherein $R^c$ is H or methyl; r is 0 or 1; and q is 0 or 1.

6. Compound of claim 5 wherein $R^8$ is

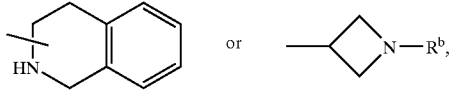

where $R^b$ is selected from H, $C_{1-6}$-alkyl, $C_{5-6}$-cycloalkyl-$(CH_2)$—, 4–10-membered heterocyclyl-$(CH_2)_n$- and phenyl-$(CH_2)_n$—.

7. A compound of claim 1 and pharmaceutically acceptable salts thereof selected from ((3S)(3-1,2,3,4-tetrahydroisoquinolyl))-N-{(1R)-2-[4-(2-methoxyphenyl)-piperidyl]-2-oxo-1-benzylethyl}carboxamide;

N-[(1R)-1-[(4-chlorophenyl)methyl]-2-(4-{2-[(methylsulfonyl)amino]phenyl}-piperidyl)-2-oxoethyl]((3S)(3-1,2,3,4-tetrahydroisoquinolyl))carboxamide;

N-[(1R)-1-[(4-chlorophenyl)methyl]-2-(4-{2-[(methylsulfonyl)amino]phenyl}-piperidyl)-2-oxoethyl]((2S)-1-methylpyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]((3S,1R)-3-aminocyclopentyl)carboxamide;

N-[(1R)-1-[(4-chlorophenyl)methyl]-2-(4-{2-[(methylsulfonyl)amino]phenyl}-piperidyl)-2-oxoethyl]((1S,3R)-3-aminocyclopentyl)carboxamide;

N-[(1R)-1-[(4-chlorophenyl)methyl]-2-(4-{2-[(methylsulfonyl)amino]phenyl}-piperidyl)-2-oxoethyl](5-oxopyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]azetidin-3-ylcarboxamide;

N-[(1R)-1-[(4-chlorophenyl)methyl]-2-(4-{2-[(methylsulfonyl)amino]phenyl}-piperidyl)-2-oxoethyl]-2-(4-piperidyl)acetamide;

N-[(1R)-1-[(4-chlorophenyl)methyl]-2-(4-{2-[(methylsulfonyl)amino]phenyl}-piperidyl)-2-oxoethyl]((2S,3R)-3-phenylpyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]((2S)pyrrolidin-2-yl)carboxamide;

((3S)(3-1,2,3,4-tetrahydroisoquinolyl))-N-[(1R)-1-[(3,4-dichlorophenyl)methyl]-2-(4-{2-[(methylsulfonyl)amino]phenyl}piperidyl)-2-oxoethyl]carboxamide;

N-[(1R)-1-[(4-chlorophenyl)methyl]-2-(4-{2-[(cyclopropylmethyl)-(methylsulfonyl)amino]phenyl}piperidyl)-2-oxoethyl]((3S)(3-1,2,3,4-tetrahydroisoquinolyl))carboxamide;

N-[(1R)-1-[(4-cChlorophenyl)methyl]-2-(4-{2-[(cyclopropylmethyl)-(methylsulfonyl)amino]phenyl}-piperidyl)-2-oxoethyl]azetidin-3-ylcarboxamide;

N-((1R)-1-[(4-chlorophenyl)methyl]-2-oxo-2-{4-[2-(trifluoromethyl)phenyl]-piperidyl}ethyl)((3S)(3-1,2,3,4-tetrahydroisoquinolyl))carboxamide;

N-((1R)-1-[(4-chlorophenyl)methyl]-2-{4-[2-(hydroxyethyl)phenyl]piperidyl}-2-oxoethyl)((3S)(3-1,2,3,4-tetrahydroisoquinolyl))carboxamide;

N-[(1R)-2-(4-{2-[(2-aminoethyl)(methylsulfonyl)amino]-phenyl}piperidyl)-1-[(4-chlorophenyl)methyl]-2-oxoethyl]((3S)(3-1,2,3,4-tetrahydroisoquinolyl))-carboxamide;

((3S)(3-1,2,3,4-tetrahydroisoquinolyl))-N-((1R)-1-[(4-chlorophenyl)methyl]-2-{4-[2-(3-methyl-2-oxo(4-imidazolinyl))phenyl]piperidyl}-2-oxoethyl)carboxamide;

((3S)(3-1,2,3,4-tetrahydroisoquinolyl))-N-((1R)-1-[(4-chlorophenyl)methyl]-2-oxo-2-{4-[2-(2-oxo(4-imidazolinyl))phenyl]piperidyl}ethyl)carboxamide;

N-((1R)-1-[(4-chlorophenyl)methyl]-2-oxo-2-{4-[2-(2-oxo(4-imidazolinyl))phenyl]-piperidyl}ethyl)azetidin-3-ylcarboxamide;

tert-butyl 3-(N-{(1R)-2-[4-(2-aminophenyl)piperidyl]-[(4-chlorophenyl)methyl]-2-oxoethyl}carbamoyl} (3S)-1,2,3,4-tetrahydroisoguinoline-2-carboxylate;

N-{(1R)-1-[(4-chlorophenyl)methyl]-2-[4-(2-{[(2-cyanophenyl)sulfonyl]amino}-phenyl)piperidyl]-2-oxoethyl}((3S)(3-1,2,3,4-tetrahydroisoquinolyl))carboxamide;

N-{(1R)-1-[(4-chlorophenyl)methyl]-2-oxo-2-[4-(2-{[(2,4,6-trimethylphenyl)sulfonyl]amino}phenyl)piperidyl]ethyl}((3S)(3-1,2,3,4-tetrahydroisoquinolyl))carboxamide;

N-[(1R)-1-[(4-chlorophenyl)methyl]-2-(4-{2-[(methylamino)carbonylamino]-phenyl}piperidyl)-2-oxoethyl]((3S)(3-1,2,3,4-tetrahydroisoquinolyl))carboxamide;

N-((1R)-1-[(4-chlorophenyl)methyl]-2-{4-(2-(methoxycarbonylamino)phenyl]piperidyl}-2-oxoethyl)((3S)(3-1,2,3,4-tetrahydroisoquinolyl))carboxamide;

N-[(1R)-1-[(4-chlorophenyl)methyl]-2-(4-{2-[(cyclopropylmethyl)amino]-phenyl}piperidyl)-2- oxoethyl]((3S)(3-1,2,3,4-tetrahydroisoquinolyl))carboxamide; and

N-[(1R)-2-(4-{2-[(2-aminoethyl)amino]phenyl}piperidyl)-1-[(4-chlorophenyl)methyl]-2-oxoethyl]((3S)(3-1,2,3,4-tetrahydroisoquinolyl))carboxamide.

8. A compound of Formula II

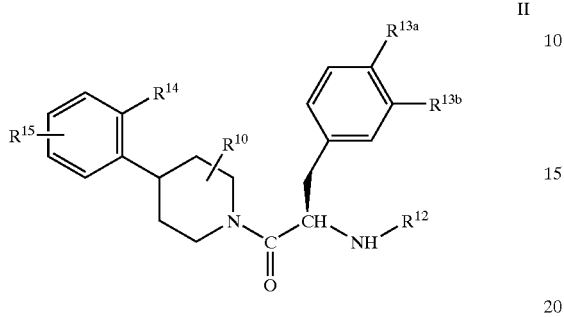

II wherein $R^{10}$ is selected from H, chloro or fluoro; or wherein $R^{10}$ is a $C_{1-4}$-alkylene bridge;

wherein $R^{12}$ is selected from optionally substituted phenyl-$C_{1-2}$-alkylenyl, optionally substituted 5–10 membered heteroaryl and

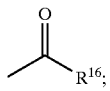

provided the optionally substituted heterocyclyl is not nitro substituted;

wherein $R^{13a}$ and $R^{13b}$ are independently selected from H, fluoro, iodo, bromo, chloro, $C_{1-2}$-alkyl, $C_{1-2}$-haloalkyl, phenyl, and $C_{1-2}$-alkoxy; or wherein $R^{13a}$ and $R^{13b}$ together form an $C_{1-4}$-alkenylenyl bridge;

wherein $R^{14}$ is selected from $R^{19}R^{20}N-$, $R^{19}R^{20}N-C_{1-4}$-alkyl, $(R^{21}R^{22}N-)(O=)C-$, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;

wherein $R^{15}$ is selected from H, $C_{1-2}$-haloalkyl, $C_{1-4}$-alkyl, halo, $-OR^{17}$, and $-N(R^{17})_2$;

wherein $R^{16}$ is selected from
a) 4–6 membered saturated heterocyclyl,
b) 10 membered partially unsaturated heterocyclyl,
c) 5–10 membered heteroaryl,
d) $C_{1-4}$-aminoalkyl,
e) $C_{1-4}$-aminoalkylamino,
f) $C_{1-4}$-alkylamino-$C_{1-4}$-alkylamino,
g) $C_{1-4}$-alkylamino-$C_{1-4}$-alkyl,
h) arylamino-$C_{1-4}$-alkyl,
i) aryl-$C_{1-4}$-alkylamino-$C_{1-4}$alkyl,
j) heterocyclyl-$C_{1-4}$-alkylamino-$C_{1-4}$-alkyl,
k) aryl, provided if 2-substituted aryl, is 2-substituted with amino or chloro,
l) $C_{1-4}$-alkyl,
m) aralkyl,
n) heterocyclyl-$C_{1-4}$-alkyl, provided $R^{16}$ is not 3-methylindol-1-ylethyl,
o) $C_{5-6}$-cycloalkyl,
p) $C_{1-4}$-aminoalkoxy,
q) heterocyclyl-$C_{1-4}$-alkoxy,
r) N-(heterocyclyl-$C_{1-4}$-alkyl)amino,
s) aryl-$C_{1-4}$-alkyl where the alkyl portion is substituted with amino, hydroxy or $-C_{1-4}$-alkylamino, and
t) heterocyclyl-$C_{1-4}$-alkylenyl where the alkylenyl portion is substituted with amino, hydroxy or $-C_{1-4}$-alkylamino;

wherein $R^{17}$ is selected from H, $C_{1-4}$-alkyl, $C_{3-7}$-cycloalkyl-$(CH_2)_n-$, and aryl-$(CH_2)_n-$;

wherein $R^{19}$ is selected from H, $R^{23}SO_2-$, $C_{1-6}$-alkyl, $C_{3-7}$-cycloalkyl-$(CH_2)_n-$, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;

wherein $R^{20}$ is selected from H, $C_{1-8}$-alkyl, $C_{3-7}$-cycloalkyl-$(CH_2)_n-$, $C_{1-3}$-alkylsulfonyl, amino-$C_{1-3}$-alkyl, heterocyclyl-$(CH_2)_n-$, and aryl-$(CH_2)_n$;

alternatively $R^{19}$ and $R^{20}$ together with the nitrogen atom form a 4–8 membered heterocyclic ring;

wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$alkyl, amino-$C_{1-6}$-alkyl, heterocyclyl-$(CH_2)_n-$, $C_{3-7}$-cycloalkyl-$(CH_2)_n-$, and aryl-$(CH_2)_n-$;

wherein $R^{22}$ is selected from H, $C_{1-6}$-alkyl, $C_{3-7}$-cycloalkyl-$(CH_2)_n-$, heterocyclyl-$(CH_2)_n-$ and aryl-$(CH_2)_n-$;

alternatively $R^{21}$ and $R^{22}$ together with the amide nitrogen atom form a 4–7 membered saturated heterocyclic ring;

wherein $R^{23}$ is selected from H, $C_{1-6}$-alkyl, $C_{3-7}$-cycloalkyl-$(CH_2)_n-$, heterocyclyl-$(CH_2)_n-$ and aryl-$(CH_2)_n-$;

wherein n is 0, 1, 2 or 3; and wherein m is 0, 1 or 2;

wherein aryl, heterocyclyl and cycloalkyl are optionally substituted with one or more substituents selected from $C_{1-2}$-haloalkyl, $C_{1-3}$-alkyl, $C_{3-6}$-cycloalkyl-$(CH_2)_n-$, chloro, fluoro, $-OR^{17}$, $-NR^{17}SO_2R^{17}$, $N(R^{17})_2$, cyano, $-COR^{17}$, $-C(R^{17})_2N(R^{17})$ 2, nitro, $-SO_2N(R^{17})_2$, $S(O)_mR^{17}$, and $C_{1-3}$-haloalkoxy;

and a pharmaceutically-acceptable salt thereof.

9. A compound of claim 8 wherein $R^{10}$ is H;

wherein $R^{13a}$ is selected from H, bromo, chloro, phenyl, trifluoromethyl and methoxy;

wherein $R^{13b}$ is H;

wherein $R^{15}$ is selected from H and $C_{1-2}$-haloalkyl wherein $R^{16}$ is selected from
a) 4–6 membered saturated heterocyclyl,
b) 10 membered partially unsaturated heterocyclyl,
c) 5–10 membered heteroaryl,
d) $C_{1-3}$-aminoalkyl,
e) $C_{1-3}$-aminoalkylamino,
f) $C_{1-3}$-alkylamino-$C_{1-3}$-alkylamino,
g) $C_{1-3}$-alkylamino-$C_{1-3}$-alkyl,
h) phenylamino-$C_{1-3}$-alkyl,
i) phenyl-$C_{1-4}$-alkylamino-$C_{1-3}$-alkyl,
j) heterocyclyl-$C_{1-3}$-alkylamino-$C_{1-3}$-alkyl,
k) phenyl, naphthyl or tetrahydronaphthyl, provided $R^{16}$ is not 2-methoxyphenyl, 2-phenoxyphenyl or 2-phenylaminophenyl, l) $C_{1-3}$-alkyl,
m) phenyl-$C_{1-2}$-alkyl,
n) 5–10-membered saturated or partially unsaturated heterocyclylmethyl,
o) 5–6 membered heteroaryl-$C_{1-4}$-alkyl,
p) optionally substituted $C_{5-6}$-cycloalkyl,
q) $C_{1-3}$-aminoalkoxy,
r) [5- or 6-membered heterocyclyl]—$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;

wherein $R^{17}$ is selected from H, $C_{1-3}$-alkyl, —$(CH_2)_n$—$C_{3-6}$-cycloalkyl, and —$(CH_2)_n$-phenyl;

wherein $R^{19}$ is selected from H, $R^{23}SO_2$—, $C_{1-6}$-alkyl, amino-$C_{1-3}$-alkyl, $C_{1-6}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and —$(CH_2)_n$—$C_{3-5}$-cycloalkyl optionally substituted with $C_{1-2}$-alkoxycarbonyl;

wherein $R^{20}$ is selected from H, $C_{1-7}$-alkyl, —$(CH_2)_n$—$C_{5-6}$-cycloalkyl, —$(CH_2)_n$-5-6-membered heterocyclyl, $C_{1-3}$-alkylsulfonyl, amino-$C_{1-3}$-alkyl and —$(CH_2)_n$-phenyl;

alternatively $R^{19}$ and $R^{20}$ together with the nitrogen atom form a 4–7 membered heterocyclic ring;

wherein $R^{21}$ is selected from H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;

wherein $R^{22}$ is selected from H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

alternatively $R^{21}$ and $R^{22}$ together with the amide nitrogen atom form a 5–6 membered heterocyclic ring; and wherein $R^{23}$ is selected from H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

wherein phenyl, cycloalkyl and heterocyclyl are optionally substituted with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-2}$-haloalkoxy;

and pharmaceutically-acceptable salts thereof.

10. A compound of claim 9 wherein $R^{13a}$ is selected from H, bromo, phenyl and chloro;

wherein $R^{14}$ is selected from trifluoromethyl, 2-hydroxyethyl, 1-hydroxyethyl, $R^{19}R^{20}N$—, $R^{19}R^{20}N$—$C_{1-2}$-alkyl and $(R^{21}R^{22}N$—$)$ (O=)C—;

wherein $R^{15}$ is H or trifluoromethyl;

wherein $R^{17}$ is selected from H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;

wherein $R^{19}$ is selected from H, $R^{23}SO_2$—, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-(tert-butylmethyl) aminoethyl, di-(3-ethylbutyl)aminoethyl, di-(cyclohexylmethyl)aminoethyl, furylmethylaminoethyl, thienylmethylaminoethyl, benzylaminoethyl, di(furylmethyl)aminoethyl, di(cyclopropylmethyl)aminoethyl, di(thienylmethyl) aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, butylcarbonyl, tert-butylcarbonyl, pentylcarbonyl, cyclopentylcarbonyl, cyclopropylcarbonyl, cyclobutylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted thienylmethylcarbonyl, optionally substituted benzylcarbonyl, optionally substituted phenylethylcarbonyl, optionally substituted phenylcarbonyl and optionally substituted pyridylcarbonyl;

wherein $R^{20}$ is selected from H, methyl, ethyl, propyl, isopropyl, butyl, isobutyl, pentyl, hexyl, heptyl, cyclopropylmethyl, cyclobutylmethyl, cyclopentylmethyl, cyclobutylmethyl, cyclopropyl, cyclohexyl, methylsulfonyl, aminoethyl, optionally substituted phenyl, optionally substituted imidazolyl, optionally substituted imidazolylmethyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally substituted with one or more substituents selected from methyl, ethyl, propyl, and isopropyl, piperazinyl optionally substituted with one or more substituents selected from methyl, ethyl, propyl, and isopropyl, imidazolyl optionally substituted with one or more substituents selected from methyl, ethyl, propyl, and isopropyl, and pyrrolidinyl optionally substituted with one or more substituents selected from methyl, ethyl, propyl, and isopropyl;

wherein $R^{21}$ is selected from H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is H or methyl;

alternatively $R^{21}$ and $R^{22}$ together form a ring selected from pyrrolidinyl, morpholino, piperidinyl, piperazinyl, 4-acetylpiperazinyl and 4-methylpiperazinyl; and wherein $R^{23}$ is selected from H, methyl, ethyl, propyl, optionally substituted thienyl, optionally substituted phenyl, optionally substituted benzyl, optionally substituted phenylethyl and optionally substituted phenylpropyl;

wherein phenyl, cycloalkyl and heterocyclyl are optionally substituted with one or more substituents selected from trifluoromethyl, methyl, nitro, cyano, chloro, methoxy, phenyloxy, acetyl, amino, dimethylamino and aminomethyl;

and pharmaceutically-acceptable salts thereof.

11. A compound of claim 10 wherein $R^{14}$ is selected from N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl, 1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-yl-methyl, 3-pyridyl-oxymethyl, 2-methylimidazol-1-yl-methyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl, N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N—(N',N'-dimethylaminoethyl)amino, N— (N',N'-diethylaminoethyl)-N-methylsulfonylamino, N—(N',N'-dipropylaminoethyl)-N-methylsulfonylamino, N—(N',N'-diisobutylaminoethyl)-N-methylsulfonylamino, N—(N',N'-di-tert-butylmethylaminoethyl)-N-methylsulfonylamino, N—(N',N'-di(3-ethylbutyl)aminoethyl)-N-methylsulfonylamino, N—(N',N'-di(cyclopropylmethyl)aminoethyl)-N-methylsulfonylamino, N—(N',N'-di(cyclohexylmethyl)aminoethyl)-N-methylsulfonylamino, N—(N',N'-di(2-furylmethyl)aminoethyl)-N-methylsulfonylamino, N—(N',N'-di(3-thienylmethyl)aminoethyl)-N-methylsulfonylamino, N—(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6- trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-cyclohexylcarbonyl-N-cyclopropylmethylamino, N-thienylmethylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(4-methyl-5-imidazolylmethyl)-N-cyclopropylmethylamino, N-(4-imidazolylmethyl)-N-cyclopropylmethylamino, N-(5-imidazolylmethyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tertbutylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

and pharmaceutically-acceptable salts thereof.

12. A compound of claim 10 wherein $R^{12}$ is selected from

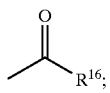

and wherein $R^{16}$ is selected from
a) 4–6 membered saturated heterocyclyl,
b) 10 membered partially saturated heterocyclyl,
c) 5–10 membered heteroaryl,
d) $C_{1-3}$-aminoalkyl,
e) $C_{1-3}$-aminoalkylamino,
f) $C_{1-3}$-alkylamino-$C_{1-3}$-alkylamino,
g) $C_{1-3}$-alkylamino-$C_{1-3}$-alkyl,
h) phenylamino-$C_{1-3}$-alkyl,
i) phenyl-$C_{1-4}$-alkylamino-$C_{1-3}$-alkyl,
j) heterocyclyl-$C_{1-3}$-alkylamino-$C_{1-3}$-alkyl,
k) phenyl, naphthyl or tetrahydronaphthyl,
l) $C_{1-3}$-alkyl,
m) phenyl-$C_{1-2}$-alkyl,
n) 5–10-membered saturated or partially unsaturated heterocyclylmethyl,
o) 5–6 membered heteroaryl-$C_{1-4}$-alkyl,
p) optionally substituted $C_{5-6}$-cycloalkyl,
q) $C_{1-3}$-aminoalkoxy,
r) [5- or 6-membered heterocyclyl]—$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;

wherein the heterocyclyl, aryl and cycloalkyl groups are optionally substituted;

and pharmaceutically-acceptable salts thereof.

13. A compound of claim 12 wherein $R^{16}$ is selected from N-(piperidylmethyl)amino, aminopropylamino, aminoethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl optionally N-substituted with a substituent selected from methyl, ethyl, propyl, isopropyl, butyl, isobutyl, pentyl, cyclohexylmethyl and benzyl, 6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl) methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino)ethyl, imidazol-4-yl-(1-amino)ethyl, phenyl-1-(methylamino)ethyl and phenyl-1-(amino)ethyl;

and pharmaceutically-acceptable salts thereof.

14. A compound of claim 13 and pharmaceutically acceptable salts thereof selected from N-[(1R)-1-[(4-chlorophenyl)methyl]-2-(4-{2-[(methylsulfonyl)amino]phenyl}-piperidyl)-2-oxoethyl]((3S)(3-1,2,3,4-tetrahydroisoquinolyl))carboxamide;

N-[(1R)-1-[(4-chlorophenyl)methyl]-2-(4-{2-[(methylsulfonyl)amino]phenyl}-piperidyl)-2-oxoethyl]((2S)-1-methylpyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]((3S,1R)-3-aminocyclopentyl)carboxamide;

N-[(1R)-1-[(4-chlorophenyl)methyl]-2-(4-{2-[(methylsulfonyl)amino]phenyl}-piperidyl)-2-oxoethyl]((1S,3R)-3-aminocyclopentyl)carboxamide;

N-[(1R)-1-[(4-chlorophenyl)methyl]-2-(4-{2-[(methylsulfonyl)amino]phenyl}-piperidyl)-2-oxoethyl](5-oxopyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]azetidin-3-ylcarboxamide;

N-[(1R)-1-[(4-chlorophenyl)methyl]-2-(4-{2-[(methylsulfonyl)amino]phenyl}-piperidyl)-2-oxoethyl]-2-(4-piperidyl)acetamide;

N-[(1R)-1-[(4-chlorophenyl)methyl]-2-(4-{2-[(methylsulfonyl)amino]phenyl}-piperidyl)-2-oxoethyl]((2S,3R)-3-phenylpyrrolidin-2-yl)carboxamide;

N-[(1R)-1-[(4-chlorophenyl)methyl]-2-(4-{2-[(methylsulfonyl)amino]phenyl}-piperidyl)-2-oxoethyl]((2S)pyrrolidin-2-yl)carboxamide;

((3S)(3-1,2,3,4-tetrahydroisoquinolyl))-N-[(1R)-1-[(3,4-dichlorophenyl)methyl]-2-(4-{2-[(methylsulfonyl)amino]phenyl}piperidyl)-2-oxoethyl]carboxamide;

N-[(1R)-1-[(4-chlorophenyl)methyl]-2-(4-{2-[(cyclopropylmethyl)-(methylsulfonyl)amino]phenyl}piperidyl)-2-oxoethyl]((3S)(3-1,2,3,4-tetrahydroisoquinolyl))carboxamide;

N-[(1R)-1-[(4-cChlorophenyl)methyl]-2-(4-{2-[(cyclopropylmethyl)-(methylsulfonyl)amino]phenyl}-piperidyl)-2-oxoethyl]azetidin-3-ylcarboxamide;

N-((1R)-1-[(4-chlorophenyl)methyl]-2-oxo-2-{4-[2-(trifluoromethyl)phenyl]-piperidyl}ethyl)((3S)(3-1,2,3,4-tetrahydroisoquinolyl))carboxamide;

N-((1R)-1-[(4-chlorophenyl)methyl]-2-{4-[2-(hydroxyethyl)phenyl]piperidyl}-2-oxoethyl)((3S)(3-1,2,3,4-tetrahydroisoquinolyl))carboxamide;

N-[(1R)-2-(4-{2-[(2-aminoethyl)(methylsulfonyl)amino]-phenyl}piperidyl)-1-[(4-chlorophenyl)methyl]-2-oxoethyl]((3S)(3-1,2,3,4-tetrahydroisoquinolyl))-carboxamide;

((3S)(3-1,2,3,4-tetrahydroisoquinolyl))-N-((1R)-1-[(4-chlorophenyl)methyl]-2-{4-[2-(3-methyl-2-oxo(4-imidazolinyl))phenyl]piperidyl}-2-oxoethyl)carboxamide;

((3S)(3-1,2,3,4-tetrahydroisoquinolyl))-N-((1R)-1-[(4-chlorophenyl)methyl]-2-oxo-2-{4-(2-(2-oxo(4-imidazolinyl))phenyl]piperidyl}ethyl)carboxamide;

N-((1R)-1-[(4-chlorophenyl)methyl]-2-oxo-2-{4-[2-(2-oxo(4-imidazolinyl))phenyl]-piperidyl}ethyl)azetidin-3-ylcarboxamide;

tert-butyl 3-(N-{(1R)-2-[4-(2-aminophenyl)piperidyl]-1-[(4-chlorophenyl)methyl]-2-oxoethyl}carbamoyl)(3S)-1,2,3,4-tetrahydroisoquinoline-2-carboxylate;

N-{(1R)-1-[(4-chlorophenyl)methyl]-2-[4-(2-{([(2-cyanophenyl)sulfonyl]amino}-phenyl)piperidyl]-2-oxoethyl}((3S)(3-1,2,3,4-tetrahydroisoquinolyl))carboxamide;

N-{(1R)-1-[(4-chlorophenyl)methyl]-2-oxo-2-[4-(2-{[(2,4,6-trimethylphenyl)sulfonyl]amino}phenyl)piperidyl]ethyl}((3S)(3-1,2,3,4-tetrahydroisoquinolyl))carboxamide;

N-[(1R)-1-[(4-chlorophenyl)methyl]-2-(4-{2-[(methylamino)carbonylamino]-phenyl}piperidyl)-2-oxoethyl]((3S)(3-1,2,3,4-tetrahydroisoquinolyl))carboxamide;

N-((1R)-1-[(4-chlorophenyl)methyl]-2-{4-[2-(methoxycarbonylamino)phenyl]piperidyl}-2-oxoethyl)((3S)(3-1,2,3,4-tetrahydroisoquinolyl))carboxamide;

N-[(1R)-1-[(4-chlorophenyl)methyl]-2-(4-{2-[(cyclopropylmethyl)amino]-phenyl}piperidyl)-2-oxoethyl]((3S)(3-1,2,3,4-tetrahydroisoquinolyl))carboxamide; and N-[(1R)-2-(4-{2-[(2-aminoethyl)amino]phenyl}piperidyl)-1-[(4-chlorophenyl)methyl]-2-oxoethyl]((3S)(3-1,2,3,4-tetrahydroisoquinolyl))carboxamide.

15. A compound of claim 10 wherein $R^{12}$ is selected from optionally substituted benzyl, and optionally substituted 5–10-membered heteroaryl; and wherein $R^{13a}$ and $R^{13b}$ are independently H or chloro.

16. A compound of claim 15 wherein $R^{12}$ is selected from oxazolo[5,4-b]pyridin-2-yl, oxazolo[4,5-b]pyridin-2-yl, 4-chlorobenzyl, benzoxazol-2-yl and benzyl.

17. A pharmaceutical composition comprising a pharmaceutically-acceptable carrier and a compound as in claim 1.

18. A method of treating obesity in a subject, said method comprising administering an effective amount of a compound of claim 1.

19. A method of treating diabetes mellitus in a subject, said method comprising administering an effective amount of a compound of claim 1.

* * * * *